United States Patent
Zhao et al.

(10) Patent No.: US 10,035,985 B2
(45) Date of Patent: Jul. 31, 2018

(54) HIGH TITER PRODUCTION OF ADENO-ASSOCIATED VIRAL VECTORS

(71) Applicant: THE SECRETARY OF STATE FOR HEALTH, London (GB)

(72) Inventors: Yuan Zhao, Potters Bar (GB); Stifani Satkunanathan, Potters Bar (GB)

(*) Notice: Subject to any disclaimer, the term of this patent is extended or adjusted under 35 U.S.C. 154(b) by 0 days.

(21) Appl. No.: 15/113,270

(22) PCT Filed: Jan. 30, 2015

(86) PCT No.: PCT/GB2015/050240
§ 371 (c)(1),
(2) Date: Jul. 21, 2016

(87) PCT Pub. No.: WO2015/114365
PCT Pub. Date: Aug. 6, 2015

(65) Prior Publication Data
US 2017/0029785 A1 Feb. 2, 2017

(30) Foreign Application Priority Data

Jan. 31, 2014 (GB) .................................. 1401707.3

(51) Int. Cl.
| | |
|---|---|
| *C12N 15/86* | (2006.01) |
| *C12N 7/00* | (2006.01) |
| *C12N 5/071* | (2010.01) |
| *C12N 5/073* | (2010.01) |
| *C12N 15/64* | (2006.01) |
| *C12P 19/34* | (2006.01) |

(52) U.S. Cl.
CPC ............... *C12N 7/00* (2013.01); *C12N 15/86* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 8,697,359 B1* | 4/2014 | Zhang .................... | C12N 15/85 424/94.1 |
| 2008/0145313 A1 | 6/2008 | Watson et al. | |

FOREIGN PATENT DOCUMENTS

| | | |
|---|---|---|
| WO | 03/046142 | 8/2003 |
| WO | 2004/113494 A2 | 12/2004 |
| WO | 2004/113494 A3 | 12/2004 |
| WO | 2011/094198 | 8/2011 |

OTHER PUBLICATIONS

Kerr et al., "Nucleophosmin is a novel Bax chaperone that regulates apoptotic cell death" 26 Oncogene 2443-2562 (2007).*

Search Report dated Oct. 7, 2014 in corresponding Great Britain Application No. GB1401707.3.
Johnson J.S. et al.: "Enhancement of Adeno-Associated Virus Infection by Mobilizing Capsids into and Out of the Nucleolus", Journal of Virology, 83(6): 2632-2644(2009).
Weng J.J et al.: "Nucleophosmin/B23 regulates PCNA promoter through YY1", Biochemical and Biophysical Research Communications, 335(3): 826-831(2005).
Lin, M.H. et al.: "Establishment of nucleophosmin gene silenced HL 60 and its resistant cell line", Journal of Experimental Hematology, 19(6): 1393-1398(2011).
Lin M. et al.: "Knockdown of nucleophosmin by RNA interference reverses multidrug resistance in resistant leukemic HL-60 cells", Immunobiology, 218(9): 1147-1154(2013).
Qing Y. et al.: "Role of Npm1 in proliferation, apoptosis and differentiation of neural stem cells", Journal of the Neurological Sciences, 266(1-2): 131-137(2008).
Shandilya J. et al.: "Acetylated NPM1 Localizes in the Nucleoplasm and Regulates Transcriptional Activation of Genes Implicated in Oral Cancer Manifestation", Molecular and Cellular Biology, 29(18): 5115-5127(2009).
Wang B.B. et al.: "Inducible and reversible suppression of Npm1 gene expression using stably integrated small interfering RNA vector in mouse embryonic stem cells", Biochemical and Biophysical Research Communications, 347(4): 1129-1137(2006).
Liu Y. et al.: "Expression of nucleophosmin/NPM1 correlates with migration and invasiveness of colon cancer cells", Journal of Biomedical Science, 19: 53(2012).
Perez-Leal O. et al.: "Polyamine-Regulated Translation of Spermidine/Spermine-N1-Acetyltransferase", Molecular and Cellular Biology, 32(8): 1453-1467(2012).
Office Action dated Dec. 4, 2017 in European Patent Application No. 15 702 840.8.
Invitation to Respond to Written Opinion dated Sep. 26, 2017 in Singapore Patent Application No. 11201605848T.
Johnson et al.: "Enhancement of Adeno-Associated Virus Infection by Mobilizing capsids into and out of the Nucleolus", Journal of Virology, 83(6):2632-2644 (2009).
Kaludov et. al.: "Scalable purification of adeno-associated Virus Type 2, 4, or 5 Using Ion-Exchange Chromatography", Human Gene Therapy, 13:1235-1243 (2002).
Satkunanathan et al.: "Establishment of a Novel Cell Line for the Enhanced Production of Recombinant Adeno-Asoociated Virus Vectors for Gene Therapy", Human Gene Therapy, 25:929-941 (2014).
Nash et al.: "Identification of Cellular Proteins That Interact with the Adeno-Asoociated Virus Rep Protein", Journal of Virology, 83(1): 454-469 (2009).
Perez-Leal et al.: "Polyamine-Regulated Translation of Spermidine/Spermine-N1-Acetyltransferase", Molecular and Cellular Biology 32(8):1453-1467 (2012).
Mu et al.: "YB-1 stabilizes HIV-1 genomic RNA and enhances viral production", Protein Cell, 4(8):591-597 (2013).
Shen et al.: "Nuclease Sensitive element Binding Protein 1 Associates With the Selenocysteine Insertion Sequence and Functions in Mammalian Selenoprotein Translation", J Cell Physiol, 207(3):775-783 (2006).

(Continued)

*Primary Examiner* — Nancy J Leith
(74) *Attorney, Agent, or Firm* — Wenderoth, Lind & Ponack, L.L.P.

(57) ABSTRACT

This invention relates to adeno-associated viral (AVV) vectors, to producer cell lines for the production of AAV vectors and to methods of producing such vectors. More specifically, the invention relates to producer cell lines adapted to increase the titer of said vectors and methods of producing AAV vectors using said producer cell lines.

23 Claims, 19 Drawing Sheets

(56) References Cited

OTHER PUBLICATIONS

Chatel-Chaix et al.: "Y-Box-Binding Protein 1 Interacts with Hepatitis C Virus NS3/4A and Influences the Equilibrium betwen Viral RNA Replication and Infection Particle Production", Journal of Virology, 85(21):11022-11037 (2011).
Kawaguchi et al.: "YB-1 Functions as a Porter to Lead Influenza Virus Ribonucleoprotein Complexes to Microtubules", Journal of Virology, 86(20): 11086-11095 (2012).
International Search Report and Written Opinion dated Apr. 30, 2015 in corresponding International Application No. PCT/GB2015/050240.
Search Report dated Dec. 1, 2014 in corresponding GB Application No. GB1401707.3.

\* cited by examiner

Figure 14

YB1 mRNA sequence (SEQ ID NO: 3)

```
   1 gggcttatcc cgcctgtccc gccattctcg ctagttcgat cggtagcggg agcggagagc
  61 ggaccccaga gagccctgag cagccccacc gccgccgccg gcctagttac catcacaccc
 121 cgggaggagc cgcagctgcc gcagccggcc ccagtcacca tcaccgcaac catgagcagc
 181 gaggccgaga cccagcagcc gccgccgcc cccccgccg ccccgccct cagcgccgcc
 241 gacaccaagc ccggcactac gggcagcggc gcagggagcg gtggccgggg cggcctcaca
 301 tcggcggcgc ctgccggcgg ggacaagaag gtcatcgcaa cgaaggtttt gggaacagta
 361 aaatggttca atgtaaggaa cggatatggt ttcatcaaca ggaatgacac caaggaagat
 421 gtatttgtac accagactgc cataaagaag aataacccca ggaagtacct tcgcagtgta
 481 ggagatggag agactgtgga gtttgatgtt gttgaaggag aaaagggtgc ggaggcagca
 541 aatgttacag gtcctggtgg tgttccagtt caaggcagta aatatgcagc agaccgtaac
 601 cattatagac gctatccacg tcgtaggggt cctccacgca attaccagca aaattaccag
 661 aatagtgaga gtggggaaaa gaacgaggga tcggagagtg ctcccgaagg ccaggcccaa
 721 caacgccggc cctaccgcag gcgaaggttc ccaccttact acatgcggag accctatggg
 781 cgtcgaccac agtattccaa ccctcctgtg cagggagaag tgatggaggg tgctgacaac
 841 cagggtgcag gagaacaagg tagaccagtg aggcagaata tgtatcgggg atatagacca
 901 cgattccgca ggggccctcc tcgccaaaga cagcctagag aggacggcaa tgaagaagat
 961 aaagaaaatc aaggagatga gacccaaggt cagcagccac ctcaacgtcg gtaccgccgc
1021 aacttcaatt accgacgcag acgcccagaa acccctaaac cacaagatgg caaagagaca
1081 aaagcagccg atccaccagc tgagaattcg tccgctcccg aggctgagca gggcggggct
1141 gagtaaatgc cggcttacca tctctaccat catccggttt agtcatccaa caagaagaaa
1201 tatgaaattc cagcaataag aaatgaacaa agattggag ctgaagacct aaagtgcttg
1261 cttttgccc gttgaccaga taaatagaac tatctgcatt atctatgcag catggggttt
1321 ttattatttt tacctaaaga cgtctctttt tggtaataac aaacgtgttt tttaaaaaag
1381 cctggttttt ctcaatacgc ctttaaaggt ttttaaattg tttcatatct ggtcaagttg
1441 agatttttaa gaacttcatt tttaatttgt aataaaagtt tacaacttga ttttttcaaa
1501 aaagtcaaca aactgcaagc acctgttaat aaaggtctta ataataaaa aaaaaaaaaa
1561 a
```

YB1 amino acid sequence (SEQ ID NO: 29)

```
  1   MSSEAETQQPPAAPPAAPALSAADTKPGTTGSGAGSGGPGGLTSAAPAGGDKKVIATKVL    60
 61   GTVKWFNVRNGYGFINRNDTKEDVFVHQTAIKKNNPRKYLRSVGDGETVEFDVVEGEKGA   120
121   EAANVTGPGGVPVQGSKYAADRNHYRRYPRRRGPPRNYQQNYQNSESGEKNEGSESAPEG   180
181   QAQQRRPYRRRRFPPYYMRRPYGRRPQYSNPPVQGEVMEGADNQGAGEQGRPVRQNMYRG   240
241   YRPRFRRGPPRQRQPREDGNEEDKENQGDETQGQQPPQRRYRRNFNYRRRRPENPKPQDG   300
301   KETKAADPPAENSSAPEAEQGGAE    324
```

Figure 15

NPM1 mRNA sequence (SEQ ID NO: 1)

```
   1 ggggcctggt gtgattccgt cctgcgcggt tgttctctgg agcagcgttc ttttatctcc
  61 gtccgccttc tctcctacct aagtgcgtgc cgccacccga tggaagattc gatggacatg
 121 gacatgagcc ccctgaggcc ccagaactat ctttcggtt gtgaactaaa ggccgacaaa
 181 gattatcact ttaaggtgga taatgatgaa atgagcacc agttatcttt aagaacggtc
 241 agtttagggg ctggtgcaaa ggatgagttg cacattgttg aagcagaggc aatgaattac
 301 gaaggcagtc caattaaagt aacactggca actttgaaaa tgtctgtaca gccaacggtt
 361 tccttgggg gctttgaaat aacaccacca gtggtcttaa ggttgaagtg tggttcaggg
 421 ccagtgcata ttagtggaca gcacttagta gctgtggagg aagatgcaga gtcagaagat
 481 gaagaggagg aggatgtgaa actcttaagt atatctggaa agcggtctgc cctggaggt
 541 ggtagcaagg ttccacagaa aaaagtaaaa cttgctgctg atgaagatga tgacgatgat
 601 gatgaagagg atgatgatga agatgatgat ggtgatgatt ttgatgatga ggaagctgaa
 661 gaaaaagcgc cagtgaagaa atctatacga gatactccag ccaaaaatgc acaaaagtca
 721 aatcagaatg gaaaagactc aaaaccatca tcaacaccaa gatcaaaagg acaagaatcc
 781 ttcaagaaac aggaaaaaac tcctaaaaca ccaaaaggac ctagttctgt agaagacatt
 841 aaagcaaaaa tgcaagcaag tatagaaaaa ggtggttctc ttcccaaagt ggaagccaaa
 901 ttcatcaatt gtgtgaagaa ttgcttccgg atgactgacc aagaggctat tcaagatctc
 961 tggcagtgga ggaagtctct ttaagaaaat agtttaaaca atttgttaaa aaattttccg
1021 tcttatttca tttctgtaac agttgatatc tggctgtcct ttttataatg cagagtgaga
1081 actttcccta ccgtgtttga taaatgttgt ccaggttcta ttgccaagaa tgtgttgtcc
1141 aaaatgccgt ttagttttta aagatggaac tccaccctt gcttggtttt aagtatgtat
1201 ggaatgttat gataggacat agtagtagcg gtggtcagac atggaaatgg tggggagaca
1261 aaaatataca tgtgaaataa aactcagtat tttaataaag tgaaaaaaaa aaaaaaaaaa
1321 aaaaaaaaaa a
```

NPM1 amino acid sequence (SEQ ID NO: 27)

```
  1   MEDSMDMDMSPLRPQNYLFGCELKADKDYHFKVDNDENEHQLSLRTVSLGAGAKDELHIV    60
 61   EAEAMNYEGSPIKVTLATLKMSVQPTVSLGGFEITPPVVLRLKCGSGPVHISGQHLVAVE   120
121   EDAESEDEEEEDVKLLSISGKRSAPGGGSKVPQKKVKLAADEDDDDDEEDDDEDDDGDD    180
181   FDDEEAEEKAPVKKSIRDTPAKNAQKSNQNGKDSKPSSTPRSKGQESFKKQEKTPKTPKG   240
241   PSSVEDIKAKMQASIEKGGSLPKVEAKFINCVKNCFRMTDQEAIQDLWQWRKSL         294
```

Figure 16

NCL mRNA sequence (SEQ ID NO: 2)

```
   1 attctgctgt agacatagag atgatgatca tagctgacta tgatgatgat cccccgcgag
  61 cctgaaagag gaaatgctct ggtttgctaa gcccgcgaat cgagtgagac ccacccacaa
 121 agctaaccgt ggaagtcact ggcggcctcc ttcgccctgc cagccgggga acccatccgg
 181 tggctctcga cctgctcccg ggccatctgg tgacactgac ttcgcagcca ccaccttaat
 241 tggcgcattc gacccaaata taacctggg aacctgtggg cggtctaagg cccggctctg
 301 cggtcgccct cccaggcccc tctccctggc cctgtgaggc cagaaagtta cttctccgag
 361 gccagttccc catgtctgag aaatatctcc aacttgagg ttctgtgggg tagggaggg
 421 ttcgtgactt tctcacagaa aacctcgtac agacccgcc actgccttta ttaacagctc
 481 tcaggagact gcctgcagga ggggggtcgc tccggcccca tgctcgcggg caagcaggga
 541 taagctgtgc ctccaaaagg gccaacggga actccgcggt ccctgaactt ccggtgctgg
 601 aggactcctc gctccaggc caccaggagc cgcggcgtga gtgcgtgccg gaaccgaggg
 661 cggggtctct gaggaactcc aaggctgccc aagcctacgg acccagccac attggcgaac
 721 cggagaccgc ccgattccac cacccccgcg ctcccctcac agccggcgcc aaaaacgcca
 781 gtcccacgac gcaggccggg acccgcgcgc ccacggccca atcagcgcga ccttgcacaa
 841 agcgagcccc gcccccacgg cgccgttgcc agcccctccc cctcccgtgc cgcctcggcc
 901 cgcctactcc ccgccccgcg ccgttcacgg ttagaggctc gcgattggct catgggacg
 961 gccgcgagct ttggttggtc ggcgcggagt cacgaggcgc cgtcgtcgcc tttccacagg
1021 cgttactggg caggctcagt ctttcgcctc agtctcgagc tctcgctggc ttcgggtgta
1081 cgtgctccgg gatcttcagc acccgcggcc gccatcgccg tcgcttggct tcttctggac
1141 tcatctgcgc cacttgtccg cttcacactc cgccgccatc atggtgaagc tcgcgaaggt
1201 aaacggcctt gagcgcgacg cagacgtgta ggcctgcttc cgaggggcga gcgcggcgcc
1261 gcggggagga gggcctgcgc gcagtcccgg gcgcgttcta gggcgccatg ctgcgggaag
1321 tctcgcgcga ttagtgggga ggtctcgcgc ttctggctac ttggtggcga ggtgaagagc
1381 ttctgcaggt gctgggggag ggggcgctgg gcctcggggt ggagagatga gaccaaactt
1441 ttgcgacgcg tacgagctgg gactgactct gacgcacgtg cccgggagcg tgcctgccac
1501 gtgggccggc gtaggtctgg aatctccaga gggaccgggt gccttgggcc gggaaatggc
1561 ggtatcggcc ctagtcggag tcccggctgc gctcggatgt ctccgccccg gcctggcaag
1621 ccgatacgtg gtgggccccg gaaggtggct ctgccgcgtg ccttttgcgc tgtgtttcgg
1681 gcaagaggtg gtcctgccag gtaccccac gtggccgcac ccgcctcttt aaggggcggg
1741 gtagtgctgg ggaaaggcat aagcttcatg agaaaataag gtagtatttt taagtgcctt
1801 aatgatcttc accgttaatt tgattcaaat aagggtggta gataaagtac cgggatttgt
1861 agtataaaaa cacggttgtg cttaactaag gtaacgggag gagaaatcat ttcctcaggt
1921 tgactttta ccttagggca ggttttctgt tggtaaagcc tgggaggaaa aatgtgggcg
1981 gttgagaagt agtccctctt gcattgccat caggagtagt ttctatgtta gttgtggtgt
2041 ttggcactat gagaaatgat ctgagacgga gatgatggcg tatgaacact aatggcaaaa
2101 tatgaatggc ctgaaatgtc gaggtggagg tgtaatgatc tatttgtgtc cattttaggc
2161 aggtaaaaat caaggtgacc ccaagaaaat ggctcctcct ccaaaggagg tagaagaaga
2221 tagtgaagat gaggaaatgt cagaagatga agaagatgat agcagtggag aagaggtaat
2281 tttatccaac ttaatgcaga attatgttaa aactacaaaa tggagagtta agacatgaaa
```

Figure 16 (cont.)

```
2341 ttggatatct gtggcaaaaa taagatttta tcaggtatgt cttattgtag tggttgagtg
2401 tttcacaagc tcttcattga catgtcaaga tgtcatttgg ctagtatttg aatgtgagtg
2461 ctaagacgag actgggaatt tcttttacat gttcctctgc agggcttgga gtgtgatttg
2521 ttgtgttaaa tcattacatt tttccagttt caacatgtta gctcaccccc acatgtagag
2581 ctgggcattg tattcagagc tgagaataac cttaccagat tcctttccta tcctccgaat
2641 taaaattaat tggtctccat tccatatata tataactgta tcactactgg ttaagtactc
2701 gggtgtagac tgagggctgc cacctctctt tggtaccatt gaccctcttt agccacctcc
2761 tggcctttta tttgcctcca ctataaagac agctgagcac tgaattgtgc tcaggttttc
2821 gttgagaacc tgaatgaaag ttttactctc cacacattgc cttgataaaa ctacgggatt
2881 ttaatgtagc taaatgatga cttttatcaa actaccatgc acactctttg atgtgtgata
2941 gttttgtaag gaatatttat atttagccta ttcattttt gtctcaggtc ctaagaattg
3001 agcttcactg ggcttggtgg accgcaacca cgagggcccc aatgatttaa taagttaatg
3061 cttggagcct cctatgtgta acgttctgaa taatttacac atagcaattc atgaccttaa
3121 acatgtaagg atgatactat taccattttc agatgagaaa gttggggctt gggaaagtat
3181 gaggtgtaag aattcagagg gtctggttca gaggtatttt cagtgttcaa aagagttcct
3241 tatgtctggg tattcacctt attataggg ctctgactta agacaacata acagaagcct
3301 ggagttttaa catgtcatat gtgtcatgcg tatgtcttga accagaggca ttgccagagt
3361 ctaacaactc attgggacca tggttatctt tttgggtgtg gggctggact tactggtttg
3421 gttttcattt atctcaaggt cgtcatacct cagaagaaag gcaagaaggc tgctgcaacc
3481 tcagcaaaga aggtggtcgt ttccccaaca aaaaaggttg cagttgccac accagccaag
3541 aaagcagctg tcactccagg caaaaaggca gcagcaacac ctgccaagaa gacagttaca
3601 ccagccaaag cagttaccac acctggcaag aagggagcca caccaggcaa agcattggta
3661 gcaactcctg gtaagaaggg tgctgccatc ccagccaagg gggcaaagaa tggcaagaat
3721 gccaagaagg aagacagtga tgaagaggag gatgatgaca gtgaggagga tgaggaggat
3781 gacgaggacg aggatgagga tgaagatgaa attgaaccag cagcgatgaa agcagcagct
3841 gctgcccctg cctcagagga tgaggacgat gaggatgacg aagatgatga ggatgacgat
3901 gacgatgagg aagatggtaa ggagttgtct tggtagttac tgggcttctg attacaaggt
3961 atcttgagat tctgggatca catattcctt catcgtacaa cctggagatg agattagaat
4021 cttgtgggaa ttctcttggg ttgttgtggt gtgctagact taattaccca tgaatgattt
4081 tgtcctcttg agaaaatttc aatagcacat ctattagtgt tttttataat gtaggatttt
4141 cgtttctaag tgatttttt tttttttaa atttttttga gatggagctt ttgctgtttc
4201 ccaggcggga gtgcaatggc gcgctatctc ggcgcactgc agcctccatc tcctgggttc
4261 aagcagttct gcctcagcct cccgagtagc gggattacag gtgcccacca ccacaccta
4321 ctaattttgt attttagtag agacgacatt tcaccatgtt ggccaggctg gctctgaact
4381 ttgacctcag gtgatccacc caccttaggc tctcccaaag tgctaggatt acaggtgaga
4441 tatgctgcgc ccggccccaa gtgatctatt cttgccatga ctgttaacta aacatggtga
4501 caggattcga ttttctttac attagatttg aaaaccgatg ttggttttgg gagattgctg
4561 caattttag gtgacttctc tttcagactc tgaagaagaa gctatggaga ctacaccagc
4621 caaaggaaag aaagctgcaa agttgttcc tgtgaaagcc aagaacgtgg ctgaggatga
4681 agatgaagaa gaggatgatg aggacgagga tgacgacgac gacgaagatg atgaagatga
4741 tgatgatgaa gatgatgagg aggaggaaga agaggaggag gaaggtactt aaattagatt
4801 ctgacatacg acatgagtta tgtttaaagg aggcacttaa gtgtttgtgg ctactgatgt
4861 gtgatacatt gtttgacatc ttgtccagag cctgtcaaag aagcacctgg aaaacgaaag
```

Figure 16 (cont.)

```
4921 aaggaaatgg ccaaacagaa agcagctcct gaagccaaga aacagaaagt ggaaggtaac
4981 ttgcagaatt aggggatatg ggggagataa acagcacaaa tgatgaataa caaagggact
5041 taatactgaa accagatgtt acattgtagt gtgctgatgt gctgtgtata gaaattttgc
5101 tttggaaact aactttttac cacactacaa gtagactgag ttgagctttt tttgtgcagg
5161 cacagaaccg actacggctt tcaatctctt tgttggaaac ctaaacttta acaaatctgc
5221 tcctgaatta aaaactggta tcagcgatgt ttttgctaaa aatgatcttg ctgttgtgga
5281 tgtcagaatt ggtatgacta ggtagctgct tcactgcacg ttacataccg tgggtctgtt
5341 aattttccct tccctgtta gcacagttac tttagcctgc cactgttaaa catgaatact
5401 gtaaacactt caaggttagc attagtgaac taagttagaa ttaaactgta gatcccctaa
5461 gttgcaattt ccataatcag tcgtaacttg gtatagcaca gaataatttt tagtaatttt
5521 tttgttgttt ttgttatgta ttgagacgga cgctggcttt tgttcaggct ggagtacagt
5581 ggcgcaatct tggctcactg caacctctgc ctcccgggtt caagcgattc tcctgcctaa
5641 cctcccaagt gactgggata cgggtgccac tcaccatgca tggctaattt ttgttttgta
5701 tttagtatcg atttcaccat gttggtcggc tggttttgaa ctcctgacct caagtgatcc
5761 acccacctcg gcctctcgaa gtgctggtac agcgtcacca ccctgccagt aagttttaat
5821 aatttggtgt taggtgggag aatgcttgaa cctgggaggc agaggttgca gtgagccaag
5881 ttcgcgccac tgtactccag cctgggcaac agattgagac accgtctcaa tttaaaataa
5941 tgtttatttt cttggaagta ccttgaaact attagacctg tctagtcatc atagtgaata
6001 cttttatcca gacaggattc tcctgtatta gtgcttatag gtgttctttt gtcagctgct
6061 actgtgaatt cttataagca atttagctcc atgatgaaga cctcaaacgt gaatgtgcat
6121 gtcatatctt catgctgagc cgtgttctgt agctgcagtt tgcagagcct tgactttgtt
6181 ttgctatact aggggtgctt tttaaaatgt gatctttgtt tgcaccatca catttgtcta
6241 gatacagatt gtgattttga tttgtgtttt cacctgttgt aattttgccc tcctctccac
6301 ctgaaggaaa tttggttatg tggattttga atctgctgaa gacctggaga aagcgttgga
6361 actcactggt ttgaaagtct ttggcaatga aattaaacta gagaaaccaa aaggaaaaga
6421 cagtaagaaa ggtatgtaag gctttatgag ttatgcaatg aactcaggag ctagactgct
6481 agggaaaatg ctttgtaacc catttccctt tggtttcctc ttatttttt taaatcattt
6541 ttttcctttg gtttcctctt aatgtgggaa ttaaatgagc tacagtgttt acaaggtact
6601 tggcactgct tgtcagtgta taggtaaatt cctgagttag gcaagcaaga gcactcttat
6661 acagaacaag aaccattaca tgcacctaaa ttaagctaag gatctttctt cactgaaact
6721 agttaggtcc ctaattactc cctatataca gtgtaatgtt ttgaattggt acattcactt
6781 ttttgttat gcgcgtctac tctaggttga actccagtgt acctaacaga gagtttgaca
6841 tcaaggctgt gacaacatgg agggaccact tgtgtgttga cactgctata tctccatatt
6901 tagcaccgag ccttgtacat ataggatctc aaattatttg ttgatagagc tatgtgtgtt
6961 tttcccctct ttttgttgtt gccccccacc tttggttttt caggccacag agctcatttt
7021 tgtttttta atctagagcg agatgcgaga acacttttgg ctaaaaatct cccttacaaa
7081 gtcactcagg atgaattgaa agaagtgttt gaagatgctg cggagatcag attagtcagc
7141 aaggatggga aaagtaaagg gtatgttctt ctattgaaat gtaagggttt tattaacatt
7201 aatgcacttc ctgctttata aaagaaatat tggtttgatt tccttaggcg tgtaacttgg
7261 acagtttaac ctgtaagttt gtgcctcagt aacccatctg taccatgggg ataatgtact
7321 catagggtga ttttaaaaga caaagctaat acttacaaag aagcaagttt aatgcctatc
7381 ttacataaat actttgtaag tagtagcagt tctttcagtg aggtgaggtt acatgaaaaa
```

Figure 16 (cont.)

```
7441 attccaagta tttgtaaaac tagtgggaag taagagggaa gctcgagttt tgattgaaaa
7501 gtggactaaa caagggcatt ttatgtactc agatctgaag caagttctgt gttgctgagg
7561 taaaagcatt tgtgttaata tggttttaaa accatgagt tcttctccct ccattgcagg
7621 attgcttata ttgaatttaa dacagaagct gatgcagaga aaacctttga agaaaagcag
7681 ggaacagaga tcgatgggcg atctatttcc ctgtactata ctggagagaa aggtcaaaat
7741 caagactata gaggtggaaa gaatagcact tggagtggta agaaattagg cttgttccaa
7801 ggttttcaga attggttgag ggaactcttc tagtctttgt atttcataag tttataaata
7861 ctttttaatc aaagttactc aaatgtaggt gaagatcaag gacatgatac cccaagtcat
7921 actcttattt ggaatagtaa tttccaatct tgaaatgaga gctctaaatc attttgcatt
7981 ggaatacagt aggcaaatca agcttccttt gtaggcatgt tttatacttt aaatgacttg
8041 accatgtgcg ttttgaactc agatgattct aggaaaacag accagtcatc agcctatgta
8101 agaacaacca gcaggacatt gcaacacgta ctaggtactt aatatgttga gtaacagaaa
8161 tggatttagc ttacgtcatg agtatttgta tataactcaa gcactgaaat tcttagggaa
8221 tagatattac tgttgtgacc gaagctggga cactgtttca gagtcttagg aatgtggctc
8281 tctatttcga ggtgaatcaa aaactctggt tttaagcaac ctctcctaca gtgcaacaga
8341 agaaactctt caggaagtat ttgagaaagc aacttttatc aaagtacccc agaaccaaaa
8401 tggcaaatct aaagggtaag ataatacctt tgtatcatca gttataggcc tatatatgtc
8461 ttagaggtct aaggacgtaa ggtcatgtgt cctgtagaaa aaagctaaat aattttagcc
8521 tagtaaatga gtgtaaaata agtatattta ggtccaacct tgagagaagg gccttggcca
8581 gatcatgtga ccagtggtat agagagcatg tgcctggtaa attactctaa gcattaactg
8641 ttcatcctca ggtatgcatt tatagagttt gcttcattcg aagacgctaa agaagcttta
8701 aattcctgta ataaagggaa aattgagggc agagcaatca ggctggagtt gcaaggaccc
8761 aggggatcac ctaatgccag aagccgtaag ttcacctggt tagggtgctg tggttggggg
8821 tagcactctc ggtgctttgt ttattttttgc acaaattctg tgtttcctgt tcgctactga
8881 gtgaacaata actggatatc gatgactgat tacctgagaa ataattgatg aaatctcaag
8941 aaaattcctc tagatagtca agttctgatc cagctgtcgt caactcagag tagcaagttt
9001 gcccatgatt tcctgcccca tccactgggc cccacctgct tgggttgctt tcccactttc
9061 catagaagac tggggcagga tatcaactat gcaatggcaa ttaaaaatg taaacccaga
9121 atagccttta cttttaattaa ggactagttg gcttagttgc ttttaactgc ttttttcacta
9181 taacaagtat cttggctagt agtcatacta ggcattgtgc aaattcagtg tacgaactgt
9241 gaattcacat aaatcgcaaa ttttttttc cttcccagag ccatccaaaa ctctgtttgt
9301 caaaggcctg tctgaggata ccactgaaga gacattaaag gagtcatttg acggctccgt
9361 tcgggcaagg atagttactg accgggaaac tgggtcctcc aaagggtaag ggaaggaagc
9421 gtgagtgctg cttccacttg aaggggtttt tgttctgtgc agaccttgag tctaatgtgt
9481 cttctcattg agctccttct gtctatcagt ggcagtttat ggattcgcac gagaagaaga
9541 gagaattcac agaactagca ttattttacc ttctgtcttt acagaggtat atttagctgt
9601 attgtgagac attctggggt tcaagctgtc acaccagtta gttttccata gagagctact
9661 ctgctgcact ggtatctttt tcccaaataa acaaggctac ttctgtggga tggctccca
9721 gcatgtacag ttaacttggg acatgtgtag taggtgcttt ttataatggg caatttcatt
9781 tggtgttcta ggtttggttt tgtagacttc aacagtgagg aggatgccaa ggaggccatg
9841 gaagacggtg aaattgatgg aaataaagtt accttggact gggccaaacc taagggtgaa
9901 ggtggcttcg ggggtcgtgg tggaggcaga ggcggctttg gaggacgagg tggtggtaga
```

Figure 16 (cont.)

```
 9961 ggaggccgag gaggatttgg tggcagaggc cggggaggct ttggaggtaa ggcacgcaga
10021 gataatgaca ccacatagca tgtgctcttc agaccctgtg ccctgtcacg gttcctaatc
10081 actggggagg aggagctttg tacccattct tttaacagtg tcttgccttc ctcctgtagg
10141 gcgaggaggc ttccgaggag gcagaggagg aggaggtgac cacaagccac aaggaaagaa
10201 gacgaagttt gaatagcttc tgtccctctg ctttcccttt tccatttgaa agaaaggact
10261 ctggggtttt tactgttacc tgatcaatga cagagccttc tgaggacatt ccaagacagt
10321 atacagtcct gtggtctcct tggaaatccg tctagttaac atttcaaggg caataccgtg
10381 ttggttttga ctggatattc atataaactt tttaaagagt tgagtgatag agctaaccct
10441 tatctgtaag ttttgaattt atattgtttc atcccatgta caaaaccatt ttttcctaca
10501 aatagtttgg gttttgttgt tgttactttt ttttttgttt ttgtttttt ttttttgcg
10561 ttcgtggggt tgtaaaagaa aagaaagcag aatgttttat catggttttt gcttcaccgc
10621 tttaggacaa attaaaagtc aactctggtg ccagacgtgt tacttcctaa agagtgtttc
10681 ccctggaatc tcactggaga gcatggcaaa gccagctctg ccacttgctt cacccatccc
10741 aatggaaatg cttagtgcg tgtttccagt atcccagccc taactaactt ggttgaaatg
10801 ctggtgaggg gacctgctcc tgcagccctg gtgctgactt gaaggctgct gcagcttctc
10861 ctactttag caggtctcga ggattatgtc tgaagaccac tctggaaaga ggtcgaggaa
10921 cagattagtc aggtttccta gg
```

NCL amino acid sequence (SEQ ID NO: 28)

```
  1  MVKLAKAGKNQGDPKKMAPPPKEVEEDSEDEEMSEDEEDDSSGEEVVIPQKKGKKAAATS   60
 61  AKKVVVSPTKKVAVATPAKKAAVTPGKKAAATPAKKTVTPAKAVTTPGKKGATPGKALVA  120
121  TPGKKGAAIPAKGAKNGKNAKKEDSDEEEDDDSEEDEEDDEDEDEDEDEIEPAAMKAAAA  180
181  APASEDEDDEDDEDDDDDEEDDSEEEAMETTPAKGKKAAKVVPVKAKNVAEDEDEEE     240
241  DDEDEDDDDEDDEDDDDEDDEEEEEEEEEEPVKEAPGKRKKEMAKQKAAPEAKKQKVEG  300
301  TEPTTAFNLFVGNLNFNKSAPELKTGISDVFAKNDLAVVDVRIGMTRKFGYVDFESAEDL  360
361  EKALELTGLKVFGNEIKLEKPKGKDSKKERDARTLLAKNLPYKVTQDELKEVFEDAAEIR  420
421  LVSKDGKSKGIAYIEFKTEADAEKTFEEKQGTEIDGRSISLYYTGEKGQNQDYRGGKNST  480
481  WSGESKTLVLSNLSYSATEETLQEVFEKATFIKVPQNQNGKSKGYAFIEFASFEDAKEAL  540
541  NSCNKREIEGRAIRLELQGPRGSPNARSQPSKTLFVKGLSEDTTEETLKESFDGSVRARI  600
601  VTDRETGSSKGFGFVDFNSEEDAKEAMEDGEIDGNKVTLDWAKPKGEGGFGGRGGGRGGF  660
661  GGRGGGRGGRGGFGGRGRGGFGGRGGFRGGRGGGGDHKPQGKKTKFE  707
```

HIGH TITER PRODUCTION OF ADENO-ASSOCIATED VIRAL VECTORS

FIELD OF THE INVENTION

This invention relates to adeno-associated viral (AVV) vectors, to producer cell lines for the production of AAV vectors and to methods of producing such vectors. More specifically, the invention relates to producer cell lines adapted to increase the titre of said vectors and methods of producing AAV vectors using said producer cell lines.

BACKGROUND OF THE INVENTION

Adeno-associated viral (AAV) vectors have excellent safety profiles because wild type AAV has never been associated with any human disease. Thus, AAV are popular and successful vectors for gene therapies. AAV vectors have been extensively studied in clinical trials for many different conditions, including haemophilia B, heart disease and congenital blindness. In addition, the first EU licenced gene therapy drug, Glybera, is based on AAV vector for the treatment of familial lipoprotein lipase deficiency (LPLD), exemplifying the potential of AAV vectors in gene therapy.

Although many advances have been made in AAV vector design, barriers such as a pre-existing immune response have necessitated the administration of high titre AAV and, in many cases, a combined administration of an immunesuppressant to achieve clinical efficacy. This presents a significant challenge in AAV production and has considerable safety implications in the clinical use of AAV vectors.

AAV vectors are most commonly produced by a transient co-transfection of AAV plasmids and a helper plasmid derived from another virus, such as an adenovirus. Significant progress has recently been made in large scale production and robust purification of AAV to support clinical development. However, production of high titre AAV is still a significant challenge, requiring patients to receive repeated administrations of a vector to achieve the desired dosage. For example, for Glybera, it is required to administer the vector at a dose of $3\times10^{12}$ vg/kg via 40 or 60 multiple injections.

Furthermore, as a result of current purification methods, AAV products typically contain high levels of protein aggregates or incompletely packaged empty capsids that lack vector DNA. The empty capsids in final products can often be as high as 40 fold over the level of complete particles. These impurities can trigger unwanted immune responses in patients. For example, recent studies have shown that cellular immune responses in mice and in human are directed to epitopes in the AAV2 capsids, and the presence of empty capsids inhibits hepatocyte transduction in vivo following high dose vector administration. The potential adverse effects of the unwanted immunogenicity of empty capsids compromise product safety and efficacy.

Removal of empty capsids that have no therapeutic function by known methods is difficult due to the innate similarity of their particle size, affinity and protein composition to the complete particles containing vector DNA. There have been continuous efforts to separate empty AAV capsids from genome containing complete particles. Empty particle-free AAV2 has been achieved by differential $CHCl_3$. However, there may be problems using this method in scale up production and GMP manufacture. Ion exchange chromatography has also been reported for the separation of empty capsids in AAV2, 4, 5 and 8. However, from 20% up to 30 fold empty capsids remained in the final products.

Therefore, there is need to develop new methods of AAV vector production which decrease or eliminate the presence of empty capsids in the final product. This would improve the safety and efficacy of AAV products. Reduction of empty particles would also overcome the hurdle in high titre production.

SUMMARY OF THE INVENTION

Cellular and viral factors that contribute to the formation of two types of particles in AAV vector production are still largely unknown. In general, viruses package their genomes into protein capsids either via association of structural proteins with the viral genome or via insertion of viral genomes into preassembled capsids. AAVs are known to package their genome into preassembled capsids. It has been reported that specific amino acid interactions are required for efficient insertion of viral DNA and single amino acid mutations and gross conformation change of AAV capsid proteins have been shown to result in deficiency of packaging AAV genomes. There have also been very limited studies on the involvement of cellular proteins in AAV assembly, indicating that total producer cell proteins and DNA helicase are necessitated in AAV assembly. However, the actual mechanism by which AAV DNA is inserted into capsids is unknown.

In order to better understand the role of cellular proteins in AAV assembly and, ultimately improve the safety and quality of AAV products, the present inventors have analysed host cellular proteins co-produced and co-purified in AAV vectors. In particular, the present inventors have conducted the first systematic analysis and comparison of the protein composition between empty capsids and complete vectors in three AAV serotypes: AAV2; AAV5; and AAV8. The inventors have demonstrated intrinsic similarity among the three AAV serotypes, although there are some notable differences between the different serotypes. Importantly, the inventors demonstrated for the first time that there are significant differences between empty capsids and complete vectors. Finally, the inventors have identified a number of host cell proteins that are inherently associated with AAV products. In particular, the inventors have demonstrated that host cell proteins YB1, NPM1 and NCL are found in AAV products, and that modulating the expression of these host cell proteins impacts the production of AAV vector particles.

Accordingly, the present invention provides a transgenic producer cell line in which the expression of at least one of YB1, NPM1 and NCL is modulated compared with a control producer cell line. Typically, the expression of: (i) NPM1 and NCL; (ii) YB1 and NPM1; (iii) YB1 and NCL; or (iv) YB1, NPM1 and NCL; is modulated in the producer cell line of the invention compared with a control producer cell line.

In a preferred embodiment, the expression of at least one of YB1, NPM1 and NCL is reduced compared with a control producer cell line, wherein the expression of YB1, NPM1 and/or NCL may be reduced using CRISPR genome editing, a double stranded RNA (dsRNA), a small interfering RNA (siRNA), a small hairpin RNA (shRNA), a micro RNA or an antisense RNA. Typically the expression of YB1, NPM1 and/or NCL is reduced using a shRNA, and preferably: YB1 expression is reduced using a shRNA comprising the nucleotide sequence SEQ ID NOs: 14 to 18 (Y1 to Y5); NPM1 expression is reduced using a shRNA comprising the nucleotide sequence SEQ ID NOs: 4 to 8 (NPM-N6 to NPM-N10); and/or NCL expression is reduced using a shRNA comprising the nucleotide sequence SEQ ID NOs: 9 to 13 (NCL-N1 to NCL-N5). The expression of YB1, NPM1 and/or NCL may be reduced using CRISPR genome editing. In one embodiment, the expression of YB1 is reduced using a gRNA pair selected from SEQ ID NOs: 33 and 34; SEQ ID NOs: 35 and 36; SEQ ID NOs: 37 and 38; and/or SEQ ID NOs: 39 and 40.

The expression of one or more additional genes and/or proteins listed in Table 2 herein may also be modulated in a producer cell line of the invention compared with a control producer cell line.

In a preferred embodiment, the transgenic producer cell line of the invention is a human embryonic kidney 293T cell line.

The invention also provides a method for producing an adeno-associated viral (AAV) vector comprising culturing an adeno-associated virus in a producer cell line in which the expression of at least one of YB1, NPM1 and NCL is modulated.

Typically the expression of: (i) NPM1 and NCL; (ii) YB1 and NPM1; (iii) YB1 and NCL; or (iv) YB1, NPM1 and NCL; in the producer cell line is modulated according to a method of the present invention. Preferably the modulation of YB1, NPM1 and/or NCL expression is a reduction in the expression of YB1, NPM1 and/or NCL, wherein the expression of YB1, NPM1 and/or NCL is reduced using CRISPR genome editing, a double stranded RNA (dsRNA), a small interfering RNA (siRNA), a small hairpin RNA (shRNA), a micro RNA or an antisense RNA. Typically the expression of YB1, NPM1 and/or NCL is reduced using a shRNA, and preferably: YB1 expression is reduced using a shRNA comprising the nucleotide sequence SEQ ID NOs: 14 to 18 (Y1 to Y5); NPM1 expression is reduced using a shRNA comprising the nucleotide sequence SEQ ID NOs: 4 to 8 (NPM-N6 to NPM-N10); and/or NCL expression is reduced using a shRNA comprising the nucleotide sequence SEQ ID NOs: 9 to 13 (NCL-N1 to NCL-N5). The expression of YB1, NPM1 and/or NCL may be reduced using CRISPR genome editing. In one embodiment, the expression of YB1 is reduced using a gRNA pair selected from SEQ ID NOs: 33 and 34; SEQ ID NOs: 35 and 36; SEQ ID NOs: 37 and 38; and/or SEQ ID NOs: 39 and 40.

The expression of one or more of the additional genes and/or proteins listed in Table 2 may also be modulated in the producer cell line used in a method of the present invention.

The method of the invention may increase the titre of AAV vector at least 2 fold compared with the titre of AAV vector produced by a control method, and/or the method of the invention may increase the ratio of complete:empty AAV vector by at least 20% compared with the ratio of complete: empty AAV vector produced by a control method.

In a preferred embodiment, the transgenic producer cell line used in a method of the invention is a human embryonic kidney 293T cell line.

Preferably, the method of the invention produces AAV2, AAV5 and/or AAV8 serotype AAV vectors.

The invention further provides a population of adeno-associated viral (AAV) vectors obtainable from a producer cell line of the invention and/or a method of the invention. Preferably, the ratio of complete:empty AAV vectors in the population of the invention is increased by at least 20% compared the ratio of complete:empty AAV vector in a population produced by a control method. Preferably the AAV vector population of the invention comprises AAV2, AAV5 and/or AAV8 serotype vectors.

BRIEF DESCRIPTION OF THE DRAWINGS

FIG. 14. *Homo sapiens* Y box binding protein 1 (YB1/YBX1) mRNA (SEQ ID NO: 3) and amino acid (SEQ ID NO: 29) sequences.

FIG. 15. *Homo sapiens* nucleophosmin (nucleolar phosphoprotein B23, numatrin, NPM1) (cDNA clone MGC: 22724 IMAGE:4081364), complete cds, mRNA (SEQ ID NO: 1) and amino acid (SEQ ID NO: 27) sequences.

FIG. 16. Human nucleolin gene, complete cds, mRNA (SEQ ID NO: 2) and amino acid (SEQ ID NO: 28) sequences.

DETAILED DESCRIPTION OF THE INVENTION

Adeno-Associated Virus Vectors

Figure 1:
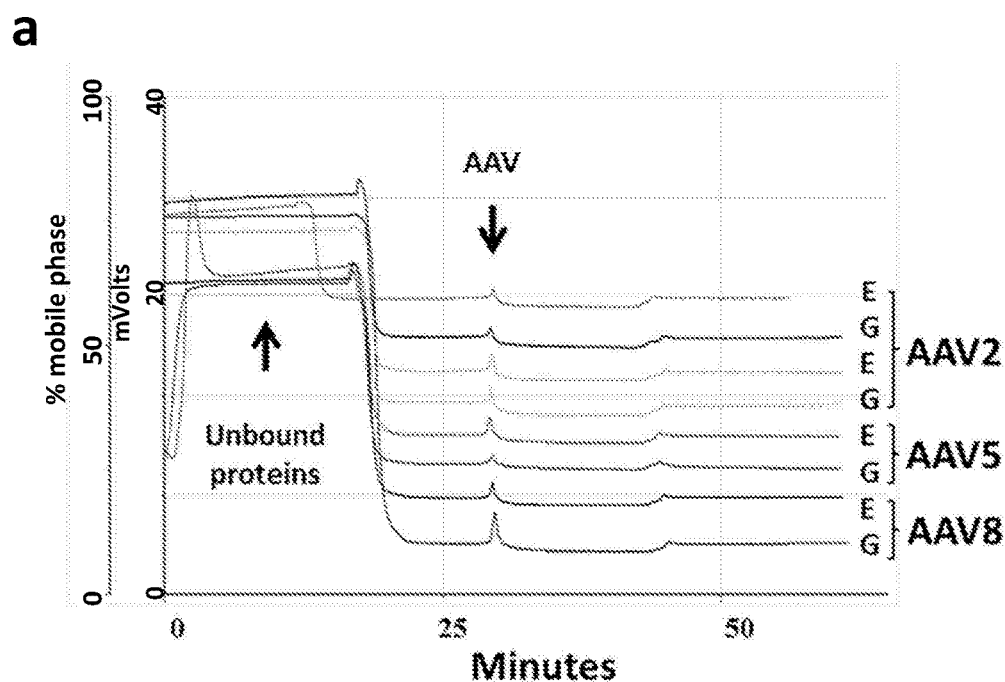
FIG. 1. Protein profile of three serotypes of AAV vectors before and after AVB Sepharose affinity chromatography. (a) A typical chromatography profile, showing the separation of AAV from unbounded cellular proteins; (b) protein profile of silver staining SDS-PAGE showing the purity of AAs vectors before (crude) and after (purified) chromatography. E: empty capsids, G: complete vectors carrying a reporter gene GFP, and AAV capsid proteins VP1, VP2 and VP3.
Figure 1:
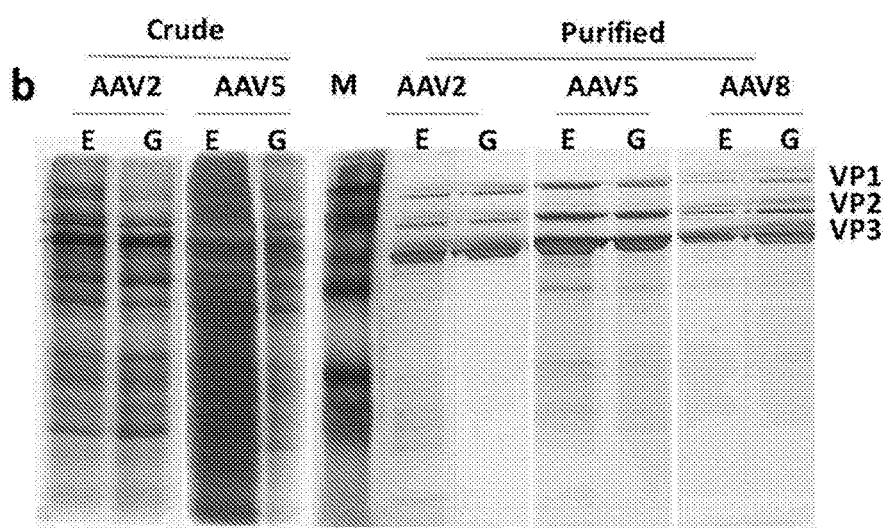

Adeno-associated viruses (AAV) are a family of small viruses which infect humans and some other primate species. AAV belong to the genus *Dependovirus*, of the family Parvoviridae. AAV are small (approximately 20 nm), non-enveloped, replication-deficient viruses. AAV possess a single-stranded linear DNA genomes approximately 4.7 kilobases (kb) in length that may be either positive or negative-sensed.

The AAV genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry.

The genes for the VP1, VP2 and VP3 capsid proteins are generally controlled by a single promoter, designated p40, and all three are translated from a single mRNA. The molecular weights of VP1, VP2 and VP3 are typically about 87, 72 and 62 kiloDaltons (kDa) respectively. The AAV capsid proteins are typically encoded on the AAV DNA genome.

Despite the high seroprevalence of AAV in the human population (approximately 80% of humans are seropositive for AAV2) the virus has not been linked to any human illness. AAV vectors can infect both dividing and quiescent cells. The virus may persist in an extrachromosomal state without integrating into the genome of the host cell. Alternatively, the virus may stably integrate into the host cell genome at a specific site in human chromosome 19 (AAVS1). In contrast to adenoviruses, AAV usually does not trigger an immune response to cells infected with it, and thus can deliver genes to sites of interest, including the brain in the context of gene therapy for diseases of muscle and eye. These features make AAV a very attractive candidate for creating viral vectors for gene therapy, and for developing disease models.

During the process of AAV assembly and production, AAV vectors acquire, inherently and submissively, various cellular proteins, but the identity of these proteins has previously been poorly characterised. The present inventors have, for the first time, identified and characterised host proteins inherently associated with AAV vectors, with the aim of improving the production of AAV vectors for gene therapy. In particular, the present inventors have investigated three serotypes of recombinant AAV, namely AAV2, AAV5 and AAV8 and have demonstrated an important role for NPM1, NCL and YB1 in AAV vector production. Using liquid chromatography-mass spectrometry (LC/MS/MS), the inventors have identified 66 AAV-associated human cellular proteins including NPM1, NCL and YB1. Introducing shRNA sequences for NPM1, NCL and/or YB1 targets and down-regulates the respective genes and increases AAV titres.

As described herein, the present invention provides a new production system for the production of AAV vectors which increase the viral titre produced. The production systems of the invention may also increase the ratio of complete:empty viral vector particles produced. The production systems of the invention comprise producer cell lines adapted for the production of AAV vectors, as well as methods of producing AAV vectors using said producer cell lines.

The present invention also provides AAV vectors produced by said production systems, producer cell lines and methods. Typically, the AAV vectors of the present invention differ from AAV vectors produced by standard methods known in the art, because the AAV vectors of the present invention have a higher titre, improved complete:empty AAV vector ratio and/or a modulated level of cellular proteins, particularly proteins from the producer cell line, in the AAV vector.

According to the present invention, a complete viral vector particle is a viral vector particle which comprises a payload for delivery to an individual. Typically, the payload is a nucleotide sequence as described herein. According to the present invention, an empty viral vector particle is a viral vector particle which lacks said payload. Typically, an empty viral vector particle of the invention is an empty AAV capsid or protein coat.

An AAV vector of the invention may be useful in methods of gene therapy and gene manipulation and modification in many disciplines. The vector may comprise one or more therapeutic nucleotide sequence, which may be in any appropriate form, including single stranded DNA (ssDNA) or self-complementary DNA. For example, an AAV vector of the invention may comprise a therapeutic DNA sequence useful in therapy or prevention of a disease or disorder. An AAV vector of the invention may also be useful in other way, for example in drug development and research. Such non-therapeutic applications include for gene manipulation and delivery, for example to deliver shRNA, oncogenes, etc. to generate induced pluripotent stem cells (IPS).

The AAV vector may be of any AAV serotype. For instance, the AVV vector of the invention may be any one of AAV1, AAV2, AAV3, AAV4, AAV5, AAV6, AAV7, AAV8, AAV9, AAV10 or AAV11. In a preferred embodiment, the AAV vector is selected from AAV2, AAV5 or AAV8. A combination of any two or more AAV serotypes is also provided by the present invention. The combination of AAV serotypes may include AAV2 and AAV5; AAV5 and AAV8; AAV2 and AAV8; or AAV2, AAV5 and AAV8.

The invention also provides a population of adeno-associated viral (AAV) vectors of the invention. In particular, the present invention provides a population of AAV vectors obtainable by a method of the invention as disclosed herein. According to the present invention, a population of AAV vectors may be defined as multiple copies of an AAV of the invention. For example, a population of AAV vectors of the invention may comprise at least $10^9$ vg/ml, at least $10^9$ vg/ml, at least $20^9$ vg/ml, at least $30^9$ vg/ml, at least $40^9$ vg/ml, at least $50^9$ vg/ml, at least $10^{10}$ vg/ml or more AAV vector particles. An AAV population of the invention may comprise of a single type of AAV vector of the invention. For example, the AAV population of the invention may comprise a single serotype of AAV vector, and may comprise a single payload (e.g. one medicine). The AAV population may be produced in one or more batch or one or more production cycle.

The capsid of the AAV vectors of the invention may comprise any combination of the proteins listed in Table 2 herein. Typically, the capsid of the AAV vectors of the invention comprise any combination of YB1, NPM1 and NCL as disclosed herein. Said capsid may also comprise one or more of the genes and/or proteins listed in Table 2 which are shared by four or more of the AAV serotypes investigated. The one or more gene and/or protein may already be known to have a function in AAV, or may have been associated with AAV for the first time herein. Typically the one or more gene and/or protein that is modulated in addition to at least one of YB1, NPM1 and NCL is selected from heterogeneous nuclear ribonucleoprotein K (hn-RNPK), single-stranded DNA binding protein 1, nascent polypeptide-associated complex alpha subunit (CypA), peptidyl-prolyl cis-trans isomerase, alpha-enolase, Annexin A5, RuVB like 1 and like 2.

Any of the disclosure herein in relation to AAV vectors of the present invention may also be applied to an AAV vector population of the invention. For example, in one embodiment of the invention, modulation of one or more gene and/or protein of a producer cell line may increase the ratio of complete:empty AAV vector in an AAV vector population by at least 20%, at least 30%, at least 40%, at least 50%, at least 60%, at least 70%, at least 80%, at least 90%, at least 100%, at least 150%, at least 200% or more. Preferably, modulation of one or more gene and/or protein of a producer cell line increases the ratio of complete:empty AAV vector particles in an AAV vector population of the invention by at least 50%. Any increase in viral titre resulting from the modulation of one or more gene and/or protein may be compared with the viral titre obtained from a control method as described herein. A control method may be any standard method known in the art for producing AAV vectors. For example, a control method may use producer cell lines which have not been adapted according to the present invention. AAV vectors and AAV vector populations produced by such control/standard methods may be used as control vectors and populations as described herein.

Standard methods known in the art can produce AAV vector populations in which up to 100% of the AAV vectors produced are empty, or with 100 fold more empty AAV vectors than complete AAV vectors. Even with further processing, the standard methods produce AAV vector populations in which at least 20% of the AAV vectors are empty. The methods of the present invention may produce AAV vector populations in which at least 50%, at least 60%, at least 70%, at least 80%, at least 85%, at least 90%, at least 95%, at least 96%, at least 97%, at least 98%, at least 99%, up to 100% of the AAV vectors are complete (i.e. less than 50%, less than 40%, less than 30%, less than 20%, less than 15%, less than 10%, less than 5%, less than 4%, less than 3%, less than 2%, less than 1%, up to none of the AAV vectors produced are empty). The methods of the invention may produce AAV vector populations in which there are less than 50-fold, less than 40-fold, less than 30-fold, less than 20-fold, less than 10-fold, or less empty AAV vectors compared with the number of complete AAV vectors.

At least 40%, at least 50%, at least 60%, at least 70%, at least 80%, at least 85%, at least 90%, at least 95%, at least 96%, at least 97%, at least 98%, at least 99%, up to and including all of the AAV vector particles in an AAV vector population of the invention may have a capsid which comprises at least one of the proteins listed in Table 2. Typically, in an AAV vector population of the invention at least 50% of the AAV vector particles have a capsid which comprises at least one of the proteins listed in Table 2. Preferably the at least one protein is a protein one or more of YB1, NPM1 and/or NCL as described herein, more preferably at least 50% of the AAV vector particles have a capsid which comprises YB1, even more preferably at least 50% of the AAV vector particles have a capsid which comprises YB1, NPM1 and NCL.

The amount of at least one of the proteins listed in Table 2 in the capsid of the AAV vectors in an AAV vector or AAV vector population of the invention may be modified compared with the amount of said at least one protein in the capsid of control AAV vectors or in the capsid of AAV vectors in a control AAV vector population. For example, the amount of the at least one proteins may differ by at least 10%, at least 20%, at least 30%, at least 40%, at least 50%, at least 60%, at least 70%, at least 80%, at least 90%, at least 100%, at least 150%, at least 200% or more compared to the amount of the at least one protein in the capsid of control AAV vectors or in the capsid of AAV vectors in a control AAV vector population. This modification may be an increase or a decrease in the at least one protein. When multiple proteins are modified relative to a control, all may be decreased, some may be decreased and others increased, or all may be increased relative to the control.

The presence and/or amount of any of the proteins listed in Table 2 in the capsid of the AAV vectors in an AAV vector population of the invention may be determined and/or quantified, using any standard technique. Any increase in the presence and/or amount of any of the proteins listed in Table 2 resulting from the modulation of one or more gene and/or protein in the producer cell line according to the present invention may be compared with presence and/or amount of any of the proteins listed in Table 2 in the capsids of AAV vectors in an AAV vector population obtained from a control method as described herein.

The AAV vector or AAV vector population of the invention may have a titre that is increased by at least 2 fold, at least 5 fold, at least 10 fold, at least 20 fold, at least 30 fold, at least 40 fold, at least 50 fold, at least 60 fold, at least 70 fold or more compared to a control AAV vector or AAV vector population. Preferably, the titre of the AAV vector or AAV vector population is increased by at least 2 fold, at least 5 fold or at least 10 fold. The AAV vector or AAV vector population titre may be compared with the titre of a control AAV vector or AAV vector population, or with the viral titre obtained from a control method as described herein.

Methods for Producing Adeno-Associated Viral Vectors

The present inventors have shown for the first time that modulating the expression of certain genes and/or proteins in a producer cell line used to produce an AAV vector can have an effect on the titre of viral vector produced from said producer cell line. Modulation of the expression of certain genes and/or proteins in a producer cell line used to produce an AAV vector may also increase the ratio of complete:empty viral vector particles produced from said producer cell line. Modulation of the expression of certain genes and/or proteins in a producer cell line used to produce an AAV vector may also modify the presence and/or amount of the proteins in the AAV vector capsid, particularly proteins derived from the producer cell line.

Modulation of One or More Gene and/or Protein

As described herein, the present invention provides a new production system for the production of AAV vectors which increase the viral titre produced. The production systems of the invention may also increase the ratio of complete:empty viral vector particles produced. The production systems of the invention may also modify the presence and/or amount of the proteins in the AAV vector capsid, particularly proteins derived from the producer cell line. The production systems of the invention comprise producer cell lines adapted for the production of AAV vectors, as well as methods of producing AAV vectors using said producer cell lines. The present invention also provides AAV vectors produced by said production systems, producer cell lines and methods.

Accordingly, the present invention provides a method of producing an AAV vector comprising modulating the expression of one or more genes and/or proteins in a producer cell line.

Modulation may be increasing or reducing (decreasing) the expression of the one or more gene and/or protein. In cases where multiple genes and/or proteins are modulated, all the gene/proteins may be increased, or all the genes/proteins may be decrease, or one or more genes/proteins may be increased and others of the genes/proteins may be decreased. In a preferred embodiment, the modulation is decreasing the expression of the one or more gene and/or protein.

Modulation, whether an increase or a reduction in the expression of one or more gene and/or protein in a producer cell line, may be measured relative to a control. Thus, the expression of one or more gene and/or protein in a producer cell line of the invention may be compared with the expression of said one or more gene and/or protein in a control. The actual amount of the one or more gene and/or protein, such as the mass, molar amount, concentration or molarity of the one or more gene and/or protein in the producer cell line of the invention and the control may be assessed and compared with the corresponding value from the control. Alternatively, the expression of one or more gene and/or protein in a producer cell line of the invention may be compared with that of the control without quantifying the mass, molar amount, concentration or molarity of the one or more gene and/or protein.

Typically the control is an equivalent producer cell line in which no modulation of the one or more gene and/or protein has been effected. For example, in the case where the producer cell line of the invention is a transgenic cell line in which YB1 expression has been reduced, a suitable control would be the same cell line in which YB1 expression has not been altered. Such control cell lines may be wild-type cell lines. A control method according to the present invention typically uses a control producer cell line as described herein. Conventional methods for the production of AVV, including known methods may be considered control methods according to the present invention.

The expression of the one or more gene and/or protein in a producer cell line of the invention may differ by at least 10%, at least 20%, at least 30%, at least 40%, at least 50%, at least 60, at least 70%, at least 80%, at least 90%, at least 100%, at least 150%, at least 200% or more compared with a control.

For example, if the expression of one or more gene and/or protein in a producer cell line of the invention is reduced compared with a control, the expression may be reduced partially or totally compared with the control. Typically the expression is reduced by at least 10%, at least 20%, at least 30%, at least 40%, at least 50%, at least 60, at least 70%, at least 80%, at least 90%, at least 95%, at least 99%, up to total elimination (knockout) of expression of the one or more gene and/or protein.

If the expression of one or more gene and/or protein in a producer cell line of the invention is increased compared with a control, the expression may be increased by at least 10%, at least 20%, at least 30%, at least 40%, at least 50%, at least 60, at least 70%, at least 80%, at least 90&, at least 100%, at least 150%, at least 200% compared with the control.

The expression of one or more gene and/or protein in a producer cell line of the invention may be determined by quantitative and/or qualitative analysis. Typically, gene expression may be expressed in terms of mRNA levels.

The expression level of the one/or more gene and/or protein in a producer cell line of the invention encompasses the mass of the one/or more gene and/or protein, the molar amount of the one/or more gene and/or protein, the concentration of the one/or more gene and/or protein and the molarity of the one/or more gene and/or protein. This expression level may be given in any appropriate units. For example, the concentration of the one or more gene and/or protein may be given in pg/ml, ng/ml or µg/ml.

The expression level of the one/or more gene and/or protein in a producer cell line of the invention may be measured directly or indirectly.

The relative expression of the one or more modulated gene and/or protein in a producer cell line of the invention relative to a control may be determined using any appropriate technique. Suitable standard techniques are known in the art, for example Western blotting and enzyme-linked immunosorbent assays (ELISAs).

The expression level of the one or more gene and/or protein to be modulated may be altered compared with a control for at least 12 hours, at least 24 hours, at least 30 hours, at least 48 hours, at least 72 hours, at least 96 hours, at least 120 hours, at least 144 hours, at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or more.

The expression level of the one or more gene and/or protein to be modulated may be altered compared with a control for at least one, at least two, at least three, at least four, at least five, at least ten, at least 20, at least 30, at least 40 or more passages of the producer cell line in culture. The expression level of the one or more gene and/or protein to be modulated may be altered indefinitely.

Modulated Genes and/or Proteins

The inventors have carried out the first systematic analysis of the non-viral proteins contained in the capsid of AAV, and have identified 66 proteins that are found in the capsid or one or more of AAV serotypes 2, 5 and 8. These proteins are identified herein in Table 2. Typically these non-viral proteins are derived from the producer cell line in which the AAV vector particles are made.

Modulating the expression of one or more of these 66 proteins in a producer cell line may be useful in increasing the titre of AAV vector produced from said producer cell line. Accordingly, the present invention provides a method for producing an AAV vector comprising modulating the expression of at least one of the proteins listed in Table 2.

The methods of the invention may comprise modulating the expression at least one of the proteins listed in Table 2 that is a DNA binding protein. Alternatively or in addition, the methods of the invention may comprise modulating the expression at least one of the proteins listed in Table 2 that is not a DNA binding protein.

The method of the invention may comprise modulating the expression of at least 2, at least 3, at least 4, at least 5, at least 10, at least 20, at least 30, at least 40, at least 50, at least 60, up to all of the genes and/or proteins listed in Table 2.

Of the proteins listed in Table 2, several are known to bind to DNA. For example, NPM1 (also known as nucleophosmin, nucleolar phosphoprotein B23 and numatrin), NCL and YB1 all bind to DNA and/or RNA.

NPM1 is associated with nucleolar ribonucleoprotein structures and binds to both single- and double-stranded DNA. The genomic DNA sequence of the human NPM1 gene is given in SEQ ID NO: 1 (Genbank Accession No. BC016768, version BC016768.1 GI:16876991). NPM1 is generally located in the nucleolus, but can be translocated to the nucleoplasm in some circumstances.

The NCL gene encodes the nucleolar phosphoprotein nucleolin. Nucleolin is a DNA binding protein involved in the synthesis and maturation of ribosomes. Any reference herein to the NCL protein may be understood as a reference to nucleolin. The genomic DNA sequence of the human NCL gene is given in SEQ ID NO: 2 (Genbank Accession No. M60858, version M60858.1 GI:189305).

The YB1 gene encodes the Y box binding protein 1 (also known as Y box transcription factor and nuclease sensitive element binding protein 1). The genomic DNA sequence of the human YB1 gene is given in SEQ ID NO: 3 (Genbank Accession No. NM_004559.3, version NM_004559.3 GI:109134359). Any reference herein to the YB1 protein may be understood as a reference to Y box binding protein 1. YB1 is a DNA and RNA binding protein involved in many DNA and mRNA dependent processes. YB1 packs and stabilises mRNA and is involved in gene regulation at different levels.

Adenoprotein E1B is known to interact with YB1, and has been shown to result in the accumulation of YB1 in cell nuclei and the activation of adenoviral gene E2A. Overexpression of YB1 regulated the adenoviral E2 promoter in an E1-independent manner, and has been shown to increase adenoviral DNA replication and an increase in the production of infectious viral particles from E1-deleted adenoviral vectors. As a result, overexpression of YB1 has been exploited in adenovirus-based vector development and virotherapy.

However, as demonstrated in the Examples herein, the present inventors have found that knockdown of YB1 results in increased AAV vector titres. Further, the present inventors demonstrated that down-regulation of YB1 expression in producer cells resulted in an increase in AAV rep expression, an increase in AAV vector DNA production and a decrease in AAV cap expression. Without wishing to be bound by theory, it is believed that DNA binding proteins, such as YB1, NPM1 and NCL, from a producer cell line compete with adenoviral components for binding to DNA, particularly single-stranded DNA (ssDNA). Such adenoviral components include adenoproteins E2a and E4, which are early function proteins required for viral replication, and VA, which is a region of the adenoviral genome that codes for small RNA molecules which are not translated by which regulate the translation of viral mRNAs for binding to DNA. Open-reading frame 6 of the E4 region is important for the conversion of the single-stranded AAV genome into a double-stranded form which is the substrate for subsequent steps in DNA replication. Protein E2A plays a key role in viral DNA replication via binding to AAV viral DNA, promoting DNA elongation and displacement of the elongating strand from its template.

Adenoviral components such as E2a, E4 and VA are needed for AAV vector particle production, and by competing with these adenoviral components for binding to DNA, producer cell line DNA binding proteins can decrease AAV vector particle production. Consequently, without being bound by theory, decreasing expression of producer cell line DNA binding proteins such as NPM1, NCL and YB1 reduces the competition of these producer cell line DNA binding proteins with E2A binding to AAV DNA, resulting in the enhancement of E2A-AAV DNA interaction, the efficiency of AAV DNA replication and ultimately increase in AAV vector genome titres.

YB1 binding to the ssDNA region of a promoter has been shown to result in the stabilisation of ssDNA that also inhibited gene transcription and translation. Therefore, it is possible that down regulation of YB1 (or another producer cell DNA binding protein such as NPM1 or NCL) promotes E2A binding to the AAV2p5 promoter that synergistically contribute to an increase in AAV2 and AAV8 titres (as observed by the present inventors).

Accordingly, typically the method of the invention comprises modulating the expression of at least one of NPM1, NCL and YB1. Typically the method of the invention comprises modulating the expression of YB1. Methods in which a combination of NPM1, NCL and YB1 are modulated are also encompassed. For example, a method of the invention may comprise modulating the expression of: (i) NPM1 and NCL; (ii) NPM1 and YB1; (iii) NCL and YB1; or (iv) NPM1, NCL and YB1. In a preferred embodiment, the method of the invention comprises modulating the expression of YB1, NPM1 and NCL.

In a preferred embodiment, the method of the invention comprises reducing the expression of at least one of NPM1, NCL and YB1. Typically the method of the invention comprises reducing the expression of YB1. Methods in which a combination of NPM1, NCL and YB1 are reduced are also encompassed. For example, a method of the invention may comprise reducing the expression of: (i) NPM1 and NCL; (ii) NPM1 and YB1; (iii) NCL and YB1; or (iv) NPM1, NCL and YB1. In a preferred embodiment, the method of the invention comprises reducing the expression of YB1, NPM1 and NCL.

The method of the invention may further comprise modulating the expression of one or more additional gene and/or protein in the producer cell line. For example, the method may further comprise modulating the expression of one or more additional protein listed in Table 2 in the producer cell line. The additional protein modulated according to the present invention may be a DNA binding protein. The additional protein modulated according to the present invention may have a function other than DNA binding. Thus, the method of the invention may involve the modulation of two or more genes and/or proteins that have different functions in the producer cell line, at least one of which may be a DNA binding protein. The method of the invention may involve modulating the expression of at least one of NPM1, NCL and YB1 and also the modulation of one or more additional gene and/or protein in the producer cell line, wherein the one or more additional gene and/or protein may be listed in Table 2.

The method of the invention may comprise modulating the expression of any combination of NPM1, NCL and YB1 as disclosed herein, and also modulating the expression of one or more of the genes and/or proteins listed in Table 2. In a preferred embodiment, the one or more gene and/or protein in Table 2 are shared by four or more of the AAV serotypes investigated. The one or more gene and/or protein may already be known to have a function in AAV, or may have been associated with AAV for the first time herein. Typically the one or more gene and/or protein that is modulated in addition to at least one of NPM1, NCL and YB1 is selected from heterogeneous nuclear ribonucleoprotein K (hn-RNPK), single-stranded DNA binding protein 1, nascent polypeptide-associated complex alpha subunit (CypA), peptidyl-prolyl cis-trans isomerase, alpha-enolase, Annexin A5, RuVB like 1 and like 2.

The one or more gene and/or protein to be modulated according to the present invention may be modulated by any appropriate means. Suitable standard techniques are known in the art. Modulation may take place via any suitable mechanism, depending for example on the nature (see below) of the modulator used, e.g. steric interference in any direct or indirect interaction or modulation of the one or more gene and/or protein.

Modulators of the invention may be specific for a gene or protein to be modulated. By specific, it will be understood that the modulator binds to a gene or protein to be modulated, such as the YB1, NPM1 or NCL gene, with no significant cross-reactivity to any other molecule, particularly any other protein. For example, modulator that is specific for NPM1 will show no significant cross-reactivity with human neutrophil elastase. Cross-reactivity may be assessed by any suitable method. Cross-reactivity of modulator for a gene or protein to be modulated with a molecule other that gene or protein may be considered significant if the modulator binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the gene or protein to be modulated. A modulator that is specific for a gene or protein to be modulated may bind to another molecule such as human neutrophil elastase at less than 90%, 85%, 80%, 75%, 70%, 65%, 60%, 55%, 50%, 45%, 40%, 35%, 30%, 25% or 20% the strength that it binds to the gene or protein to be modulated. Preferably, the modulator binds to the other molecule at less than 20%, less than 15%, less than 10% or less than 5%, less than 2% or less than 1% the strength that it binds to the gene or protein to be modulated.

Any suitable modulator may be used according to the invention, for example peptides and peptidomimetics, antibodies, small molecule inhibitors, double-stranded RNA, antisense (single stranded) RNA, aptamers and ribozymes. Transcriptional and post-transcriptional gene silencing technologies may be used to modulate one or more gene of the invention. Post-transcriptional gene silencing is also known as RNA interference (RNAi). In a preferred embodiment, modulation is carried out by Clustered Regularly Interspaced Short Palindromic Repeats (CRISPR) genome editing, which is typically used to decrease expression of the one or more genes of the invention. Preferred antagonists include double-stranded RNA and chimeric guide RNA transcripts (gRNA). gRNA combines bacterial CRISPR RNA (crRNA) and trans-activating crRNA (tracrRNA) which are recruited to a gene of interest during CRISPR genome editing, together with an endonuclease (typically a CRISPR associated nuclease (Cas), such as Cas9). The one or more genes of the invention may be modulated using the same category of modulator, or by different modulators. As a non-limiting example, YB1, NPM1 and/or NCL may all be modulated using CRISPR genome editing; or YB1 may be modulated by CRISPR genome editing and NPM1 and/or NCL may be modulated using shRNA.

Double-Stranded RNA

Double-stranded RNA (dsRNA) molecules may be used to modulate expression of one or more gene in a producer cell line. Typically, dsRNAs are used to reduce expression of the one or more gene as described herein. dsRNA molecules may be used in RNAi to modulate one or more gene of the invention.

Using known techniques and based on a knowledge of the sequence of the one or more gene to be modulated, dsRNA molecules can be designed to antagonise the one or more gene by sequence homology-based targeting of the corresponding RNA sequence. Such dsRNAs will typically be small interfering RNAs (siRNAs), small hairpin RNAs (shRNAs), or micro-RNAs (miRNAs). The sequence of such dsRNAs will comprise a portion that corresponds with that of a portion of the mRNA encoding the one or more gene to be modulated. This portion will usually be 100% complementary to the target portion within the mRNA transcribed from the one or more gene, but lower levels of complementarity (e.g. 90% or more or 95% or more) may also be used. Typically the % complementarity is determined over a length of contiguous nucleic acid residues. A dsRNA molecule of the invention may, for example, have at least 80% complementarity to the target portion within the mRNA transcribed from the one or more gene measured over at least 10, at least 20, at least 30, at least 40, at least 50, at least 60, at least 70, at least 80, at least 90, or more nucleic acid residues, up to the dsRNA molecule having at least 80% complementarity the mRNA transcribed from the one or more gene of the invention over the entire length of the dsRNA molecule.

In a preferred embodiment, the dsRNA is a shRNA. ShRNA can be delivered to a producer cell line of the invention by any appropriate means. Suitable techniques are known in the art and include the use of plasmid, viral and bacterial vectors to deliver the shRNA to the producer cell line. Typically, the shRNA is delivered using a viral vector delivery system. In a preferred embodiment, the viral vector is a lentiviral vector.

Generally, once the shRNA has been delivered to a producer cell, it is then transcribed in the nucleus and processed. The resulting pre-shRNA is exported from the nucleus and then processed by dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing.

shRNA is used to modulate the expression of one or more of the genes listed in Table 2. Multiple shRNAs may be used to modulate the expression of any one of the genes listed in Table 2. Typically, shRNA is used to modulate the expression of at least one of YB1, NPM1 and/or NCL and/or YB1. Multiple shRNAs may be used to modulate the expression of YB1, NPM1 and/or NCL.

The shRNA used to modulate YB1 expression may comprise a nucleotide sequence selected from SEQ ID NOs: 14 to 18 (YB1-Y1 to YB1-Y5), or a variant thereof. Multiple shRNAs selected from SEQ ID NOs: 14 to 18, or a variant thereof, may be used to modulate YB1 expression. In a preferred embodiment, the shRNA used to modulate YB1 expression is SEQ ID NO: 17 and/or 18 (YB1-Y4 and Y5) or a variant thereof.

The shRNA used to modulate NPM1 expression may comprise a nucleotide sequence selected from SEQ ID NOs: 4 to 8 (NPM-N6 to NPM-N10), or a variant thereof. Multiple shRNAs selected from SEQ ID NOs: 4 to 8, or a variant thereof, may be used to modulate NPM1 expression. In a preferred embodiment, the shRNA used to modulate NPM1 expression is SEQ ID NO: 4 and/or 7 (NPM-N6 and N9) or a variant thereof.

The shRNA used to modulate NCL expression may comprise a nucleotide sequence selected from SEQ ID NOs: 9 to 13 (NCL-N1 to NCL-N5), or a variant thereof. Multiple shRNAs selected from SEQ ID NOs: 9 to 13, or a variant thereof, may be used to modulate NCL expression. In a preferred embodiment, the shRNA used to modulate NCL expression is SEQ ID NO: 9 and/or 12 (NCL-N1 and N4) or a variant thereof.

The sequences of NPM-N6 to N10, NCL-N1 to N5 and YB1-Y1 to Y5 (SEQ ID NOs: 4 to 18) are shown in Table 1 below.

Any combination of the shRNAs of SEQ ID NOs: 14 to 18 (YB1-Y1 to YB1-Y5), SEQ ID NOs: 4 to 8 (NPM-N6 to NPM-N10) and SEQ ID NOs: 9 to 13 (NCL-N1 to NCL-N5), or variants thereof, may be used.

A variant sequence may have at least 80% sequence identity to a sequence of the invention, measured over any appropriate length of sequence. Typically the % sequence identity is determined over a length of contiguous nucleic acid or amino acid residues. A variant sequence of the invention may, for example, have at least 80% sequence identity to a sequence of the invention measured over at least 10, at least 20, at least 30, at least 40, at least 50, at least 60, at least 70, at least 80, at least 90, or more nucleic acid or amino acid residues.

For example, a variant shRNA molecule of the invention may have at least 80% sequence identity with an shRNA molecule of the invention measured over at least 10, at least 20, at least 30, at least 40, at least 50, at least 60 or more nucleic acid residues, up to the variant shRNA molecule having at least 80% sequence identity with the shRNA molecule of the invention over the entire length of the variant shRNA molecule. Typically the variant shRNA molecule of the invention is a variant of one or more of the shRNA molecules of SEQ ID NOs: 4 to 18.

CRISPR Genome Editing

The Clustered Regularly Interspaced Short Palindromic Repeats (CRISPR) system for genome editing typically comprises two distinct components: (1) a guide RNA and (2) an endonuclease, specifically a CRISPR associated (Cas) nuclease, such as Cas9. The guide RNA is a combination of the endogenous bacterial crRNA and tracrRNA into a single chimeric guide RNA (gRNA) transcript. When the gRNA and the Cas are expressed in the cell, the genomic target sequence can be modified or permanently disrupted.

The gRNA/Cas complex is recruited to the target sequence by the base-pairing between the gRNA sequence and the complement to the target sequence in one or more gene of the invention in the genomic DNA. For successful binding of Cas, the genomic target sequence must also contain the correct Protospacer Adjacent Motiff (PAM) sequence immediately following the target sequence. The binding of the gRNA/Cas complex localises the Cas to the genomic target sequence in the one or more gene of the invention so that the wild-type Cas can cut both strands of DNA causing a double strand break. This can be repaired through one of two general repair pathways: (1) the non-homologous end joining DNA repair pathway or (2) the homology directed repair pathway. The non-

TABLE 1

Sequences of exemplary shRNA molecules of the invention

| Gene | shRNA designation | SEQ ID NO: | Sequence(5'-3') |
|---|---|---|---|
| NPM1 | NPM-N6 | 4 | CCGGGCCAAGAATGTGTTGTCCAAACTCGAGTTTGGACAACACATTCTTGGCTTTTTG |
|  | NPM-N7 | 5 | CCGGGCGCCAGTGAAGAAATCTATACTCGAGTATAGATTTCTTCACTGGCGCTTTTTG |
|  | NPM-N8 | 6 | CCGGGCAAAGGATGAGTTGCACATTCTCGAGAATGTGCAACTCATCCTTTGCTTTTTG |
|  | NPM-N9 | 7 | CCGGCCTAGTTCTGTAGAAGACATTCTCGAGAATGTCTTCTACAGGAACTAGGTTTTTG |
|  | NPM-N10 | 8 | CCGGCGTAGTTCTGTAGAAGACATTCTCGAGAATGTCTTCTACAGAACTAGGTTTTTG |

TABLE 1-continued

Sequences of exemplary shRNA molecules of the invention

| Gene | shRNA designation | SEQ ID NO: | Sequence (5'-3') |
|---|---|---|---|
| NCL | NCL-N1 | 9 | CCGGCCTTGGAAATCCGTCTAGTTACTCGAGTAACTAGACGGATTTCCAAGGTTTTTG |
|  | NCL-N2 | 10 | CCGGCCGGTGAAATTGATGGAAATAACTCGAGTTATTTCCATCAATTTCACCGTTTTTG |
|  | NCL-N3 | 11 | CCGGCGGTGAAATTGATGGAAATAACTCGAGTTATTTGGATCAATTTCACCGTTTTTG |
|  | NCL-N4 | 12 | CCGGAGTAAAGGGATTGCTTATATTCTCGAGAATATAAGCAATCCCTTTACTTTTTTG |
|  | NCL-N5 | 13 | CCGGCGTTCGGGGCAAGGATAGTTACCTCGAGGTAACTATCCTTGCCCGAACGTTTTTG |
| YB1 | YB-Y1 | 14 | CCGGGCAGTTGAAGGGAGTAAATATCTCGAGATATTTAGTGCCTTGAACTGGTTTTTG |
|  | YB-Y2 | 15 | CCGGAGCAGACCGTAACCATTATAGCTCGAGCTATAATGGTTACGGTCTGCTTTTT |
|  | YB-Y3 | 16 | CCGGGCTTACCATCTCTACCATCATCTCGAGATGATGETAGAGATGETAAGCTTTTT |
|  | YB-Y4 | 17 | CCGGGACGGCAATGAAGAAGATAAACTCGAGTTTATCTTCTTGATTGCCGTGTTTTT |
|  | YB-Y5 | 18 | CCGGCCAGTTCAAGGCAGTAAATATCTCGAGATATTTACTGCCTTGAACTGGTTTTT |
| Annexin A5 | A-A1 | 19 | CCGGGCCATCAAACAAGTATGAACTCGAGTTCATAAACTTGTTTGATGGCTTTTT |
|  | A-A2 | 20 | CCGGGCTGGAATTGATGAAGCTCAACTCGAGGAGCTTCATCAACCAGCTTTTT |
|  | A-A3 | 21 | CCGGCCATGATTAAGGGAGATACATCTCGAGATGTATCTCCCAATCATGGTTTTT |
|  | A-A4 | 22 | CCGGCGCGAGACTTCTGGCAATTTACTCGAGTAAATTGCCAGAAGTCTCGCGTTTTT |
|  | A-A5 | 23 | CCGGGCATCCTGACTCTGTTGACATCTCGAGATGTCAACAGAGTCAGGATGCTTTTT | homologous repair pathway often results in inserts/deletions at the double strand break that can lead to frameshifts and/or premature stop codons, effectively disrupting the open reading frame of the one or more gene of the invention. The homology directed repair pathway requires the presence of a repair template, which is used to fix the double strand break.

Any appropriate gRNA pair may be used for CRISPR genome editing according to the present invention, provided it modulates one or more gene of the invention as described herein. Typically gRNA pairs are used to reduce expression of one or more gene of the invention as described herein. Preferably any appropriate gRNA pair is used to modulate (typically reduce, preferably eliminate/knockout) expression of YB1, NPM1 and/or NCL, more preferably YB1.

gRNA pairs can be designed using known techniques and based on a knowledge of the sequence of the one or more gene to be modulated, typically using an appropriate computer programme, such as the CRISPR/Cas9 programme (chopchop.rc.fas.harvard.edu/). For example, gRNAs for modulating YB1 may be designed using the CRISPR/Cas9 programme (chopchop.rc.fas.harvard.edu/) and targeting the entire *Homo sapiens* chromosome 1 sequence (Accession number NC_000001.11) that includes YB1 gene sequence. Knock out producer cells may be generated using any appropriate technique, with standard techniques being known in the art and suitable kits being commercially available.

gRNA pairs can be delivered to a producer cell line of the invention by any appropriate means. Suitable techniques are known in the art and include the use of plasmid, viral and bacterial vectors to deliver the gRNA pairs to the producer cell line. Typically, a gRNA pair is delivered using a plasmid DNA.

gRNA pairs may be used to modulate the expression of one or more of the genes listed in Table 2. Multiple gRNA pairs may be used to modulate the expression of any one of the genes listed in Table 2. Typically, gRNA pairs are used to modulate the expression of at least one of YB1, NPM1 and/or NCL and/or YB1. Multiple gRNA pairs may be used to modulate the expression of YB1, NPM1 and/or NCL.

The gRNA pairs used to modulate YB1 expression may comprise a nucleotide sequence pairs selected from SEQ ID NOs: 33 and 34; SEQ ID NOs: 35 and 36; SEQ ID NOs: 37 and 38; and/or SEQ ID NOs: 39 and 40, or variants thereof. Multiple gRNA pairs selected from SEQ ID NOs: 33 and 34; SEQ ID NOs: 35 and 36; SEQ ID NOs: 37 and 38; and SEQ ID NOs: 39 and 40, or variants thereof, may be used to modulate YB1 expression.

A variant sequence may have at least 80% sequence identity to a sequence of the invention, measured over any appropriate length of sequence. Typically the % sequence identity is determined over a length of contiguous nucleic acid or amino acid residues. A variant gRNA sequence of the invention may, for example, have at least 80% sequence identity to a sequence of the invention measured over at least 10, at least 11, at least 12, at least 13, at least 14, at least 15, at least 16, at least 17, at least 18, at least 19, at least 20, at least 21, at least 22, at least 23, at least 24, or more nucleic acid residues, up to the variant gRNA molecule having at least 80% sequence identity with the shRNA molecule of the invention over the entire length of the variant gRNA molecule. Typically a variant gRNA molecule of the invention is a variant of one or more of the gRNA molecules of SEQ ID NOs: 33 to 40. gRNA pairs of the invention may comprise a variant of one or both of the gRNA sequences disclosed herein. For example, a variant of the gRNA pair of SEQ ID NOs: 33 and 34 may comprise a variant of SEQ ID NO: 33, a variant of SEQ ID NO: 34 or a variant of SEQ ID NOs: 33 and 34. This principle applies to all gRNA pairs disclosed herein.

Antisense RNA

Single-stranded DNA (ssDNA) molecules, also known as antisense RNA, may be used to modulate expression of one or more gene in a producer cell line. Typically, antisense RNAs are used to reduce expression of the one or more gene as described herein.

Using known techniques and based on a knowledge of the sequence of the one or more gene to be modulated, antisense RNA molecules can be designed to antagonise the one or more gene by sequence homology-based targeting of the corresponding RNA. The sequence of such antisense will comprise a portion that corresponds with that of a portion of the mRNA transcribed from the one or more gene. This portion will usually be 100% complementary to the target portion within the transcribed mRNA but lower levels of complementarity (e.g. 90% or more or 95% or more) may also be used.

Aptamers

Aptamers are generally nucleic acid molecules that bind a specific target molecule. Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

As used herein, "aptamer" refers in general to a single or double stranded oligonucleotide or a mixture of such oligonucleotides, wherein the oligonucleotide or mixture is capable of binding specifically to a target. Oligonucleotide aptamers will be discussed here, but the skilled reader will appreciate that other aptamers having equivalent binding characteristics can also be used, such as peptide aptamers.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by Exponential enrichment (SELEX) procedure. SELEX is a method for the in vitro evolution of nucleic acid molecules with highly specific binding to target molecules. It is described in, for example, U.S. Pat. No. 5,654,151, U.S. Pat. No. 5,503,978, U.S. Pat. No. 5,567,588 and WO 96/38579.

The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Variant Nucleic Acid Sequences

A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every nucleic acid sequence presented herein and/or to each and every SEQ ID NO presented herein).

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van Walle et al., Align-M—A New Algorithm for Multiple Alignment of Highly Divergent Sequences, 20 (9) Bioinformatics:1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992.

Variants of the specific sequences provided above may alternatively be defined by reciting the number of nucleotides that differ between the variant sequences and the specific reference sequences provided above. Thus, in one embodiment, the sequence may comprise (or consist of) a nucleotide sequence that differs from the specific sequences provided above at no more than 5, no more than 4, no more than 3, no more than 2 nucleotide positions, for example at no more than 1 nucleotide position. Conservative substitutions are preferred.

The variant nucleic acid molecules of the invention, such as the variant shRNA molecules and/or variant gRNA molecules and/or variant gRNA pairs of the invention typically still retain the activity of the corresponding molecules of the invention. Thus, for example, the variant shRNA molecules of the invention retain the ability of the corresponding shRNA molecules to modulate the expression of the one or more gene of the invention. The variant shRNA molecules may retain at least 50%, at least 60%, at least 70%, at least 80%, at least 90%, up to and including 100% of the modulatory activity of the shRNA molecules of the invention. This applies equally to the gRNA molecules and/or gRNA pairs of the invention.

The nucleic acid molecules of the invention, such as the shRNA molecules, gRNA molecules and/or gRNA pairs of the invention may be labelled (or tagged) in order to facilitate the removal of producer cells lacking the shRNA molecules, gRNA molecules and/or gRNA pairs. Puromycin is an example of a suitable tag. The two gRNA molecules making up a gRNA pair of the invention may be labelled with the same tag. Alternatively, two gRNA molecules making up a gRNA pair of the invention may be labelled with different tags to enable the two gRNA molecules to be distinguished.

Effect of Modulation

Modulators of the invention can increase or reduce the expression of one or more gene and/or protein of a producer cell line. Typically the one or more gene and/or protein is listed in Table 2 as disclosed herein. Typically the modulation of the one or more gene and/or protein of a producer cell line will result in an increase titre of AAV vector production by the producer cell line according to the present invention.

Modulation of one or more gene and/or protein of a producer cell line may increase the titre of AAV vector production by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 55 fold, at least 60 fold, at least 65 fold, at least 70 fold or more. Preferably, modulation of one or more gene and/or protein of a producer cell line increases the titre of AAV vector production by at least 2 fold, at least 5 fold or at least 10 fold. Any increase in viral titre resulting from the modulation of one or more gene and/or protein may be compared with the viral titre obtained from a control method as described herein.

Modulation of one or more gene and/or protein of a producer cell line may increase the titre of AAV vector production for at least 5 days, at least 10 days, at least 20 days, at least 30 days, at least 40 days, at least 50 days, at least 60 days, at least 70 days, at least 80 days, at least 90 days, at least 100 days or more. Preferably, modulation of one or more gene and/or protein of a producer cell line increases the titre of AAV vector production for at least 40 days. Again, the duration of the increased viral titre may be compared with a control, as described herein.

Modulation of one or more gene and/or protein of a producer cell line may increase the titre of AAV vector production for at least one, at least two, at least three, at least four, at least five, at least ten, at least 20, at least 30, at least 40 or more passages of the producer cell line in culture.

Modulation of one or more gene and/or protein of a producer cell line may increase the titre of AAV vector production indefinitely.

There may be a time and dose dependence of the modulation of the one or more gene and/or protein on viral titre. Typically, even at a low dose and early time point, it may be possible to achieve a significant fold increase in AAV vector titre of at least 2 fold, at least 5 fold or at least 10 fold (see, for example, FIG. 6B).

The increase in AAV vector titre may be measured using any appropriate technique. Standard techniques for measuring viral titres are known in the art, for example, using cell based assay, e.g. a plaque assay and/or quantitative PCR (qPCR).

The modulation of the one or more gene and/or protein of the producer cell line may increase the ratio of complete:empty AAV vector produced by the producer cell line according to the present invention. The increase in AAV vector titre and/or the increase in the ratio of complete:empty AAV vector may be compared with a control as described herein.

Modulation of one or more gene and/or protein of a producer cell line may increase the ratio of complete:empty AAV vector produced by the producer cell line by at least 10%, at least 20%, at least 30%, at least 40%, at least 50%, at least 60%, at least 70%, at least 80%, at least 90%, at least 100%, at least 150%, at least 200% or more. Preferably, modulation of one or more gene and/or protein of a producer cell line increases the ratio of complete:empty AAV vector produced by the producer cell line by at least 50%.

Modulation of one or more gene and/or protein of a producer cell line may increase the ratio of complete:empty AAV vector produced by the producer cell line such that the AAV vector population comprises less than 50-fold, less than 40-fold, less than 30-fold, less than 20-fold, less than 10-fold, or less empty AAV vectors compared with the number of complete AAV vectors.

Any increase in viral titre resulting from the modulation of one or more gene and/or protein may be compared with the viral titre obtained from a control method as described herein.

Modulation of one or more gene and/or protein of a producer cell line may increase the ratio of complete:empty AAV vector produced by the producer cell line for at least 5 days, at least 10 days, at least 20 days, at least 30 days, at least 40 days, at least 50 days, at least 60 days, at least 70 days, at least 80 days, at least 90 days, at least 100 days or more. Preferably, modulation of one or more gene and/or protein of a producer cell line increases the ratio of complete:empty AAV vector produced by the producer cell line for at least 40 days. Again, the duration of the increased viral titre may be compared with a control, as described herein.

Modulation of one or more gene and/or protein of a producer cell line may increase the ratio of complete:empty AAV vector produced by the producer cell line for at least one, at least two, at least three, at least four, at least five, at least ten, at least 20, at least 30, at least 40 or more passages of the producer cell line in culture.

Modulation of one or more gene and/or protein of a producer cell line may increase the ratio of complete:empty AAV vector produced by the producer cell line indefinitely.

The ratio of complete:empty AAV vector produced by the producer cell line may be measured using any appropriate technique. Standard techniques for measuring viral titres are known in the art. For example, a combination of qPCR and ELISA may be used to quantify the ratio of complete:empty AAV vector.

Modulation of one or more gene and/or protein of a producer cell line may independently increase AAV rep expression, increase AAV vector DNA production and/or decrease AAV cap expression. Typically the change in AAV rep expression, increase AAV vector DNA production and/or decrease AAV cap expression is at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 20 fold, at least 25 fold, at least 30 fold, at least 35 fold, at least 40 fold, at least 45 fold, at least 50 fold, at least 55 fold, at least 60 fold, at least 65 fold, at least 70 fold or more compared with a control cell line or method as defined herein.

Modulation of one or more gene and/or protein of a producer cell line may independently increase AAV rep expression, increase AAV vector DNA production and/or decrease AAV cap expression for at least 5 days, at least 10 days, at least 20 days, at least 30 days, at least 40 days, at least 50 days, at least 60 days, at least 70 days, at least 80 days, at least 90 days, at least 100 days or more. Preferably, modulation of one or more gene and/or protein of a producer cell line independently increases AAV rep expression, increases AAV vector DNA production and/or decreases AAV cap expression for at least 40 days. Again, the duration of the effect may be compared with a control, as described herein.

Modulation of one or more gene and/or protein of a producer cell line may independently increase AAV rep expression, increase AAV vector DNA production and/or decrease AAV cap expression for at least one, at least two, at least three, at least four, at least five, at least ten, at least 20, at least 30, at least 40 or more passages of the producer cell line in culture.

Modulation of one or more gene and/or protein of a producer cell line may independently increase AAV rep expression, increase AAV vector DNA production and/or decrease AAV cap expression indefinitely.

There may be a time and dose dependence of the modulation of the one or more gene and/or protein on AAV rep expression, AAV vector DNA production and/or AAV cap expression. Typically, even at a low dose and early time point, it may be possible to achieve a significant fold effect on AAV rep expression, AAV vector DNA production and/or AAV cap expression.

The increase AAV rep expression, increase AAV vector DNA production and/or decrease AAV cap expression may be measured using any appropriate technique. Standard techniques for measuring viral titres are known in the art.

Modulation of one or more gene and/or protein of a producer cell line may independently increase AAV rep expression, increase AAV vector DNA production and/or decrease AAV cap expression by at least 10%, at least 20%, at least 30%, at least 40%, at least 50%, at least 60%, at least 70%, at least 80%, at least 90%, at least 100%, at least 150%, at least 200% or more. Preferably, modulation of one or more gene and/or protein of a producer cell line independently increases AAV rep expression, increases AAV vector DNA production and/or decreases AAV cap expression by at least 50%.

Production of the AAV Vector

As described herein, the present invention provides a producer cell line in which the expression of one or more gene and/or protein listed in Table 2 is modulated compared with a control.

In a preferred embodiment, modulation of the one or more gene and/or protein is achieved by shRNA or CRISPR genome editing. If shRNA is used, typically the shRNA is tagged to facilitate removal of producer cells lacking the shRNA. If CRISPR genome editing is used, PCR primers can be designed which can generate two products (bands) due to the cleavage of gDNA in the positive knockout cells compared to the single PCR product/band in the non-cleaved/non-gRNA editing control cells. Again, this facilitates removal of producer cells in which the one or more gene of the invention is not modulated.

Once such a producer cell line of the invention has been established, it may be used to produce AAV vectors according to the present invention. Any appropriate technique may be used to generate AAV vectors according to the present invention. Standard techniques are known in the art.

The AAV vectors of the present invention may be engineered to carry any therapeutic polynucleotide for delivery and expression to a target cell or target cells. The therapeutic polynucleotide may be engineered into various sites within the AAV vectors, including but not limited to, the E1 region, the E2 region, the E3 region and the E4 region, using techniques that are well known to those skilled in the art (Current Protocols in Molecular Biology, Ausubel, F. et al., eds., Wiley and Sons, New York, 1995). The therapeutic polynucleotide cloned into the AAV vector may be engineered as a complete transcriptional unit, including a suitable promoter and polyadylation signal.

Thus, the AAV vectors of the present invention may comprise a therapeutic polynucleotide gene and a promoter between a pair of AAV-derived terminal repeats. The combination of a promoter and therapeutic polynucleotide is also referred to herein as a cassette.

The promoter sequence is operably linked to the therapeutic polynucleotide in a manner to effect expression of the gene. Hence, the promoter sequence can be at either or both ends of the therapeutic polynucleotide. Furthermore, more than one promoter and therapeutic polynucleotide can be present in one AAV vector, i.e. there can be two or more cassettes between the terminal repeats. Accordingly, more than one heterologous gene can be expressed by one vector.

Any promoter may be used in the AAV vector of the invention, provided the promoter is capable of driving expression of the therapeutic polynucleotide when they are operably linked. Such promoters are known in the art, including the AAV E1 promoter or E4 promoter, for example, as well as others including, but not limited to, the CMV promoter and the PGK promoter. The promoter may be tissue or cell preferred or specific, meaning that it drives expression of the therapeutic polynucleotide in either a particular tissue or cell type of interest. Again, such promoters are known in the art.

Suitable polyadenylation signals at the 3' end of the therapeutic polypeptide include, but are not limited to, the AAV polyadenylation signals. The E3 region of the AAV genome may be deleted in order to increase the cloning capacity of a vector, or it may be left in the vector construct.

The AAV vector of the invention typically comprises: 1) the terminal repeats mediate stable, site-specific integration into the cellular genome of an individual to be treated; and 2) the promoter mediates expression of a therapeutic polynucleotide, or the promoter mediates transcription of an antisense RNA or a sense RNA encoding a polypeptide of interest.

The AAV vectors of the present invention can be constructed by a variety of standard methods known in the art, and the order of the ligation of the elements can be varied. A promoter and therapeutic polynucleotide may be ligated together to provide a cassette which can be inserted between two AAV inverted terminal repeats (ITRs). Standard techniques for the construction of AAV vectors of the invention are known in the art and can be found in references such as Sambrook et al. (1989: Molecular Cloning: A Laboratory Manual, Cold Spring Harbor, N.Y.), or any of the myriad of laboratory manuals on recombinant DNA technology that are widely available. A variety of strategies are available for ligating fragments of DNA, the choice of which depends on the nature of the termini of the DNA fragments and can be readily determined.

For example, standard techniques for producing AAV vectors according to the present invention include the transfection of DNA plasmid(s) into the producer cells to express AAV Capsid and Rep proteins; the co-transfection of a DNA plasmid to express a AAV vector genome that is in the forms of single stranded DNA or self-complementary DNA and comprises two AAV inverted terminal repeats (ITR) derived from any AAV serotypes flanking a therapeutic and/or reporter gene(s) to exert biological or therapeutic functions in recipient cells or patients; and with or without (i.e. in a helper-free system) the introduction, via plasmid DNA co-transfection or virus infection, of the AAV helper element(s) from a AAV helper virus, e.g. Adenovirus and Herpes simplex virus.

Other nucleotide sequence elements which facilitate integration of DNA into chromosomes, expression of the DNA, and cloning of the vector may be included in the AAV vector of the invention. For example, the presence of enhancers upstream of the promoter or terminators downstream of the therapeutic polynucleotide can facilitate expression.

As disclosed herein, the AAV vectors of the invention also comprise AAV capsid proteins. Typically, these AAV capsid proteins are designated VP1, VP2 and VP3. These AAV capsid proteins are typically encoded on the AAV DNA genome, enabling the production of assembled AAV viral particles.

Producer Cell Lines

According to the present invention, a producer cell line may be defined as a cell line capable of replicating and packaging an AAV vector. Any appropriate producer cell line may be modified and used according to the present invention. A producer cell line of the invention is a eukaryotic cell line, and typically a mammalian cell line. The AAV vectors produced by the present invention are usually intended for therapy in humans. Therefore, preferably a producer cell line of the invention is a human cell line. A producer cell line of the invention may be selected from NIH3T3, HT1080, A549, HeLa cells, and HEK 293T cell lines. A producer cell line of the invention may be in an adherent or suspension form.

In a preferred embodiment, the producer cell line is the human embryonic kidney (HEK) 293T cell line. The HEK293T cell line expresses the SV40 early region under the transcriptional control of the Rous sarcoma virus long terminal repeat promoter.

As referred to herein, a control producer cell line is one which has not been modified or adapted according to the present invention.

Therapeutic Applications

The AAV vectors of the invention may be used as gene therapy vectors. Gene therapy involves the transfer and insertion of new genetic information into cells. The genetic information may be transiently or stably inserted into cells. The AAV vectors of the present invention are safe for gene therapy. Thus, the AAV vectors of the present invention may be capable of site-specific integration into a mammalian chromosome without substantial cytotoxicity, and which direct host cell-specific expression of a therapeutic polynucleotide. Preferably the AAV vectors of the invention are used in gene therapy in mammals, more preferably humans.

The AAV vectors of the invention may comprise any polynucleotide which can be used to treat or prevent a disease or condition. The therapeutic polynucleotide may be DNA or RNA. Typically the therapeutic polynucleotide is DNA. The therapeutic polynucleotide is preferably a biologically functional gene which targets (replaces) a non-functional and/or mutated gene in the individual to be treated. In preferred embodiments, when the individual to be treated is human, the therapeutic polynucleotide is also human.

The therapeutic polynucleotide may encode a biologically functional protein, i.e. a polypeptide or protein which affects the cellular mechanism of a cell in which the biologically functional protein is expressed. For example, the biologically functional protein can be a protein which is essential for normal growth of the cell or for maintaining the health of an individual. The biologically functional protein can also be a protein which improves the health of an individual by either supplying a missing protein, by providing increased quantities of a protein which is under-produced in the individual or by providing a protein which inhibits or counteracts an undesired molecule which may be present in the individual. The biologically functional protein can also be a protein which is a useful protein for investigative studies for developing new gene therapies or for studying cellular mechanisms.

The biologically functional protein can be a protein which is essential for normal growth or repair of the body. The biologically functional protein may also be one which is useful in fighting diseases such as cancer. The biologically functional protein may also be a selectable marker for antibiotic resistance such as a selectable marker for neomycin resistance in eukaryotes. Other types of selectable markers may also be used. The therapeutic polynucleotide encoding these proteins can be provided by any of a variety of methods, such as routine cloning procedures (Sambrook et al.), excision from a vector containing the gene of interest, or chemical or enzymatic synthesis based on published sequence information. In many instances the DNA encoding the protein of interest is commercially available.

The biologically functional protein can affect cellular mechanism by providing a new or altered function to a cell. For example, the therapeutic polynucleotide can be a multidrug resistance gene (mdr) which encodes P-glycoprotein. P-glycoprotein is a cell membrane glycoprotein which affects intracellular drug accumulation and is responsible for the phenomenon of multidrug resistance.

The therapeutic polynucleotide can encode a non-biologically functional protein. For example, a hybrid gene comprising various domains and functions from a variety of sources can be designed and produced by recombinant technology or enzymatic or chemical synthesis.

The therapeutic polynucleotide may be capable of being transcribed into an RNA molecule which is sufficiently complementary to hybridize to an mRNA or DNA of interest, i.e. a sense or antisense RNA. Such RNA molecules may be useful in preventing or limiting the expression of over-produced, defective, or otherwise undesirable molecules. The AAV vector of the present invention can comprise, as the therapeutic polynucleotide, a sequence encoding an antisense RNA which is sufficiently complementary to a target sequence such that it binds to the target sequence. For example, the target sequence can be part of the mRNA encoding a polypeptide such that it binds to and prevents translation of mRNA encoding the polypeptide. The target sequence may be a segment of a gene that is essential for transcription such that the antisense RNA binds the segment (e.g. a promoter or coding region) and prevents or limits transcription. Hence, the antisense RNA must be of sufficient length and complementarity to prevent translation of its target mRNA or transcription of its target DNA. Antisense RNAs having sufficient complementarity to a target sequence such that the antisense RNA is capable of binding to the target and thereby inhibiting translation or transcription can be determined using standard techniques. The therapeutic polynucleotide can be provided, for example, by chemical or enzymatic synthesis, or from commercial sources.

The function of the AAV vectors of the present invention, i.e. the ability to mediate transfer and expression of therapeutic polynucleotide, can be evaluated by monitoring the expression of the therapeutic polynucleotide in transduced cells. For example, cells may be transfected with an AAV vector of the present invention or infected with varying concentrations of virions containing said AAV vector and then assessed for the expression of the therapeutic polynucleotide.

The assay for expression depends upon the nature of the therapeutic polynucleotide. Expression can be monitored by a variety of methods including immunological, histo-chemical or activity assays. For example, Northern analysis can be used to assess transcription using appropriate DNA or RNA probes. If antibodies to the polypeptide encoded by the therapeutic polynucleotide are available, Western blot analysis, immunohistochemistry or other immunological techniques can be used to assess the production of the polypeptide. Appropriate biochemical assays can also be used if the therapeutic polynucleotide is an enzyme. For example, if the therapeutic polynucleotide encodes antibiotic resistance, a determination of the resistance of infected cells to the antibiotic can be used to evaluate expression of the antibiotic resistance gene.

In addition to assessing that the heterologous gene is expressed in the appropriate cells, the correct promoter specificity of the AAV vectors can be evaluated by monitoring the expression of the therapeutic polynucleotide, or lack of expression, in cells in which the promoter is not expected to be active.

The therapeutic polynucleotide of the invention may be a gene selected from CFTR for CF, α1-antitrypsin for emphysema, soluble CD4 for AIDS, ADA for adenosine deaminase deficiency and any other gene recognised as being potentially useful for gene therapy.

The AAV vectors of the present invention can be adapted to ex vivo and in vitro gene therapy applications.

The AAV vectors of the present invention may also be used to deliver other therapeutics. For example, the AAV vectors of the present invention may be used to deliver small molecule, peptide and/or protein therapeutics.

The AAV vectors of the present invention may be used in combination with other therapeutic agents and/or therapeutic methods. In particular, the AAV vectors of the invention may be used in combination with standard therapeutic agents and/or methods in the treatment of diseases including, but not limited to, cancer. AAV induced immunity can enhance the antibody function. Therefore, one example of a therapeutic use according to the present invention is the use of AAV vectors of the invention to deliver therapeutic antibodies, or the use of AAV vectors of the invention in combination with therapeutic antibodies.

Accordingly, the present invention provides an AAV vector as described herein for use in a method of therapy. The invention also provides the use of an AAV vector as described herein in the manufacture of a medicament for gene therapy.

The following Examples illustrate the invention

EXAMPLES

Example 1—Vector Production

Two forms of vector particles, that is, complete and empty (without any transgene sequence) particles from each of the three AAV serotypes, i.e. AAV2, AAV5 and AAV8, were produced and investigated. The complete vector particles contained a vector sequence encoding GFP and the empty vector particles were capsids without a vector sequence.

Complete AAV particles were expressed from 3 plasmids pHelper (Stratagene, USA), pAAV-RC encoding AAV Rep-Cap and pAAV-hrGFP (Stratagene, USA) and empty AAV capsids expressed from only pHelper and pAAV-RC. Plasmid pAAV2/2 Rep-Cap was purchased from Stratagene (USA) and, plasmids pAAV-2/5-RC and AAV-2/8-RC were kindly provided by Professor James Wilson (NIDCR/Pennsylvania, USA).

All vectors were produced by transient transfection of human embryonic kidney 293T cells (Stratagene, USA) using the Calcium phosphate-BBS method (Chen et al., (1988) *Biotechniques* 6: 632-638). Vector producer cells were harvested and were subjected to 5 cycles of freeze thaw to release vector particles and the cellular debris was removed by centrifugation (2000 g).

The supernatant containing vector particles was then filtered through 0.451 µm filters (Millipore, UK) and diluted with 20 mM Bis-Tris Propane buffer prior to chromatography. A Gilson HPLC system (Anachem, UK) was used for chromatography, which was equipped with a UV-Detector (Gilson, 119), pump (Gilson 306), autosampler (Gilson 231XL) and fraction collector (Gilson FC203B) both fitted with temperature controlled racks connected to a refrigerated re-circulating water bath (Grant, SLS) which also cooled the water-jacketed column. The system was controlled using Gilson Unipoint software. An XK 16/26 column (Amersham, UK) was packed to contain a bed volume of 5 ml AVB Sepharose High Performance medium (GE Healthcare, Sweden), and performed following the manufacturer's protocol.

The AVB Sepharose affinity chromatography used in this study was designed for the purification of Adeno-associated viruses. FIG. 1A shows a typical protein separation using a 5 ml column containing AVB Sepharose coupled with AAV antibodies and that majority proteins were not bound to AAV antibodies and thus flowed through the column before the elution buffer (50 mM Glycine, pH2.7) being applied (FIG. 1A). Both empty capsids and complete vectors were eluted at 25-35 minutes of migration time (FIG. 1A). The protein profile of eluted samples was then visualised using SDS-PAGE and silver staining (FIG. 1B), showing significant purity of AAV samples after chromatography. As expected, three dominant AAV capsids proteins VP1 (81 kDa), VP2 (72 kDa) and VP3 (62 kDa) were evident. Crude un-purified AAV samples showed many protein bands.

Example 2—Identification of Proteins from the AAV Vectors Using LC-MS/MS

Purified vector particles from Example 1 were pooled and dialysis to equilibrate into PBS in a 10K MWCO Slide-A-Lyzer dialysis cassette (Thermo scientific, USA) and concentrated to 1/20 of initial volume using Ultra 5K MWCO centrifugal filter devices (Millipore, UK) before being subjected to vector quantitation.

Vector quantitation Genome titre of purified vectors was determined using SYBR green dye real-time qPCR with AAV2 ITR primers GGAACCCCTAGTGATGGAGTT (SEQ ID NO: 24) and CGGCCTCAGTGAGCGA (SEQ ID NO: 25) and probe CACTCCCTCTCTGCGCGCTCG (SEQ ID NO: 26), with the probe labelled at the 5' end with 6-carboxyfluoescein (6-FAM) and at the 3' end with carboxytetramethylrhodamine (TAMRA). A standard curve was generated with plasmid pAAV2-hr-GFP. Total protein was measured using Pierce BCA protein assay kit (Thermo scientific, USA) and following manufacturer's protocol. The identity and the predicted amount of capsids protein were visualised using SilverXpress staining kit (Invitrogen, USA) according to manufacturer's protocol.

Purified and concentrated vector samples were digested with trypsin in the presence of 1% Rapigest and 50 mM ammonium bicarbonate (ABC) pH 8.5 for 3 hrs at 37° C. The digestion was then terminated by adding HCl before the samples were subjected to MS analysis.

LC-MS/MS was carried out using a mass spectrometry system (Thermo Fisher, UK) equipped with a nano-electrospray ion source and two mass detectors i.e. linear trap (LTQ) and orbitrap, coupled with an Ultimate 3000 nano-LC system, comprising a solvent degasser, a loading pump, a nano-pump, and a thermostated autosampler. After an automated injection, the extracted peptides from each digestion were desalted in a trapping cartridge (PepMap reversed phase C18, 5 µm 100 Å, 300 µid×5 mm length) (Thermo) and eluted on to a C18 reversed phase nano-column (3 µm, 100Å, 5 cm length) (Thermo), and followed by a 60 min separation under a column flow rate of 0.3 pL/min using linear gradient from 5-70% acetonitrile and 0.1% formic acid. After a first survey MS scan (from m/z 400-2000) in the LTQ, the 5 most intense ions were sequentially isolated and passed to the Orbi-trap for accurate mass measurement with the resolution of 30,000 ppm. These were then fragmented in the linear ion trap at collision induced energy of 35%. The total cycle time was approximately 30 milliseconds. Data was collected in data dependent MS/MS mode with dynamic exclusion set to 2 counts.

Data analysis including mass spectra processing and database searching was carried out using Thermo Proteome Discoverer 1.2. with built-in Sequest. Initial mass tolerances for protein identification by MS were set to 10 parts per million (ppm). Up to two missed tryptic cleavages were considered and methionine oxidation was set as dynamic modification. Peptide sequences by MS/MS were only included when Xcorrelation scores were greater than 1.5, 2 or 2.2 for charge states 1, 2 and 3, respectively. An unambiguous identification was considered when at least two peptides matched to the protein. The protein FASTA databases were downloaded from www.uniprot.org, release 2012-03 including the complete entries from *Homo sapiens* (taxon identifier 9606) *Bos taurus* (9913), green fluorescent protein (P42212) and AAV2 (648242), AAV5 (82300) and AAV8 (202813).

Equal amount of total proteins from six different types of purified AAV vector samples, i.e. AAV2-GFP, AAV2-Empty, AAV5-GFP, AAV5-Empty, AAV8-GFP and AAV8-Empty, were subjected to LC-MS/MS analysis. To minimise data variation, three batches of samples were prepared for each type of vectors with each batch pooled from 40 tissue culture plates (150 mm diameter). Three MS runs were performed for each batch of samples. The results showed that 66 proteins were detected in at least 2/3 runs of three batches of samples and were thus considered to be significant and to be further studied. These proteins are listed in Table 2.

Among the significant proteins:
four proteins, i.e. GapDH, Heat shock 70 kDa protein 1A/1B, Histotone H2Atype 1H and Histone H2B were common to all 6 types of AAV vectors regardless of serotypes and particle forms;
six proteins shared by 5 types of vectors;
out of 10 proteins shared by four forms of samples, six proteins shared by both empty and complete forms of AAV2 and AAV5, indicating a relative similarity between AAV2 and AAV5 vectors;
20 proteins were common to two types of vectors, the majority of which were common to the empty and complete forms of the same serotype; and
21 proteins were unique to individual types of vectors.

TABLE 2

List of Proteins Identified in MS/MS Studies

| | Proteins ID | AAV2E | AAV2G | AAV5E | AAV5G | AAV8E | AAV8G |
|---|---|---|---|---|---|---|---|
| Shared by 6 (4 proteins) | Glyceraldehyde-3-phosphate dehydrogenase (Fragment) OS = *Homo sapiens* GN = GAPD PE = 2 SV = 1-[Q5ZEY3_HUMAN] | + | + | + | + | + | + |
| | Heat shock 70 kDa protein 1A/1B OS = *Homo sapiens* GN = HSPA1A PE = 1 SV = 5-[HSP71_HUMAN] | + | + | + | + | + | + |
| | Histone H2A type 1-H OS = *Homo sapiens* GN = HIST1H2AH PE = 1 SV = 3-[H2A1H_HUMAN] | + | + | + | + | + | + |
| | Histone H2B OS = *Homo sapiens* PE = 2 SV = 1-[A8K9J7_HUMAN] | + | + | + | + | + | + |
| Shared by 5 (6 proteins) | 60S acidic ribosomal protein P2 OS = *Homo sapiens* GN = RPLP2 PE = 1 SV = 1-[RLA2_HUMAN] | + | + | + | + | | + |
| | Alpha-enolase OS = *Homo sapiens* GN = ENO1 PE = 1 SV = 2-[ENOA_HUMAN] | + | + | + | + | | + |
| | Nucleolin, isoform CRA_c OS = *Homo sapiens* GN = NCL PE = 2 SV = 1-[B3KM80_HUMAN] | + | + | + | + | | + |
| | Nucleophosmin OS = *Homo sapiens* GN = NPM1 PE = 1 SV = 2-[NPM_HUMAN] | + | + | + | + | | + |
| | YBX1 protein (Fragment) OS = *Homo sapiens* GN = YBX1 PE = 2 SV = 1-[Q6PKI6_HUMAN] | + | + | + | + | | + |
| | RuvB-like 2 OS = *Homo sapiens* GN = RUVBL2 PE = 1 SV = 3-[RUVB2_HUMAN] | + | + | + | + | | + |
| shared by 4 (10 proteins) | Annexin A5 OS = *Homo sapiens* GN = ANXA5 PE = 1 SV = 2-[ANXA5_HUMAN] | + | + | + | + | | |
| | Brain acid soluble protein 1 OS = *Homo sapiens* GN = BASP1 PE = 1 SV = 2-[BASP1_HUMAN] | + | + | + | + | | |
| | Histone H2A.x OS = *Homo sapiens* GN = H2AFX PE = 1 SV = 2-[H2AX_HUMAN] | + | + | | | + | + |
| | MARCKS protein (Fragment) OS = *Homo sapiens* GN = MARCKS PE = 2 SV = 1-[Q6NVI1_HUMAN] | + | + | + | + | | |
| | MYL6 protein OS = *Homo sapiens* GN = MYL6 PE = 2 SV = 1-[Q6IBG5_HUMAN] | + | + | + | + | | |

TABLE 2-continued

List of Proteins Identified in MS/MS Studies

| | Proteins ID | AAV2E | AAV2G | AAV5E | AAV5G | AAV8E | AAV8G |
|---|---|---|---|---|---|---|---|
| | Nascent polypeptide-associated complex alpha subunit (CypA) (Fragment) OS = *Homo sapiens* GN = NACA PE = 4 SV = 1- [F8W1N5_HUMAN] | + | + | + | + | | |
| | Peptidyl-prolyl cis-trans isomerase (Fragment) OS = *Homo sapiens* GN = PPIH PE = 3 SV = 1- [C9JQD4_HUMAN] | + | + | | | + | + |
| | Putative uncharacterized protein (Fragment) OS = *Homo sapiens* PE = 2 SV = 1-[Q8WVW5_HUMAN] | + | | + | | + | + |
| | RuvB-like 1 (Fragment) OS = *Homo sapiens* GN = RUVBL1 PE = 2 SV = 1- [B5BUB1_HUMAN] | + | + | + | + | | |
| | Triosephosphate isomerase (Fragment) OS = *Homo sapiens* PE = 2 SV = 1-[Q53HE2_HUMAN] | + | + | + | + | | |
| shared by 3 (5 proteins) | 78 kDa glucose-regulated protein OS = *Homo sapiens* GN = HSPA5 PE = 1 SV = 2-[GRP78_HUMAN] | | | + | + | + | |
| | ATP synthase subunit beta (Fragment) OS = *Homo sapiens* GN = ATP5B PE = 2 SV = 1- [Q0QEN7_HUMAN] | | | + | + | + | |
| | Chaperonin 10-related protein (Fragment) OS = *Homo sapiens* GN = EPFP1 PE = 2 SV = 1- [Q9UNM1_HUMAN] | | | + | + | + | |
| | L-lactate dehydrogenase B chain OS = *Homo sapiens* GN = LDHB PE = 1 SV = 2-[LDHB_HUMAN] | + | + | | | + | |
| | Synaptic vesicle membrane protein VAT-1 homolog OS = *Homo sapiens* GN = VAT1 PE = 1 SV = 2- [VAT1_HUMAN] | + | + | + | | | |
| shared by 2 (20 proteins) | Actin, gamma 1 OS = *Homo sapiens* GN = ACTG1 PE = 3 SV = 1- [F5H0N0_HUMAN] | | | + | + | | |
| | Annexin A2 (Fragment) OS = *Homo sapiens* GN = ANXA2 PE = 4 SV = 1- [H0YKZ7_HUMAN] | | | + | + | | |
| | ATP synthase subunit alpha OS = *Homo sapiens* PE = 2 SV = 1- [B4DY56_HUMAN] | | | + | + | | |
| | ATP synthase-coupling factor 6, mitochondrial OS = *Homo sapiens* GN = ATP5J PE = 1 SV = 1- [ATP5J_HUMAN] | | | + | + | | |
| | Capsid protein VP1 OS = Adeno-associated virus 2 (isolate Srivastava/1982) PE = 1 SV = 2- [CAPSD_AAV2S] | + | + | | | | |
| | Capsid protein OS = Adeno-associated virus-5 GN = cap PE = 1 SV = 1-[Q9YIJ1_9VIRU] | | | + | + | | |
| | Capsid protein OS = Adeno-associated virus-8 PE = 1 SV = 1- [Q8JQF8_9VIRU] | | | | | + | + |
| | Cofilin 1 (non-muscle) (Fragment) OS = *Homo sapiens* GN = CFL1 PE = 4 SV = 1-[E9PLJ3_HUMAN] | | | + | + | | |
| | Complement component 1 Q subcomponent-binding protein, mitochondrial OS = *Homo sapiens* GN = C1QBP PE = 1 SV = 1- [C1QBP_HUMAN] | | | + | + | | |
| | Erythrocyte membrane protein band 4.1-like 3 OS = *Homo sapiens* GN = EPB41L3 PE = 2 SV = 1- [A8K968_HUMAN] | | | + | + | | |

TABLE 2-continued

List of Proteins Identified in MS/MS Studies

| | Proteins ID | AAV2E | AAV2G | AAV5E | AAV5G | AAV8E | AAV8G |
|---|---|---|---|---|---|---|---|
| | Heterogeneous nuclear ribonucleoprotein A1 (Fragment) OS = *Homo sapiens* GN = HNRNPA1 PE = 4 SV = 1-[F8VTQ5_HUMAN] | | | | | + | + |
| | Heterogeneous nuclear ribonucleoprotein K (hnRNPK) OS = *Homo sapiens* GN = HNRNPK PE = 2 SV = 1-[Q5T6W5_HUMAN] | | | | + | | + |
| | Myosin-10 OS = *Homo sapiens* GN = MYH10 PE = 1 SV = 3-[MYH10_HUMAN] | | | + | + | | |
| | Myosin-9 OS = *Homo sapiens* GN = MYH9 PE = 1 SV = 4-[MYH9_HUMAN] | | | + | + | | |
| | Pyruvate kinase OS = *Homo sapiens* PE = 2 SV = 1-[B4DNK4_HUMAN] | | | + | | + | |
| | Ribosomal protein L5, isoform CRA_b OS = *Homo sapiens* GN = RPL5 PE = 2 SV = 1-[B3KTM6_HUMAN] | + | | | | + | |
| | Serine/arginine repetitive matrix protein 1 OS = *Homo sapiens* GN = SRRM1 PE = 1 SV = 2-[SRRM1_HUMAN] | + | + | | | | |
| | Single-stranded DNA binding protein 1 (Fragment) OS = *Homo sapiens* GN = SSBP1 PE = 4 SV = 1-[C9K0U8_HUMAN] | | | | | + | + |
| | Tubulin, alpha 1b (Fragment) OS = *Homo sapiens* GN = TUBA1B PE = 4 SV = 1-[F8VRK0_HUMAN] | + | | | | + | |
| | Uncharacterized protein OS = *Homo sapiens* GN = SLC1A5 PE = 2 SV = 1-[B4DWS4_HUMAN] | | | + | + | | |
| Unique (21 proteins) | Adenylyl cyclase-associated protein OS = *Homo sapiens* PE = 2 SV = 1-[B4DI38_HUMAN] | | | | | + | |
| | ATP synthase, H+ transporting, mitochondrial F1 complex, beta polypeptide (Fragment) OS = *Homo sapiens* GN = ATP5B PE = 4 SV = 1-[H0YH81_HUMAN] | | | + | | | |
| | DNA-binding protein A OS = *Homo sapiens* GN = CSDA PE = 1 SV = 4-[DBPA_HUMAN] | | | | | + | |
| | Elongation factor Tu, mitochondrial OS = *Homo sapiens* GN = TUFM PE = 1 SV = 2-[EFTU_HUMAN] | | | + | | | |
| | Enolase (Fragment) OS = *Homo sapiens* GN = ENO1 PE = 2 SV = 1-[Q9BT62_HUMAN] | | | + | | | |
| | EPB41 protein (Fragment) OS = *Homo sapiens* GN = EPB41 PE = 2 SV = 1-[Q4VB87_HUMAN] | | | + | | | |
| | HSP90AB1 protein (Fragment) OS = *Homo sapiens* GN = HSP90AB1 PE = 2 SV = 1-[Q6PK50_HUMAN] | | | + | | | |
| | IMP (inosine 5'-monophosphate) dehydrogenase 2 (Fragment) OS = *Homo sapiens* GN = IMPDH2 PE = 4 SV = 1-[H0Y4R1_HUMAN] | | | + | | | |
| | Insulin-like growth factor 2 mRNA binding protein 1, isoform CRA_a OS = *Homo sapiens* GN = IGF2BP1 PE = 4 SV = 1-[D3DTW3_HUMAN] | | | + | | | |
| | Liver histone H1e OS = *Homo sapiens* PE = 2 SV = 1-[A3R0T7_HUMAN] | | | | | + | |
| | Major coat protein Aa OS = Adeno-associated virus 2 (isolate Srivastava/1982) PE = 4 SV = 1-[Q89269_AAV2S] | | | | | + | |

TABLE 2-continued

List of Proteins Identified in MS/MS Studies

| Proteins ID | AAV2E | AAV2G | AAV5E | AAV5G | AAV8E | AAV8G |
|---|---|---|---|---|---|---|
| Methylenetetrahydrofolate dehydrogenase (NADP+ dependent) 1, methenyltetrahydrofolate cyclohydrolase, formyltetrahydrofolate synthetase OS = Homo sapiens GN = MTHFD1 PE = 3 SV = 1-[G3V2B8_HUMAN] | | | | + | | |
| Nucleolar RNA helicase 2 OS = Homo sapiens GN = DDX21 PE = 1 SV = 5-[DDX21_HUMAN] | | | | + | | |
| Ornithine aminotransferase, mitochondrial OS = Homo sapiens GN = OAT PE = 1 SV = 1-[OAT_HUMAN] | | | + | | | |
| Proteasome (prosome, macropain) 26S subunit, ATPase, 3 OS = Homo sapiens GN = PSMC3 PE = 3 SV = 1-[E9PM69_HUMAN] | | | + | | | |
| Rep78 OS = Adeno-associated virus-Go.1 PE = 4 SV = 1-[Q2LD61_9VIRU] | | | + | | | |
| SFPQ protein (Fragment) OS = Homo sapiens GN = SFPQ PE = 2 SV = 2-[Q9BSV4_HUMAN] | | | | | + | |
| Signal recognition particle 72 kDa, isoform CRA_c OS = Homo sapiens GN = SRP72 PE = 4 SV = 1-[G5E9Z8_HUMAN] | | | + | | | |
| Small nuclear ribonucleoprotein polypeptide B OS = Homo sapiens PE = 2 SV = 1-[Q5XPV6_HUMAN] | | | + | | | |
| THO complex subunit 4 OS = Homo sapiens GN = ALYREF PE = 1 SV = 3-[THOC4_HUMAN] | | | + | | | |
| TUBA1B protein OS = Homo sapiens GN = TUBA1B PE = 2 SV = 1-[Q8WU19_HUMAN] | | | + | | | |

Example 3—Validation of MS Data

In order to validate the mass spectrometry data obtained in Example 2, two categories of proteins identified using MS were selected for immunoblotting: (i) proteins NPM1, NCL1 and ATP5A that have an documented role in AAV life cycle; and (ii) proteins Annexin V, RuvB, CypA, hnRNPK and YB1 that have no reported association with AAV but have a relatively high score and confidence in MS analysis.

10% SDS polyacrylamide gel was used to resolve protein samples and the gels then subjected to immunoblotting. Samples for immunoblotting were electrophoresed and electroblotted to Hybond ECL membranes (Amersham, UK). The following primary antibodies were used: mouse anti AAV2, mouse anti Annexin V (Abcam, UK), anti nucleolin (Abcam, UK), anti nucleophosmin (Abcam, UK), anti EF1β2 (Abcam, UK), anti CypA (Abnova, UK), anti RuBV2 (Abcam, UK), anti hnRNP K (Abcam, UK), anti ATP5A (Abcam, UK and anti YB1 (Abcam, UK). The immunoblots were further incubated with goat anti-mouse, anti-rabbit or rabbit anti-goat horseradish peroxidase conjugates (Sigma, UK). The immuno-reactive proteins were detected using ECL chemiluminescence reagents (Amersham, UK).

For each sample, 10 μg of total protein from the same samples used for MS/MS were resolved using SDS/PAGE before being subjected for immunoblotting. The total protein was visualised using SDS/PAGE and silver staining (FIG. 1B), confirming sample purity and a comparable amount of AAV capsid proteins VP1, VP2 and VP3

Figure 2:
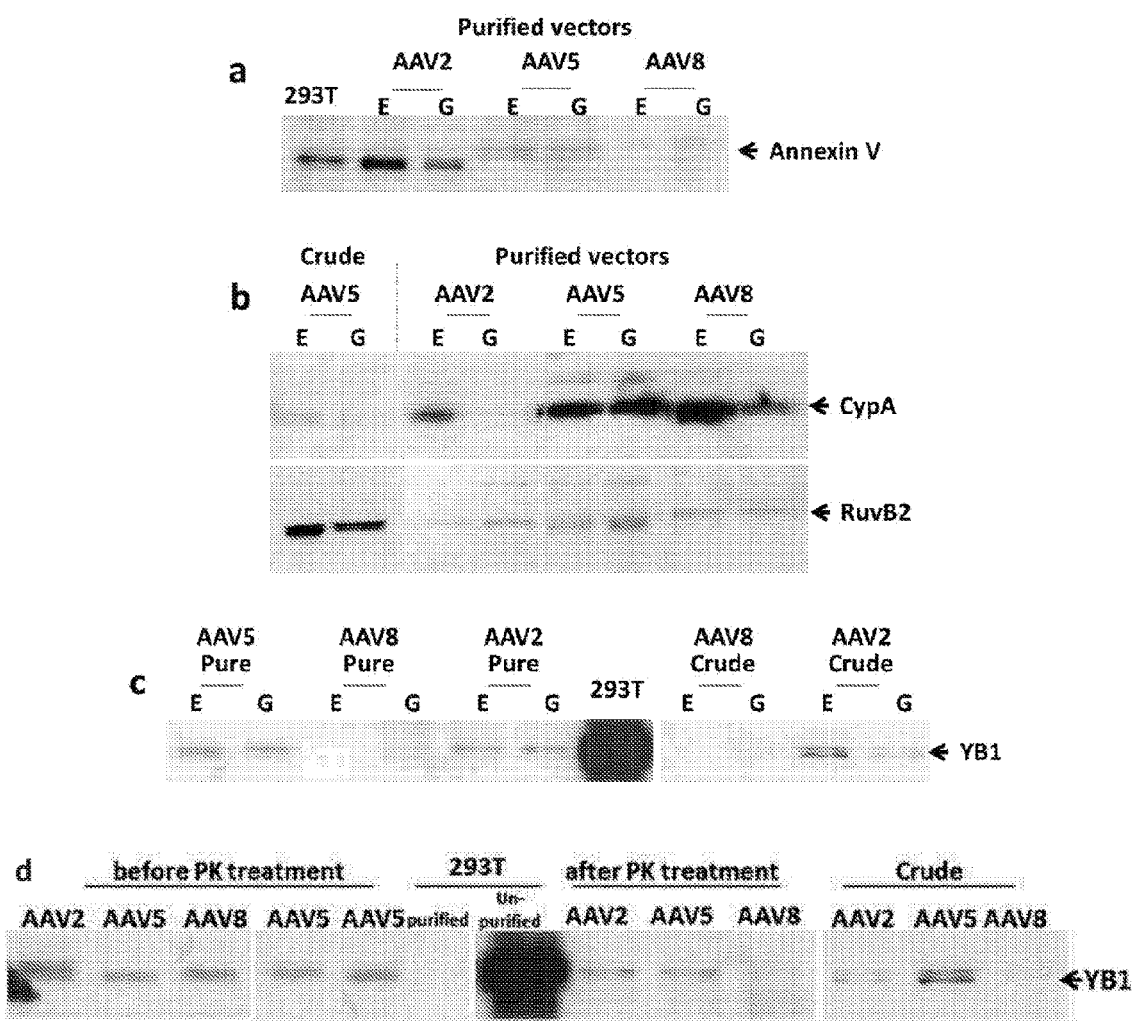
FIG. 2. Immunoblotting analysis of cellular proteins showing the association of (a) Annexin A5, (b) CypA and RuvB2; (c) YB1 with AAV vectors before (crude) and after (purified) affinity chromatography. E: empty capsids, G: complete AAV carrying GFP and control 293T cell lysate; (d) association of YB1 with AAV vectors, using proteinase K to remove trace unincorporated cellular proteins that remained in purified vectors and were not protected by vector capsid.

The immunoblotting showed that RuvB2, CypA and Annexin A5 were detected in all samples tested (FIGS. 2A and B). YB1 was detected in all samples except AAV8 empty capsids (FIG. 2C), regardless of them being crude or purified. To discriminate between incorporated and co-purified but unincorporated cellular proteins in AAV vectors, proteinase K (PK) was used to remove trace unincorporated cellular proteins that remained in purified vectors and were not protected by vector capsid. FIG. 2D showed a comparable detection of YB1 proteins in purified AAV vectors before and after PK treatment, indicating YB1 incorporation in AAV vectors. Furthermore, there was no detection of YB1 proteins in purified control 293T cell that had been treated and HPLC-purified in parallel with AAV vectors (lane unpurified, FIG. 2D), highlighting the specificity of the adopted AVB column for AAV vector purification and further demonstrating the incorporation of YB1 proteins in AAV vectors. hnRNPK was not detected in any of the samples tested (data not shown).

The results from the immunoblotting and MS studies were further summarized and compared in Table 3, showing a 22.9% (11/48 sample s tested, highlighted with circles) difference and 77.1% agreement in protein detection between these two different methods.

Example 4—Influence of AAV Production on Protein Expression in Producer Cells

Figure 3:
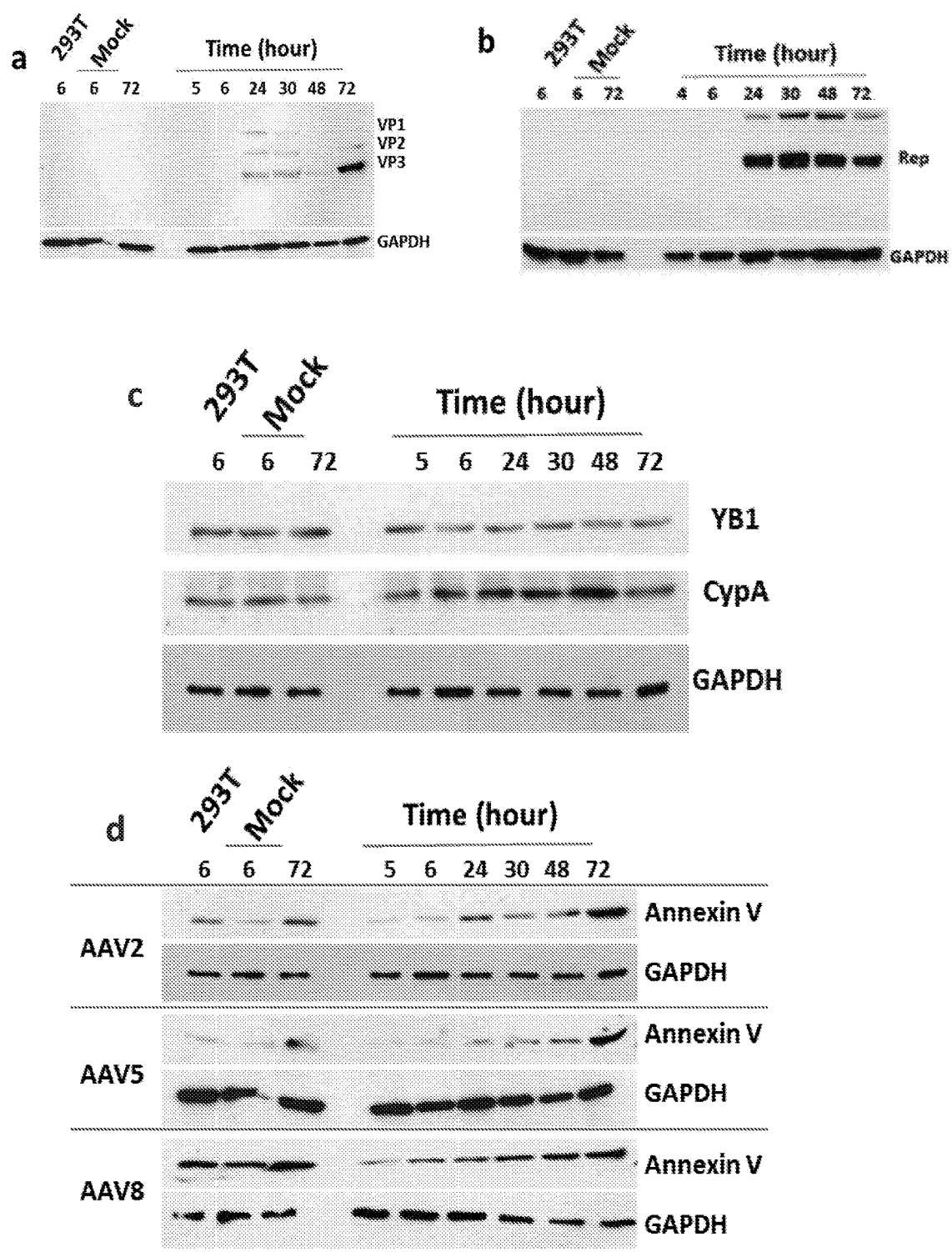
FIG. 3. Chronological analysis of protein expression in producer cells. (a) AAV proteins (VP1, VP2 and VP3) were detectable 24 hours after transfection with a slight increase from 24 to 72 hours after transfection; (b) Rep proteins were detectable 24 hours after transfection; (c) the expression of YB1 and CypA remains unchanged throughout a complete production cycle and; (d) overtime increase in Annexin A5 expression were observed in all three serotypes of AAV. Controls: 293T cell lysate without the transfection of any plasmids (293T), 293T cells with the transfection of pcDNA3 plasmids (Mock), and housekeeping gene GAPDH as a loading control.

In order to investigate potential influences of AAV production on the expression of both viral and cellular proteins in producer cells, changes in the expression of AAV capsid proteins, Annexin A5, CypA and YB1 were analysed throughout one complete cycle of AAV production, i.e. from 0 hour before the transfection of AAV and helper plasmids to 4, 6, 24 30, 48, and 72 hours after transfection when vector production process was terminated and AAV vectors harvested. AAV capsid proteins (VP1, VP2 and VP3) and Rep proteins could be detected 24 hours after transfection in AAV2 producer cells (FIGS. 3A and 3B). A slight increase in the capsid proteins in producer cells was observed from 24 to 72 hours after transfection. Throughout a complete cycle of AAV production, no significant changes were observed in YB1 and CypA expression (FIG. 3C); over-time increase in Annexin A5 expression was observed in all three serotypes (FIG. 3D).

TABLE 3

Comparison of Immunoblotting and MS Results

| | Immunoblotting | | | MS | | |
|---|---|---|---|---|---|---|
| Serotype | | | | | | |
| | AAV2 | AAV5 | AAV8 | AAV2 | AAV5 | AAV8 |
| Forms | | | | | | |
| Protein | E G | E G | E G | E G | E G | E G |
| RuVB | + + | + + | + + | + + | + + | ⊖ + |
| CypA | + + | + + | + + | + + | + + | ⊖ ⊖ |
| Annexin A5 | + + | + + | + + | + + | + + | ⊖ ⊖ |
| ATPA5 | − − | + + | + + | + + | + + | ⊖ + |
| NPM1 | + − | + − | + − | + ⊕ | + ⊕ | + − |
| YB1 | + + | + + | + + | + + | + + | ⊖ + |
| NCL | + + | + + | + − | + + | + + | + − |
| hnRNPK | − − | − − | − − | − − | ⊕ − | ⊕ |

Example 5—shRNA Knockdown of NPM1, NCL and YB1

Functional shRNA specifically recognizing a target gene results in down-regulation of the expression of that gene. This strategy was selected as an alternative to study the role of cellular proteins in AAV assembly, as it was not possible to establish cells in culture to overexpress NCL and NPM1 (data not shown).

On the assumption that shRNA knockdown of NPM1, NCL, Annexin V and/or YB1 in producer cells would impair the (MS/MS and immunoblot identified) association of NPM1, NCL, Annexin V and/or YB1 with AAV virus and might subsequently influence AAV production in the gene-knockdown cells, a Lentiviral vector delivery system was used to screen shRNA sequences.

Functional shRNA specifically recognizing a target gene causes down-regulation of the targeted gene expression. To identify the role and importance of YB1 and Annexin A5 in AAV production, experiments were designed knockdown YB1 or Annexin A5 in producer cells using shRNA, the hypothesis being that this knockdown would impair the association of YB1 or Annexin A5 with AAV virus (as identified from the MS/MS and immunoblotting studies) and would subsequently influence AAV assembly in the gene-knockdown cells.

A Lentiviral vector delivery system was used to screen 10 shRNA sequences (A1 to A5, SEQ ID NOs: 19 to 23, and Y1 to Y5, SEQ ID NOs: 14 to 18) targeting Annexin A5 and YB1 for their ability to deregulate Annexin A5 and YB1 respectively.

In more detail, the shRNAs were expressed from plasmid pLKO.1-puro (Sigma, USA) using a Lentiviral expression system. shRNA and lentiviral vector packaging plasmids were transfected into 293T cells using the $CaCl_2$ transfection method. Control cells were transfected with empty capsids without a shRNA sequence (mock) or a scramble shRNA sequence targeting non-mammalian gene sequences (scramble). 293T cells were transduced with LV-shRNA vectors, and were subjected to puromycin selection 48 h after transduction.

AAV vector genome titre was determined by q-PCR with primers and probe targeting the CMV promoter or AAV2 ITR sequences. CMV primers: TTC CTA CTT GGC AGT ACA TCT ACG (SEQ ID NO: 30) and GTC AAT GGG GTG GAG ACT TGG (SEQ ID NO: 31); and CMV probe: TGA GTC AAA CCG CTA TCC ACG CCC A (SEQ ID NO: 32). AAV2 ITR primers GGAACCCCTAGTGATGGAGTT (SEQ ID NO: 24) and CGGCCTCAGTGAGCGA (SEQ ID NO: 25) and probe CACTCCCTCTCTGCGCGCTCG (SEQ ID NO: 26). Again, a 5' 6-FAM and a 3' TAMRA label were used. The plasmid DNA pAAV-hrGFP (Stratagene, USA) was used as reference standard in 10-fold serial dilution ranging from 102 to 108 copies. qPCR was carried out using a LightCycler480 (Roche, USA) under the condition of one 10 min cycle at 950 C, followed by 45 cycles of 15 sec at 950 C, 30 sec at 600 C and 5 sec at 720 C. The level of gene knockdown was evaluated on 10 ug total proteins from shRNA virus transduced cells following the immunoblotting method as described earlier.

Figure 4:
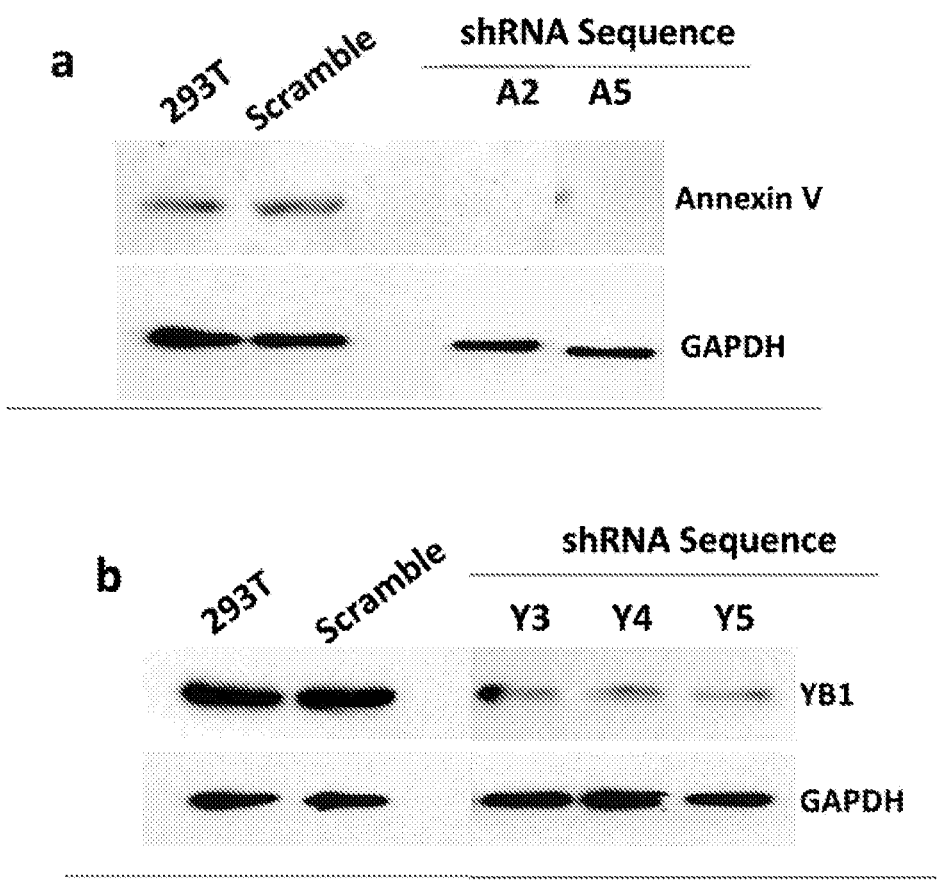
FIG. 4. Immunoblotting analysis of shRNA sequences targeting Annexin A5 and YB1. Significant gene knockdown was observed in producer cells carrying shRNA A2 or A5 and shRNA Y3, Y4 or Y5 sequences targeting (a) Annexin A5 and (b) YB1, respectively. 293T cells with a shRNA sequence targeting non-mammalian genes (Scramble) and without any shRNA sequences (293T) were used as controls. Housekeeping gene GAPDH was further used as a loading control.

As there was no reporter gene in the LV shRNA system to perform the conventional method to titre shRNA viruses, the gene knockdown studies had to be controlled and validated using a direct comparison by simultaneously producing all sample and control shRNA viruses under an identical condition and subsequently using equal volume of shRNA viruses to treat the same number of cells. FIG. 4 shows that the shRNA sequences A2 and A5 significantly down-regulated Annexin A5 expression (FIG. 4A). Likewise, introducing Y3, Y4 or Y5 into cells resulted in significant down-regulation of YB1 (FIG. 4B) compared to controls with sequences targeting non-mammalian genes (scramble) or without a shRNA sequence (293T). Therefore, these 4 shRNA sequences, i.e. A2, A5, Y4 and Y5, were used for subsequent studies.

Producer cells carrying a shRNA sequence, i.e. A2, A5, Y4, Y5 or scramble, were established for AAV production by culture in the presence of puromycin for at least 10 days to remove the cells without puromycin-tagged shRNA. Up to 7 independent knockdown cell lines were generated for each shRNA sequence and were used to produce AAV vectors. To minimise variation, AAV vectors were produced from 15 cm-diameter plates containing over 50 million cells and simultaneously from knockdown and control cell lines produced under identical conditions and were then quantified for AAV genome titres using Real Time PCR.

Figure 5:
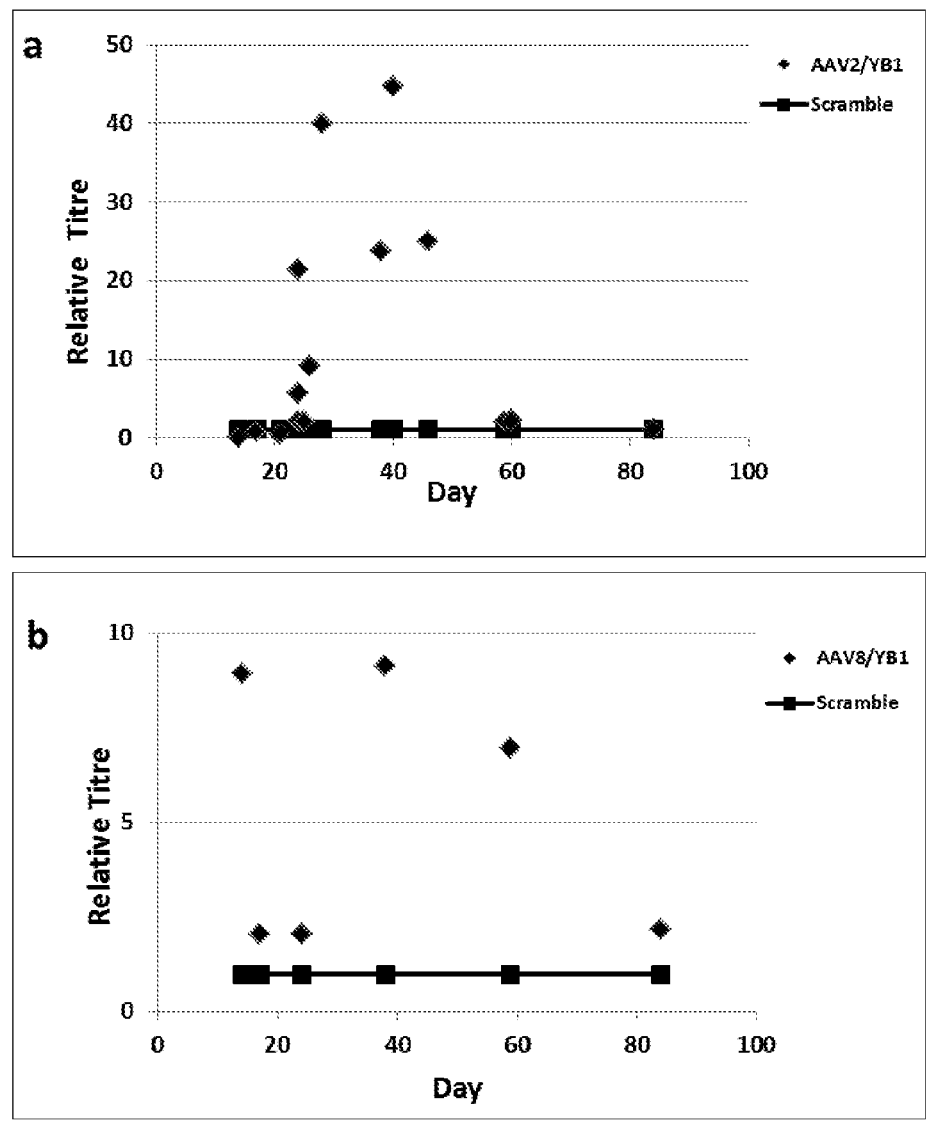
FIG. 5. Vector genome titres of AAV produced in YB1 gene knockdown cells relative to control shRNA scramble, showing (a) up to 50 fold increase in AAV2 and (b) 10 fold increase in AAV8 from 7 batches of gene knockdown producer cells in culture over 80 days.

As shown in FIG. 5, introducing shRNA sequence YB1_Y4 to producer cells resulted in up to 50 fold increase in AAV2 (FIG. 5A) and 10 fold increase in AAV8 (FIG. 5B) vector genome titres relative to control shRNA scramble and that the same Y4 shRNA sequence had no significant influence on AAV5 production (data not shown). This indicates an intrinsic difference among the three serotypes of AAV. Although the reduction of YB1 expression in the knockdown cells continued for over 80 days, the maximum effect of Y4 was only obtained in producer cells that had been in culture for 20-40 days (FIG. 5A). A similar time-dependent pattern was also observed in AAV8 producer cells (FIG. 5B).

Figure 6:
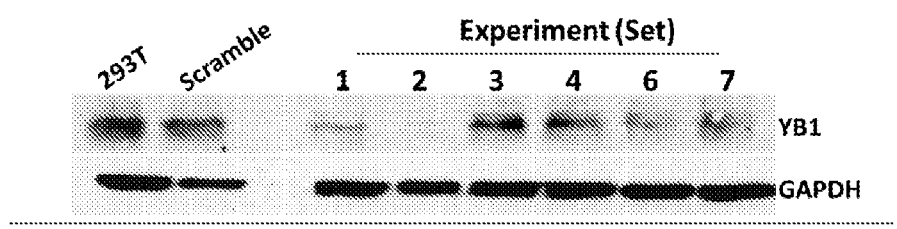
FIG. 6. Sustained down-regulation of YB1 in 6 batches of gene knockdown cells after cryo-preservation and in culture for up to 80 days. 293T cells with a shRNA sequence targeting non-mammalian genes (Scramble) and without any shRNA sequences (293T) were used as controls. Housekeeping gene GAPDH was further used as a loading control.

FIG. 6 shows significant down-regulation of YB1 in 7 batches of knockdown cells that had been recovered from cryo-preservation and had been in culture for 20 to 80 day, demonstrating the comparability among batches and the sustainability of YB1 knockdown cells.

Figure 7:
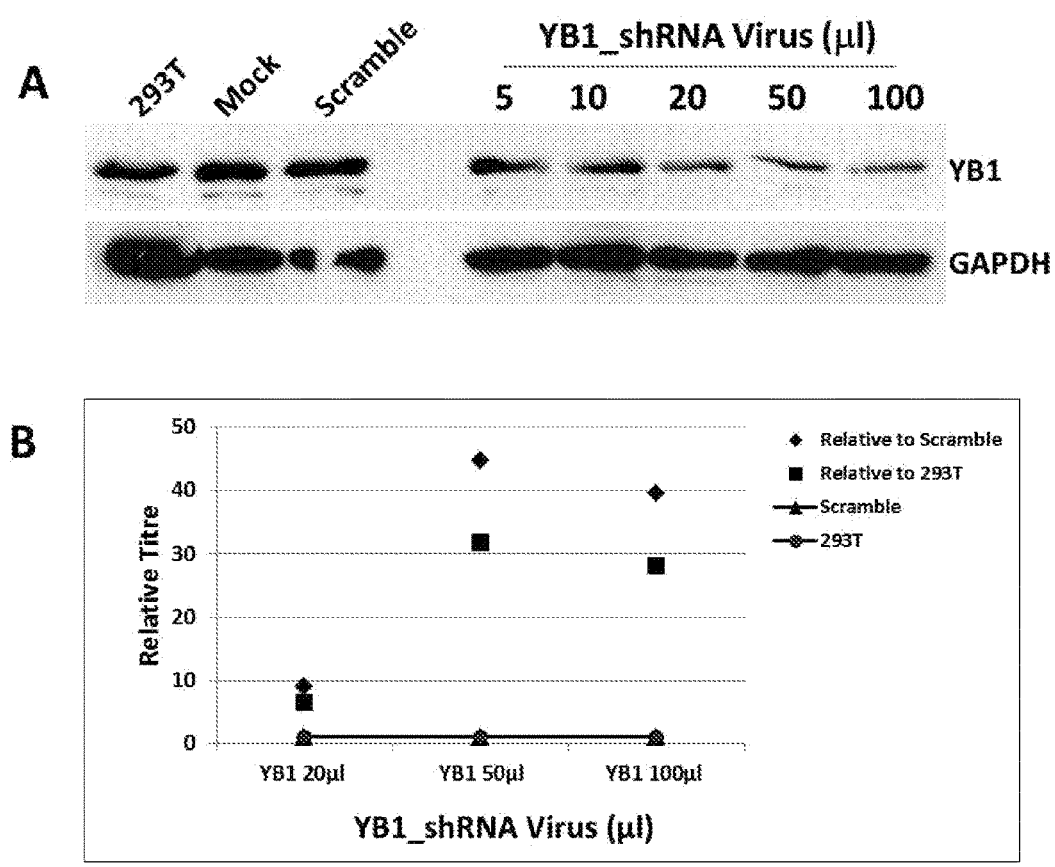
FIG. 7. Correlation of YB1 down-regulation and AAV production to the amount of YB1_shRNA viruses used, showing (a) a slight increase in YB1 deregulation when increasing shRNA viruses and (b) relative AAV2 genome titres to controls scramble and native 293T cells and, the maximum effect on vector genome titres in the producer cells treated with 50 ml YB1-shRNA viruses. Control samples include 293T cells with a shRNA sequence targeting non-mammalian genes (Scramble), with LV empty particles but without a shRNA sequence (Mock) and native 293T cells without any LV and shRNA sequences (293T). Housekeeping gene GAPDH was further used as a loading control.

FIG. 7 shows that there was a slight increase in YB1 deregulation when increasing shRNA viruses from 5 to 100 ml per $10^5$ cells (FIG. 7A) and that the maximum effect on vector genome titres was observed when 50 ml viruses containing shRNA were used (FIG. 7B), indicating a saturating and potential toxic effect on vector production when increasing the amount of viruses containing shRNA.

A Lentiviral vector delivery system was also used to screen 10 shRNA sequences, i.e. N1 to N5 and N6 to N10, targeting NCL and NPM1 genes for their effects on NCL and NPM1 expression respectively.

Figure 8:
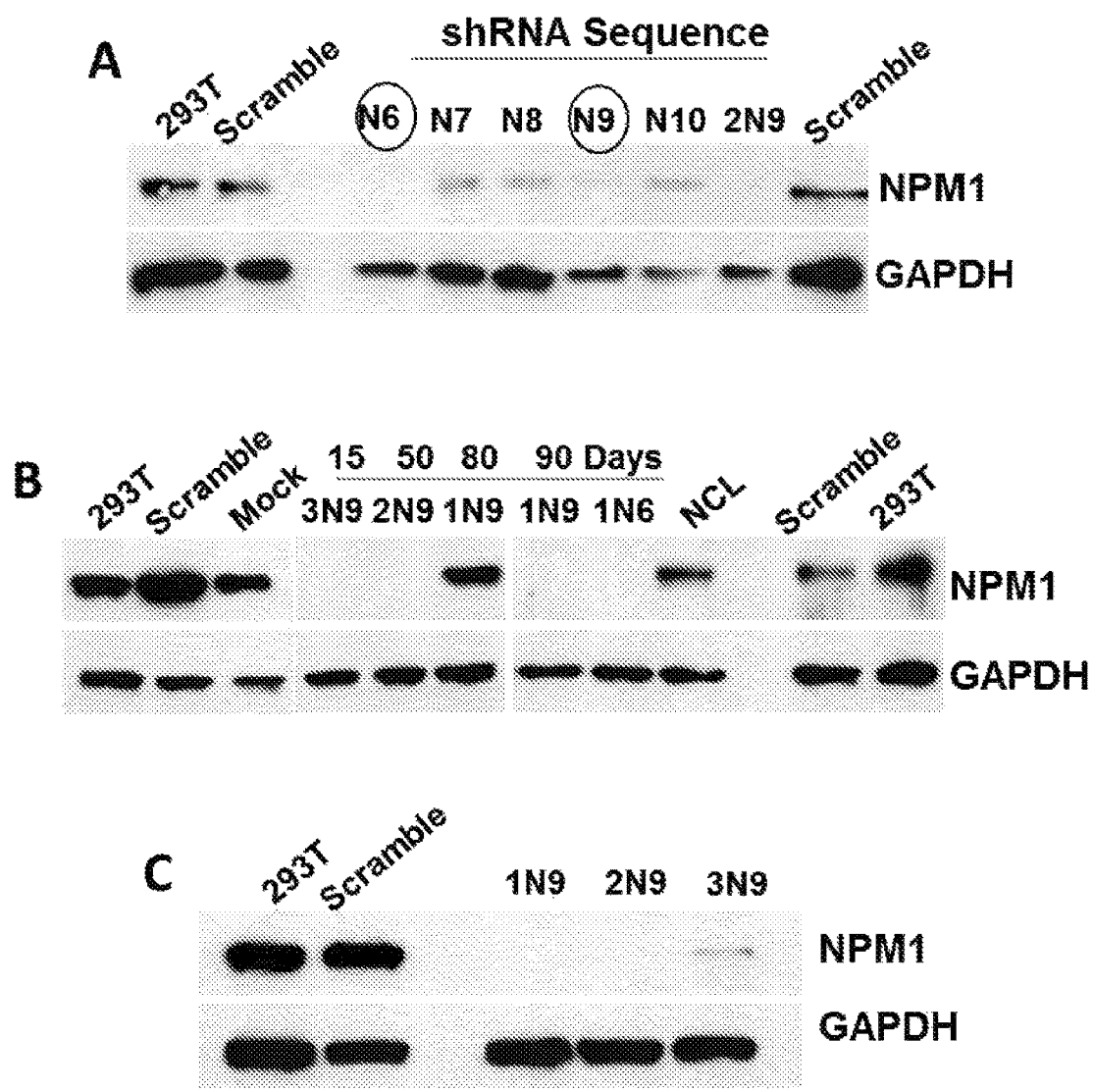
FIG. 8. Immunoblotting analysis of shRNA sequences targeting NPM1. (A) Significant gene knockdown was observed in producer cells carrying shRNA N6 and N9, (B) down-regulation of NPM1 sustained for over 80 days and (C) after being recovered from cryopreservation. 293T cells with a shRNA sequence targeting non-mammalian genes (Scramble) and without any shRNA sequences (293T) were used as controls. Housekeeping gene GAPDH was further used as a loading control.

FIG. 8A showed that introducing shRNA sequences NPM-N6 to NPM-N10 (SEQ ID NOs: 4 to 8) to cells achieved a significant down-regulation of NPM1 expression when compared to two control cells that were either with scramble shRNA targeting non-mammal genes (scramble) or without any shRNA sequences (293T). shRNA NPM-N6 and NPM-N9 (FIG. 8A, circled) showed the most gene knockdown among the 5 sequences tested and were thus selected for subsequent investigations. The reduction of NPM1 expression in NPM1-N9 and NPM1-N6 knockdown cells was sustained for over 80 days after culture in puromycin selection medium (FIG. 8B) and also in the knockdown cells recovered from cryopreservation (FIG. 8C).

Figure 9:
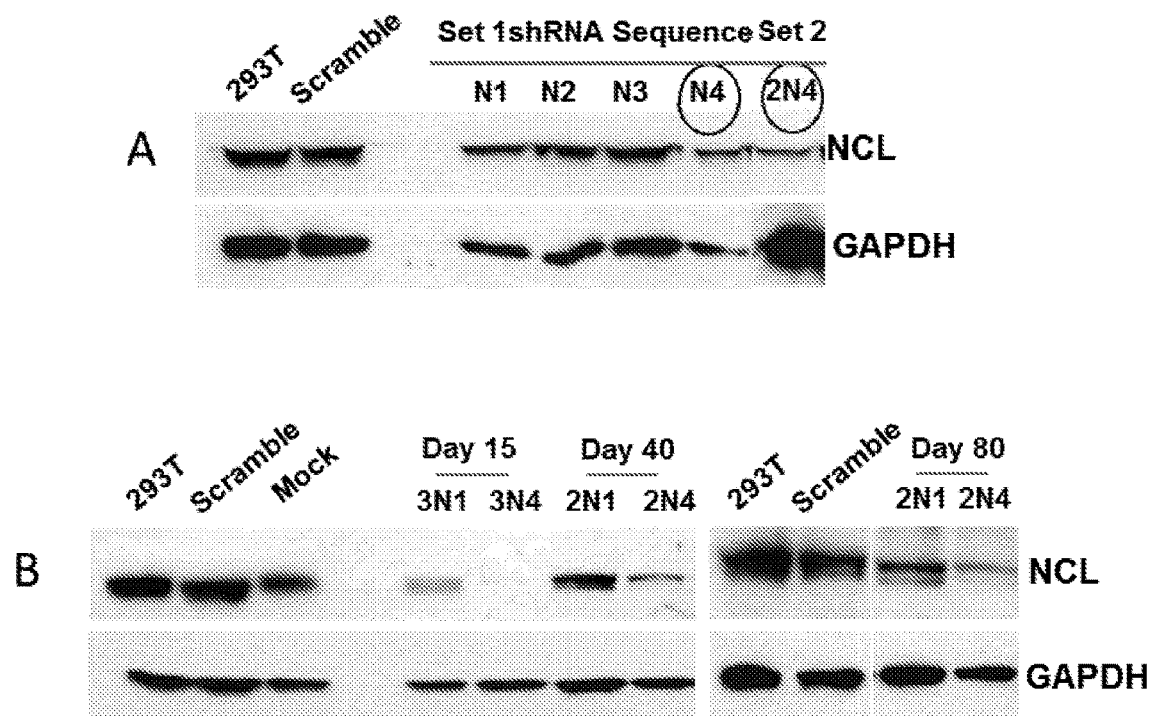
FIG. 9. Immunoblotting analysis of shRNA sequences targeting NCL. (A) Significant gene knockdown was observed in producer cells carrying shRNA N4, (B) down-regulation of NCL sustained for over 80 days after in culture. 293T cells with a shRNA sequence targeting non-mammalian genes (Scramble) and without any shRNA sequences (293T) were used as controls. Housekeeping gene GAPDH was further used as a loading control.

The 4 shRNA sequences targeting NCL gene, NCL-N1 to NCL-N4 (SEQ ID NOs: 9 to 12) showed a partial reduction of NCL expression, among which NCL-N1 and NCL-N4 had a greater effect (FIG. 9A, circled) and were thus selected for further study. The knockdown effect of NCL-N1 and NCL-N4 on NCL expression also sustained for over 80 days after cultured in puromycin selection medium (FIG. 9B) and after cryopreservation (data not shown).

Figure 10:
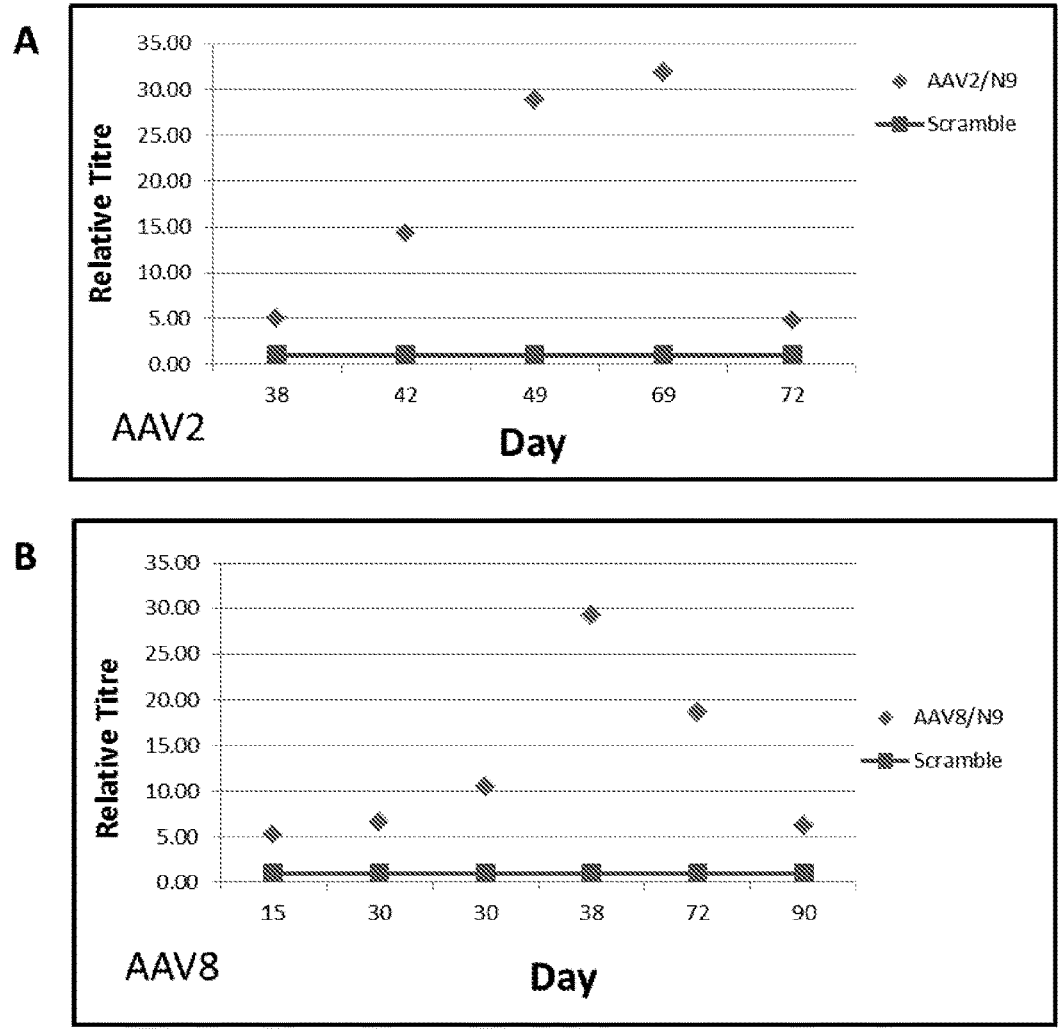
FIG. 10. Vector genome titres of AAV produced in NPM1 gene knockdown cells relative to control shRNA scramble, showing (a) up to 35 fold increase in AAV2 and (b) 30 fold increase in AAV8.

FIG. 10 shows that down-regulation of NPM1 with shRNA NPM1-N9 led to up to 35 fold increase in vector genome titres of AAV2/GFP (FIG. 10A) and up to 30 fold in AAV8/GFP (FIG. 10B), indicating an important role of NPM1 protein in AAV production. The up-regulating effect of NPM1 on vector genome titres showed chronological changes for both AAV2/GFP (FIG. 10A) and AAV8/GFP (FIG. 10B), with a maximum effect of an up to 30 fold increase observed in the knockdown producer cells in culture for around 40 days, and was sustained in producer cells for up to 90 after gene knockdown.

Figure 11:
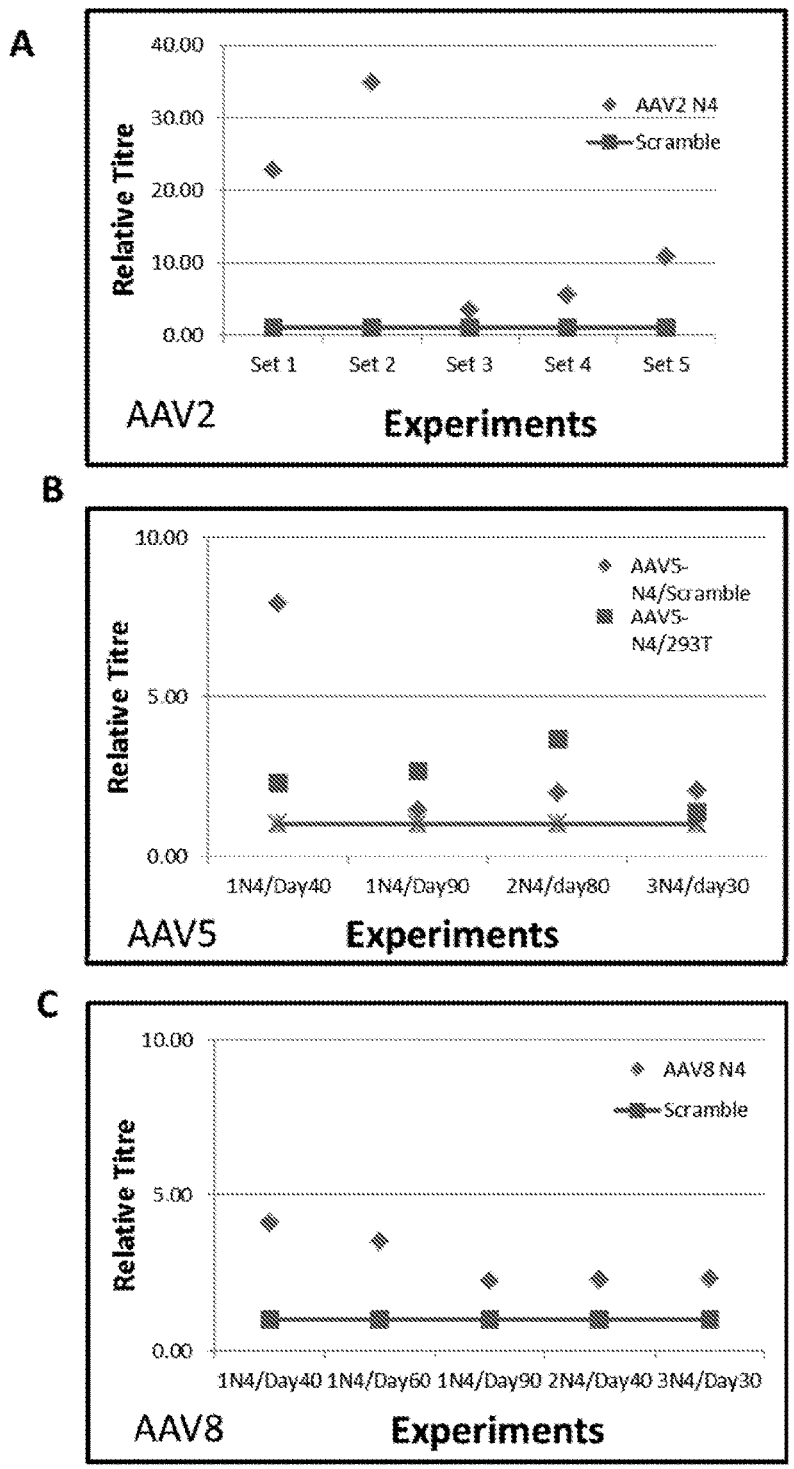
FIG. 11. Vector genome titres of AAV produced in NCL gene knockdown cells relative to control shRNA scramble, showing a significant variation, ranging from 2-40 fold increase in AAV2 genome titres (A), and lesser up-regulating effects on vector titres (up to 10 fold increase in AAV5 (B) and AAV8 genome titres (C).

Down regulation of NCL showed similar up-regulating effect on AAV2 vector production with up to 40 fold increases in AAV2 genome titres. However, there existed a significant variation, ranging from 2-40 fold, among different batches of producer cells (FIG. 11A). Gene knockdown of NCL had a lesser up-regulating effect (up to 10 fold increase) on AAV5 and AAV8 genome titres (FIGS. 11B and 11C, respectively) compared to AAV2. No significant chronological changes were observed from NCL knockdown producer cells (data not shown).

Example 6—CRISPR Knockdown of YB1

CRISPR genome editing was used to knockout or knockdown YB1 expression as an alternative to shRNA. The gRNA sequences used in this study were designed using the CRISPR/Cas9 programme (chopchop.rc.fas.harvard.edu/) targeting entire *Homo sapiens* chromosome 1 sequence (Accession number NC_000001.11) that includes YB1 gene sequence. Four pairs of gRNA sequences (A, B, C and D) (Table 4). were selected and a GeneArt CRISPR nuclease vector kit (Life technology, cat number A21174) was used to generate YB1 gRNA knockout producer cells.

Two batches (B1 and B2) of CRISPR gRNA knockout cells were produced for each of the four CRISPR gRNA sequences A, B, C or D. Single cell clones (C1 to C5) were further derived from the parental B1 and B2 gRNA producer cells for each gRNA pair. Parental 293T cells without any gRNA sequences (293T) were used as a control; Housekeeping gene GAPDH was further used for sample loading normalisation.

TABLE 4

YB1 CRISPR gRNA pairs

| gRNA pair | First sequence (5' to 3') | Second sequence (5' to 3') | Location |
| --- | --- | --- | --- |
| A | ATCGGCGGCGCCTGCCGGCGGTTTT (SEQ ID NO: 33) | CGCCGGCAGGCGCCGCCGATCGGTG (SEQ ID NO: 34) | within exon 1 of YB1 gene |
| B | GTAATGGCTTTTGTAGGGTGGTTT (SEQ ID NO: 35) | CACCCTACAAAAGCCATTACCGGTG (SEQ ID NO: 36) | within exon 5 of YB1 gene |
| C | GGACCATACCTGCGGAATCGGTTTT (SEQ ID NO: 37) | CGATTCCGCAGGTATGGTCCCGGTG (SEQ ID NO: 38) | within intron 6 of YB1 gene |
| D | CAAAGACAGCCTAGAAGGAGTTTT (SEQ ID NO: 39) | TCCTCTCTAGGCTGTCTTTGCGGTG (SEQ ID NO: 40) | within exon 7 of YB1 gene |

Figure 12:
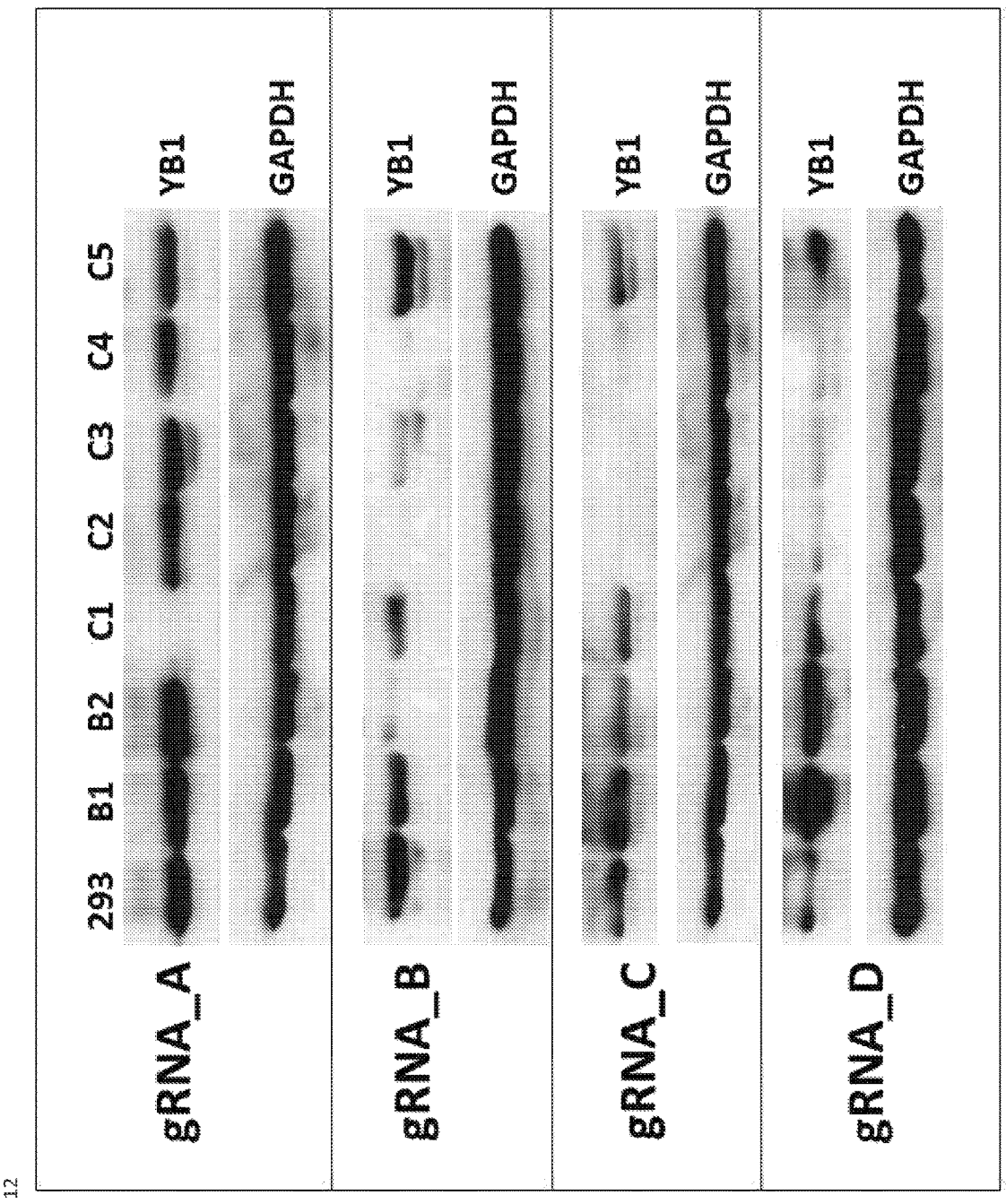
FIG. 12. Immunoblotting analysis of YB1 gene knockout using CRISPR gRNA sequences. Two batches (B1 and B2) of CRISPR gRNA knockout cells were produced for each of the 4 CRISPR gRNA sequences A, B, C or D. Single cell clones were further derived from the parental B1 and B2 gRNA producer cells. YB1 gene knockout was observed in a total of 10 single cell clones. Parental 293T cells without any gRNA sequences (293T) were used as a control; housekeeping gene GAPDH was further used as a loading control.

YB1 gene knockout was observed in a total of 10 single cell clones. FIG. 12 shows the effect on YB1 expression using these three gRNA pairs. Lanes labelled 293 refer to the 293 parental cell line. B1 and B2 are bulk knockout cells generated before single cell cloning. C1 to C5 are single cell clones generated from the bulk knockout cells.

As is clear from FIG. 12; gRNA pair A significantly inhibited YB1 expression in clonal cell line C1; gRNA pair B significantly inhibited YB1 expression in bulk knockout cells B2 and clonal cell lines C1 to C4, as well as observably inhibiting YB1 expression in bulk knockout cells B1; and gRNA pair C significantly inhibited YB1 expression in bulk knockout cells B2 and clonal cell lines C2 to C4, as well as observably inhibiting YB1 expression in clonal cell lines C1 and C5.

Example 7—Molecular Analysis of YB1 Knockdown Producer Cells

Figure 13:
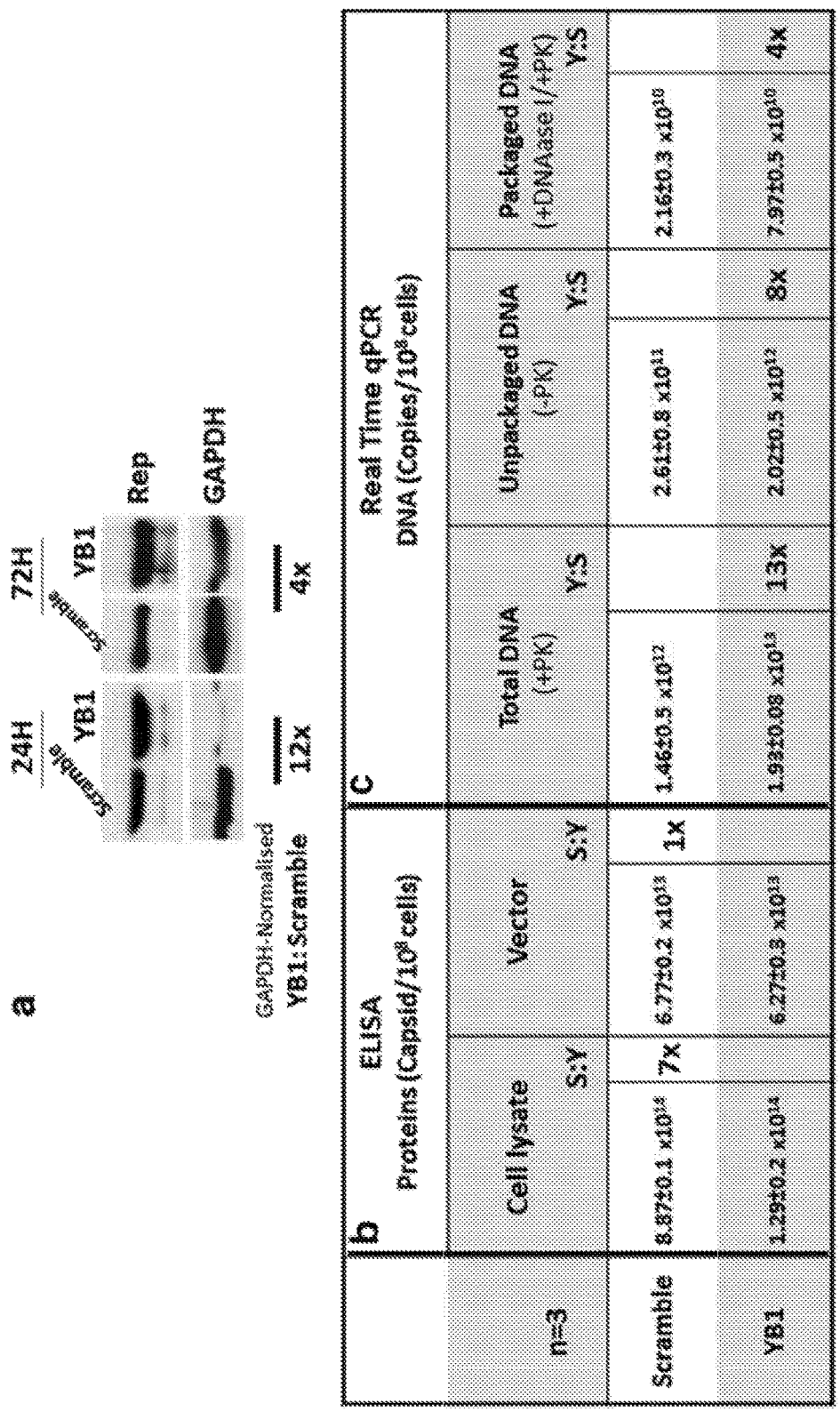
FIG. 13. Molecular analysis of YB1 knockdown cells for rep and cap expression and vector DNA production: (A) immunoblotting showing 12- and 4-fold increases in AAV2-Rep expression in YB1 knockdown cells 24 and 72 hours (H) after transient transfection, respectively; (B) ELISA showing a 7-fold decrease in cap expression in YB1 knockdown cell lysates compared to scramble cells and a comparable amount of Cap proteins detected in vectors harvested from YB1 and scramble cells and (C) real-time quantitative polymerase chain reaction (qPCR) showing 13× increase in total vector DNA, 8× increase in unpackaged vector DNA, and 4× increase in packaged vector DNA in YB1 knockdown cells compared to that in scramble cells. Y:S ratio between YB1 and scramble after being normalized by housekeeping gene GAPDH for immunoblotting or by cell numbers for qPCR analysis after being normalized by housekeeping gene actin. +PK, with proteinase K treatment; −PK, without proteinase K treatment; +DNaseI, with DNAse I treatment; S, control scramble; Y, YB1 knockdown cells.

In order to understand the molecular mechanism of YB1 influence on AAV production, AAV2 protein (Rep and Cap) expression and vector DNA production in YB1 knockdown cells was systematically analysed. FIG. 13A shows a 12- and 4-fold increase in rep gene expression in YB1 knockdown cells compared to that in scramble cells 24 and 72 hours after transient transfection, respectively, indicating a negative effect of native YB1 on rep gene expression. In contrast, the production of total AAV2 capsid proteins in YB1 knockdown cells ($1.29\pm0.2\times10^{14}$ capsids/$10^8$ cells) was ~7-fold lower than that in scramble cells ($8.87\pm0.1\times10^{14}$ capsids/$10^8$ cells) (FIG. 13B), indicating that the presence of native YB1 was beneficial for cap gene expression. Furthermore, the amount of capsid proteins in the harvested vector samples was comparable between YB1 knockdown cells ($6.27\pm0.3\times10^{13}$ capsids/$10^8$ cells) and scramble ($6.77\pm0.2\times10^{13}$ capsids/$10^8$ cells) cells (FIG. 13B), indicating that vector capsid particle formation may be independent of the amount of capsid proteins produced in the cells, and that there was a limit in the number of particles to be formed in cells.

DNA integration was systematically analysed using real-time qPCR targeting U6 sequence for YB1 shRNA integration, and targeting rep and CMV promoter sequences for AAV2 packaging plasmids pRep/Cap and phrGFP integration, respectively. There were $1.3\pm0.17\times10^8$ copies/$10^8$ cells of YB1 shRNA sequences detected in YB1 knockdown cells, equivalent to an average of one copy of YB1 shRNA per cell in pooled YB1 knockdown cells. Integration of AAV packaging plasmid pRep/Cap and phrGFP were comparable between scramble and YB1 knockdown cells, at ~$2\times10^7$ copies of Rep/Cap and ~$3\times10^7$ copies of phrGFP per $10^8$ cells.

To analyse the influence of YB1 gene knockdown on the production of AAV2 vector DNA, the copies of (1) total vector DNA that contains both packaged and unpackaged vector DNA, (2) unpackaged vector DNA, and (3) packaged vector DNA in YB1 knockdown cells 72 h after transient transfection of AAV packaging plasmids was systematically quantified using qPCR targeting vector-specific CMV sequence. Total vector DNA was prepared by removing plasmid DNA with benzenase, removing cell membranes and nuclei after sample freeze-thawing, and disassembling AAV capsid with proteinase K to release packaged vector DNA from the capsids. Non-integrated vector plasmid DNA may also contribute to the total vector DNA copies in cytoplasm; however, considering the transfection and production procedure was performed in parallel and was identical for both YB1 and scramble cells, the amount of plasmid DNA in cytoplasm should likewise be comparable and would not significantly alter the calculation of relative total vector DNA production. FIG. 13C shows that the copies of total vector DNA (+PK) were ~13-fold higher in YB1 knockdown producer cells ($1.93\pm0.08\times10^{13}$ copies/$10^8$ cells) than that in scramble cells ($1.46\pm0.5\times10^{12}$ copies/$10^8$ cells) indicating that YB1 gene knockdown promoted the vector DNA production.

Unpackaged AAV2 vector DNA was prepared in a similar way as that for total DNA samples except without proteinase K treatment (−PK) to release packaged vector DNA from AAV capsid. The copies of the unpackaged vector DNA were ~8× higher in YB1 knockdown cells ($2.02\pm0.5\times10^{12}$ copies/$10^8$ cells) than that in scramble cells ($2.61\pm0.8\times10^{11}$ copies/$10^8$ cells) (unpackaged DNA, FIG. 13C). Packaged AAV2 vector DNA, representing physical vector genome titres, was prepared by the addition of DNAse I treatment (+DNAse I) to remove unpackaged vector DNA in cytoplasm followed by proteinase K treatment (+PK) to release the packaged vector DNA from capsids. The copies of packaged vector DNA (+DNAse I/+PK, FIG. 13C) were 4-fold higher in YB1 knockdown cells ($7.97\pm0.5\times10^{10}$ copies/$10^8$ cells) than that in scramble cells ($2.16\pm0.3\times10^{10}$ copies/$10^8$ cells) (FIG. 13C). It should be noted that in this particular set of molecular studies, we observed a 4-fold (significant) increases in AAV2 vector genome titres in YB1 knockdown cells compared to that in scramble cells.

In summary, the significant difference observed among the fold changes in total vector DNA (13× increase), unpackaged (8× increase), and packaged vector DNA (4× increase) underlined a potential for the improvement of AAV vector DNA packaging in YB1 production system. Moreover, taking into consideration that the amount of capsid proteins was comparable (FIG. 13B) but the copies of packaged DNA (FIG. 13C) was 4-fold higher in the same batch of harvested vector samples from YB1 knockdown cells compared to that from scramble cells, the results revealed a considerable advantage of YB1 gene knockdown in reducing the number of empty particles in AAV products.

DISCUSSION

The present inventors have demonstrated for the first time an important role of YB1 in AAV vector production. Introducing the shRNA sequence Y4 that targets and down-regulates YB1 gene to AAV producer cells resulted in up to 50 and 10 fold increase in vector genome titres of AAV2 and AAV8, respectively. Molecular characterization of YB1 knockdown cells showed an ~12-fold increases in rep expression, an ~13-fold increase in vector DNA production, and an ~7-fold decrease in cap expression in YB1 knockdown cells compared to scramble cells, uncovering a significant role of the YB1 gene in AAV biology.

YB1 is a DNA and RNA-binding protein involved in almost all DNA and mRNA-dependent processes. YB1 packs and stabilizes mRNA to mediate gene regulation at different levels. YB1 binds to both double-stranded DNA (dsDNA) and single-stranded DNA (ssDNA), but has a far higher binding affinity to ssDNA. It has been suggested that YB1 prevents binding of activating proteins by stabilising ssDNA in the region of promoters or enhances in a sequence-specific manner. In particular, YB1 has highest binding affinity to the ss-DNA motif GGGG(TT). Analysis of the AAV2 ssDNA genome showed that such a single-stranded GGGG(TT) motif is presented within the AAV2 ITR region from nucleotide 137 to 142 of the AAV2 genome (NCBI sequence NC_001401.2), indicating a potential AAV DNA binding site for the YB1 protein. ITR deletion mutagenesis showed that the 20 nucleotide D sequence (from nucleotide 126-146), which covers the single-stranded GGGG(TT) motif and immediately follows the 125 nucleotide long hairpin, is required for the encapsidation of the AAV DNA genome and has thus been proposed as packaging signal for AAV; in particular, the N-terminal region of AAV capsid proteins binds to the D sequence resulting in the encapsidation of AAV ssDNA into preassembled AAV capsid. Therefore, the capability of both YB1 and AAV capsids for binding to the ITR D sequence region may impose competition between YB1 and AAV capsids and compromise encapsidation of AAV genome.

Analysis of the genome of AAV serotype 2 (AAV2) by the present inventors has shown that this GGGG(TT) motif is present within the inverted terminal repeat (ITR) region from positions 137 to 142 of the AAV2 genome (NCBI sequence NC_001401, version NC_001401.2 GI:110645916). This indicates a potential binding site for YB1 to the AAV2 genome. The present inventors have generated chimeric forms of the AAV5 and AAV8 serotypes comprising the AAV2 ITR (but with the AAV5 and AAV8 capsid proteins respectively). Therefore, if the GGGG(TT) motif was the sole binding site for YB1, it would be expected that YB1 would have a similar effect on virus particle production for AAV2 and the chimeric forms of AAV5 and AAV8. However, the present inventors have demonstrated there was a significant difference in the AAV vector titres relative to the scramble controls among the AAV2, AAV5 and AAV8 vectors produced in YB1 knockdown cells. In particular, the present inventors found that there was a 50-fold increase in AAV2 vector titre in producer cells with YB1 knockdown, compared with a 10-fold increase in AAV8 titre and no significant increase in AAV5 titre. This suggests that there may also be some AAV capsid protein-specific element to the effect of YB1 knockdown on AAV vector production, as well as the DNA sequence-specific effect.

There are three YB1 domains, namely A/P, CSD and CTD, which are involved in protein-protein interaction. In particular, YB1 protein is known to interact with important regulatory proteins, such as p53, Akt kinase, hnRNP K and TATA-binding protein. YB1 is also known to play an important role in the replication of a number of viruses by binding to viral proteins, such as HIV TAT, the large T antigen of polymavirus, Hepatitis C Virus (HCV) protein NS3/4A and influenza ribonucleoprotein (RNP). Indeed, shRNA knockdown of YB1 has been shown to result in a reduction of HCV titres of up to 80%. In that study, it was found that knockdown of YB1 did not influence the expression of viral proteins, nor the production and stability of viral RNA, indicating that the knockdown of YB1 disrupted the formation of the YB1-NS3/4A vRNA interactome required for recruiting core proteins for virus assembly.

The role of YB1 in adenovirus replication is particularly relevant to the understanding of the inventors' findings that down-regulation of YB1 significantly improved AAV production by as much as 50-fold. The interaction of adenoviral protein E1B with YB1 in adenovirus-infected cells has been shown to result in the accumulation of YB1 in nuclei, YB1 activation of the E2A gene, and subsequently the initiation of adenoviral DNA replication. Overexpression of YB1-regulated adenoviral E2 promoter in an E1-independent manner led not only to adenoviral DNA replication but also a 2-3-log increase in the production of infectious particles from E1-deleted adenovirus vectors. As a result, overexpression of YB1 has been further exploited in adenovirus-based vector development and virotherapy.

So far there has been no direct association of YB1 reported with AAV virus; however the role of adenovirus in the AAV life cycle has been well documented and this may facilitate understanding the mechanism behind the enhancement of YB1 knockdown on AAV vector production. The AAV production system used in the present Examples provide four Adenoviral elements, i.e. E1, E2A, E4 and VA genes that were expressed either stably in the producer cells or transiently from a plasmid with helper function for AAV. Open-reading frame 6 of the E4 region is important for the conversion of the single-stranded AAV genome into a double-stranded form which is the substrate for subsequent steps in DNA replication. Protein E2A plays a key role in viral DNA replication via binding to AAV viral DNA, promoting DNA elongation and displacement of the elongating strand from its template. Both YB1 and E2A are DNA binding proteins (DBP) but differ from each other by their cellular and viral origins respectively. YB1 and E2A share a comparable binding preference for single stranded DNA. It is possible that adenoviral E2A has a prime regulation property over cellular DBP in the AAV life cycle; therefore, down-regulation of YB1 would reduce the competition of YB1 binding to AAV DNA, resulting in the enhancement of E2A-AAV DNA interaction, the efficiency of AAV DNA replication and ultimately increase in AAV vector genome titres. This speculation could be supported by the observation that cells lacking AAV helper components including E2A could still produce small amount of AAV particles, indicating a low level of cellular helper function from abundant but less efficient cellular DBPs, e.g. YB1 in the AAV life cycle.

On the other hand, adenoviral proteins E1A-E1B and E2A play an important role in activating AAV2 p5 promoter, resulting in the transcription and expression of the AAV2 rep gene. It has previously been demonstrated that binding of YB1 to the vascular endothelial growth factor promoter prevented the binding of other transcription factors and resulted in the inhibition of transcription and translation. It has also been shown that YB1 binding to the ssDNA region of a promoter resulted in the stabilization of ssDNA that also inhibited gene transcription and translation. Therefore, it is possible that down-regulation of YB1 promoted E2A binding to the AAV2p5 promoter that synergistically contributed to the significant increase in AAV Rep gene expression and vector titres observed in this experiments reported herein.

The present Examples show a serotype-specific role of YB1 in AAV production; in particular, knockdown of YB1 improved AAV2 and AAV8 production by 50 and 10 fold respectively but had no significant effect on AAV5 production. The three serotypes of AAV vectors investigated, i.e. AAV2, AAV5 and AAV8, have an identical ITR sequence that shares the potential YB1 binding motif GGGG(TT) and were produced in the presence of the same helper elements from Adenovirus. AAV2 and chimeric AAV8 vectors further share the same AAV2 rep gene sequence in the Rep/Cap packaging plasmids. In terms of differences among the three serotypes of AAV2, AAV5 and AAV8 vectors, the serotype-specific cap gene sequences contribute to one of them. AAV2 and AAV8 capsid proteins share more than 82% homology in their primary sequence and a much similar overall topology in the structure of capsid proteins. The notable structural differences between AAV2 and AAV8 capsid proteins are located on the capsid surface and are known to be associated with the binding property of AAV2 and AAV8 to target cells rather than being involved in capsid assembly and genome packaging, further demonstrating the similarity between AAV2 and AAV8 in terms of capsid assembly. In contrast, AAV5 is one of the most divergent AAV serotypes, sharing only ~55% sequence homology to other serotypes, including AAV2 and AAV8. Unique structural features of AAV5 capsid proteins, including a smaller HI and VR-IV loop and larger VR-VII, are located in the VP region that controls the specificity of capsid assembly, genome packaging, and antigenic determinants, and may explain the observed difference in AAV2 and AAV8 vector production. The results disclosed herein also show that YB1 gene knockdown resulted in up to 12- and 13-fold increases in rep gene expression and vector DNA production, respectively, and a ~7-fold decrease in cap gene expression, underlying the molecular mechanism of YB1 influence on AAV vector production.

Another significant difference is that the AAV5 has rep gene shares only 58% homology with AAV2 rep gene in AAV2 and AAV8 vectors. Further sequence analysis showed that AAV2 and AAV5 use different promoters, i.e. p5 and p7 for rep transcription and translation of AAV2 and AAV5, respectively. It has been shown that due to the efficiency of p7 in rep gene expression, the AAV5 p7 promoter is less dependent in 293 cells on Ad5 elements when compared to the AAV2 p5. On the other hand, Adenoviral proteins E1A-E1B and E2A play an important role in activating AAV2 p5 promoter, resulting in the transcription and expression of AAV2 rep gene. There have been a significant number of reports on the mechanism of YB1 regulation on cellular and viral promoters. For example, binding of YB1 to the VEGF promoter prevents the binding of other transcription factors and results in the inhibition of transcription and translation. It has also been shown that YB1 binding to the ssDNA region of a promoter resulted in the stabilisation of ssDNA that also inhibited gene transcription and translation. Therefore, it is possible that down regulation of YB1 promoted E2A binding to the AAV2p5 promoter that synergistically contributed to the significant increase in AAV2 and AAV8 titres which we observed.

Taking into account the potential roles of YB1 in DNA replication, AAV transcription and translation, it is possible that deregulation of YB1 resulted in not only the increase in AAV DNA replication via reducing YB1 competition with E2A for AAV2 ssDNA e.g. the ITR sequence, but also the increase in Rep and Cap expression under the control of the AAV2p5 promoter. In addition, the native AAV2p5 promoter in AAV2/2 vectors may perform more effectively compared to the chimeric AAV2/8 Rep/Cap in the expression of Rep and Cap proteins, caused the observed 50 and 10 fold increase in AAV2 and AAV8 production, respectively. In the case of AAV5 vectors, vector DNA replication may likewise be increased via a similar competition-based mechanism as for AAV2 and AAV8; however, the low level of AAV5 Rep/Cap expression under the control of the AAV5p7 promoter that is less dependent on combined YB1 and Adenoviral helper function, may have limited the excess AAV vector genome to be packaged into full AAV5 vectors, resulting in the accumulation of AAV vector DNA in producer cells.

In summary, the present inventors have identified using LC-MS/MS and validated using immunoblotting the association of YB1 with AAV vectors and, revealed for the first time the significant enhancement of YB1 gene knockdown on AAV vector production. The significant increase in AAV2 vector titres may be due to a significant increase in rep gene expression and vector DNA production in YB1 knockdown cells compared to scramble cells. Although there has been no direct involvement of YB1 in the AAV life cycle has been reported, it is speculated that YB1 exerts negative effects on AAV production, including the blockage of AAV vector DNA replication. This may be mediated by competition with E2A for binding to the ITR sequence and AAV2p5 promoter, inhibiting the transcription and expression of AAV viral proteins (such as AAV rep proteins) by binding to the AAV2p5 promoter and by preventing the binding of activating proteins, e.g. E2A. It is possible that effects of YB1 on AAV are adenoviral helper virus dependent.

The invention claimed is:

1. A transgenic producer cell line in which the expression of Y Box-Binding Protein (YB1) is reduced compared with a control producer cell line.

2. The transgenic producer cell line of claim 1, wherein the expression of: (i) YB1 and nucleophosmin (NPM1); (ii) YB1 and nucleolin (NCL); or (iii) YB1, NPM1 and NCL is reduced compared with a control producer cell line.

3. The transgenic producer cell line of claim 2, wherein the expression of NPM1 and/or NCL is reduced using CRISPR genome editing, a double stranded RNA (dsRNA), a small interfering RNA (siRNA), a small hairpin RNA (shRNA), a micro RNA or an antisense RNA.

4. The transgenic producer cell line of claim 3, wherein:
(a) NPM1 expression is reduced using a shRNA comprising a nucleotide sequence selected from SEQ ID NOs: 4 to 8 (NPM-N6 to NPM-N10); and/or
(b) NCL expression is reduced using a shRNA comprising a nucleotide sequence selected from SEQ ID NOs: 9 to 13 (NCL-N1 to NCL-N5).

5. The transgenic producer cell line of claim 3 wherein the expression of NPM1 and/or NCL is reduced using CRISPR genome editing.

6. The transgenic producer cell line of claim 1, wherein the expression of YB1 is reduced using CRISPR genome editing, a double stranded RNA (dsRNA), a small interfering RNA (siRNA), a small hairpin RNA (shRNA), a micro RNA or an antisense RNA.

7. The transgenic producer cell line of claim 6, wherein the expression of YB1 is reduced using a shRNA, wherein the shRNA comprises a nucleotide sequence selected from SEQ ID NOs: 14 to 18.

8. The transgenic producer cell line of claim 6, wherein the expression of YB1 is reduced using CRISPR genome editing.

9. The transgenic producer cell line of claim 6, wherein the expression of YB1 is reduced using a gRNA pair selected from SEQ ID NOs: 33 and 34; SEQ ID NOs: 35 and 36; SEQ ID NOs: 37 and 38; and/or SEQ ID NOs: 39 and 40.

10. The transgenic producer cell line of claim 1, wherein the expression of one or more additional genes and/or proteins listed in Table 2 is modulated compared with a control producer cell line.

11. The transgenic producer cell line of claim 1, which is a human embryonic kidney 293T cell line.

12. A method for producing an adeno-associated viral (AAV) vector comprising culturing an adeno-associated virus in the producer cell line of claim 1; and producing the AAV vector.

13. The method of claim 12, wherein the expression of: (i) YB1 and NPM1; (ii) YB1 and NCL; or (iii) YB1, NPM1 and NCL in the producer cell line is reduced.

14. The method of claim 12, wherein the expression of YB1, NPM1 and/or NCL is reduced using CRISPR genome editing, a double stranded RNA (dsRNA), a small interfering RNA (siRNA), a small hairpin RNA (shRNA), a micro RNA or an antisense RNA.

15. The method of claim 14, wherein the expression of YB1, NPM1 and/or NCL is reduced using a shRNA.

16. The method of claim 15, wherein:
(a) YB1 expression is reduced using a shRNA comprising a nucleotide sequence selected from SEQ ID NOs: 14 to 18 (Y1 to Y5);
(b) NPM1 expression is reduced using a shRNA comprising a nucleotide sequence selected from SEQ ID NOs: 4 to 8 (NPM-N6 to NPM-N10); and/or
(c) NCL expression is reduced using a shRNA comprising a nucleotide sequence selected from SEQ ID NOs: 9 to 13 (NCL-N1 to NCL-N5).

17. The method of claim 14, wherein the expression of YB1, NPM1 and/or NCL is reduced using CRISPR genome editing.

18. The method of claim 17, wherein the expression of YB1 is reduced using a gRNA pair selected from SEQ ID NOs: 33 and 34; SEQ ID NOs: 35 and 36; SEQ ID NOs: 37 and 38; and/or SEQ ID NOs: 39 and 40.

19. The method of claim 12, wherein the expression of one or more of the additional genes and/or proteins listed in Table 2 is modulated in the producer cell line.

20. The method of claim 12, wherein the titre of AAV vector is increased at least 2 fold compared with the titre of AAV vector produced by a control method.

21. The method of claim 12, wherein the ratio of complete:empty AAV vector is increased by at least 20% compared with the ratio of complete:empty AAV vector produced by a control method.

22. The method of claim 12, wherein the producer cell line is a human embryonic kidney 293T cell line.

23. The method of claim 12, wherein the serotype of the AAV vector is AAV2, AAV5 or AAV8.

* * * * *

SEQUENCE LISTING

<160> NUMBER OF SEQ ID NOS: 40

<210> SEQ ID NO 1
<211> LENGTH: 1331
<212> TYPE: DNA
<213> ORGANISM: Homo sapiens

<400> SEQUENCE: 1

```
ggggcctggt gtgattccgt cctgcgcggt tgttctctgg agcagcgttc ttttatctcc      60
gtccgccttc tctcctacct aagtgcgtgc cgccacccga tggaagattc gatggacatg     120
gacatgagcc ccctgaggcc ccagaactat cttttcggtt gtgaactaaa ggccgacaaa     180
gattatcact ttaaggtgga taatgatgaa aatgagcacc agttatcttt aagaacggtc     240
agtttagggg ctggtgcaaa ggatgagttg cacattgttg aagcagaggc aatgaattac     300
gaaggcagtc caattaaagt aacactggca actttgaaaa tgtctgtaca gccaacggtt     360
tcccttgggg gctttgaaat aacaccacca gtggtcttaa ggttgaagtg tggttcaggg     420
ccagtgcata ttagtggaca gcacttagta gctgtggagg aagatgcaga gtcagaagat     480
gaagaggagg aggatgtgaa actcttaagt atatctggaa agcggtctgc ccctggaggt     540
ggtagcaagg ttccacagaa aaaagtaaaa cttgctgctg atgaagatga tgacgatgat     600
gatgaagagg atgatgatga agatgatgat ggtgatgatt ttgatgatga ggaagctgaa     660
gaaaaagcgc cagtgaagaa atctatacga gatactccag ccaaaaatgc acaaaagtca     720
aatcagaatg gaaaagactc aaaaccatca tcaacaccaa gatcaaaagg acaagaatcc     780
ttcaagaaac aggaaaaaac tcctaaaaca ccaaaaggac ctagttctgt agaagacatt     840
aaagcaaaaa tgcaagcaag tatagaaaaa ggtggttctc ttcccaaagt ggaagccaaa     900
```

```
ttcatcaatt gtgtgaagaa ttgcttccgg atgactgacc aagaggctat tcaagatctc        960
tggcagtgga ggaagtctct ttaagaaaat agtttaaaca atttgttaaa aaattttccg       1020
tcttatttca tttctgtaac agttgatatc tggctgtcct ttttataatg cagagtgaga       1080
actttcccta ccgtgtttga taaatgttgt ccaggttcta ttgccaagaa tgtgttgtcc       1140
aaaatgccgt ttagttttta aagatggaac tccacccttt gcttggtttt aagtatgtat       1200
ggaatgttat gataggacat agtagtagcg gtggtcagac atggaaatgg tggggagaca       1260
aaaatataca tgtgaaataa aactcagtat tttaataaag tgaaaaaaa aaaaaaaaaa       1320 aaaaaaaaa a                                                            1331

<210> SEQ ID NO 2
<211> LENGTH: 10942
<212> TYPE: DNA
<213> ORGANISM: Homo sapiens

<400> SEQUENCE: 2
attctgctgt agacatagag atgatgatca tagctgacta tgatgatgat cccccgcgag         60
cctgaaagag gaaatgctct ggtttgctaa gcccgcgaat cgagtgagac ccacccacaa        120
agctaaccgt ggaagtcact ggcggcctcc ttcgccctgc cagccgggga acccatccgg        180
tggctctcga cctgctcccg ggccatctgg tgacactgac ttcgcagcca ccacttaat         240 tggcgcattc gacccaaata ataacctggg aacctgtggg cggtctaagg cccggctctg        300
cggtcgccct cccaggcccc ctccctggcc ctgtgaggc cagaaagtta cttctccgag        360
gccagttccc catgtctgag aaatatctcc caacttgagg ttctgtgggg taggggaggg        420
ttcgtgactt tctcacagaa aacctcgtac agaccccgcc actgccttta ttaacagctc        480
tcaggagact gcctgcagga gggggtcgc tccggcccca tgctcgcggg caagcaggga        540
taagctgtgc ctccaaaagg gccaacggga actccgcggt ccctgaactt ccggtgctgg        600
aggactcctc gctccagggc caccaggagc gcggcgtga gtgcgtgccg gaaccgaggg         660
cggggtctct gaggaactcc aaggctgccc aagcctacgg acccagccac attggcgaac        720
cggagaccgc ccgattccac cacccccgcg ctcccctcac agccggcgcc aaaaacgcca        780
gtcccacgac gcaggccggg acccgcgcgc ccacggccca atcagcgcga ccttgcacaa        840
agcgagcccc gccccacgg cgccgttgcc agccctcc cctcccgtgc cgcctcggcc          900
cgcctactcc ccgccccgcg ccgttcacgg ttagaggctc gcgattggct catggggacg        960
gccgcgagct ttggttggtc ggcgcggagt cacgaggcgc cgtcgtcgcc tttccacagg       1020
cgttactggg caggctcagt ctttcgcctc agtctcgagc tctcgctggc ttcgggtgta       1080
cgtgctccgg gatcttcagc acccgcggcc gccatcgccg tcgcttggct tcttctggac       1140
tcatctgcgc cacttgtccg cttcacactc cgccgccatc atggtgaagc tcgcgaaggt       1200
aaacggcctt gagcgcgacg cagacgtgta ggcctgcttc cgagggggcga gcgcggcgcc       1260 gcggggagga gggcctgcgc gcagtcccgg gcgcgttcta gggcgccatg ctgcgggaag       1320
tctcgcgcga ttagtgggga ggtctcgcgc ttctggctac ttggtggcga ggtgaagagc       1380
ttctgcaggt gctgggggag ggggcgctgg gcctcgggt ggagagatga gaccaaactt       1440
ttgcgacgcg tacgagctgg gactgactct gacgcacgtg cccgggagcg tgcctgccac       1500
gtgggccgga gtaggtctgg aatctccaga gggaccgggt gccttgggcc gggaaatggc       1560
ggtatcggcc ctagtcggag tcccggctgc gctcggatgt ctccgccccg gcctggcaag       1620
ccgatacgtg gtgggccccg gaaggtggct ctgccgcgtg ccttttgcgc tgtgtttcgg       1680
```

```
gcaagaggtg gtcctgccag gtaccccac gtggccgcac ccgcctcttt aagggggcggg    1740 gtagtgctgg ggaaaggcat aagcttcatg agaaaataag gtagtatttt taagtgcctt    1800
aatgatcttc accgttaatt tgattcaaat aagggtggta gataaagtac cgggatttgt    1860
agtataaaaa cacggttgtg cttaactaag gtaacgggag gagaaatcat ttcctcaggt    1920
tgacttttta ccttagggca ggttttctgt tggtaaagcc tgggaggaaa aatgtgggcg    1980
gttgagaagt agtccctctt gcattgccat caggagtagt ttctatgtta gttgtggtgt    2040
ttggcactat gagaaatgat ctgagacgga gatgatggcg tatgaacact aatggcaaaa    2100
tatgaatggc ctgaaatgtc gaggtggagg tgtaatgatc tatttgtgtc cattttaggc    2160
aggtaaaaat caaggtgacc ccaagaaaat ggctcctcct ccaaaggagg tagaagaaga    2220
tagtgaagat gaggaaatgt cagaagatga agaagatgat agcagtggag aagaggtaat    2280
tttatccaac ttaatgcaga attatgttaa aactacaaaa tggagagtta agacatgaaa    2340
ttggatatct gtggcaaaaa taagatttta tcaggtatgt cttattgtag tggttgagtg    2400
tttcacaagc tcttcattga catgtcaaga tgtcatttgg ctagtatttg aatgtgagtg    2460
ctaagacgag actgggaatt tcttttacat gttcctctgc agggcttgga gtgtgatttg    2520
ttgtgttaaa tcattacatt tttccagttt caacatgtta gctcaccccc acatgtagag    2580
ctgggcattg tattcagagc tgagaataac cttaccagat tcctttccta tcctccgaat    2640
taaaattaat tggtctccat tccatatata tataactgta tcactactgg ttaagtactc    2700
gggtgtagac tgagggctgc cacctctctt tggtaccatt gaccctcttt agccacctcc    2760 tggccttta tttgcctcca ctataaagac agctgagcac tgaattgtgc tcaggttttc    2820
gttgagaacc tgaatgaaag ttttactctc cacacattgc cttgataaaa ctacgggatt    2880
ttaatgtagc taaatgatga ctttatcaa actaccatgc acactctttg atgtgtgata    2940
gttttgtaag gaatatttat atttagccta ttcattttt gtctcaggtc ctaagaattg    3000
agcttcactg ggcttggtgg accgcaacca cgagggcccc aatgatttaa taagttaatg    3060
cttggagcct cctatgtgta acgttctgaa taatttacac atagcaattc atgaccttaa    3120
acatgtaagg atgatactat taccattttc agatgagaaa gttggggctt gggaaagtat    3180
gaggtgtaag aattcagagg gtctggttca gaggtatttt cagtgttcaa aagagttcct    3240
tatgtctggg tattcacctt attataggg ctctgactta agacaacata acagaagcct    3300
ggagttttaa catgtcatat gtgtcatgcg tatgtcttga accagaggca ttgccagagt    3360
ctaacaactc attgggacca tggttatctt tttgggtgtg gggctggact tactggtttg    3420
gttttcattt atctcaaggt cgtcatacct cagaagaaag gcaagaaggc tgctgcaacc    3480
tcagcaaaga aggtggtcgt tccccaaca aaaaaggttg cagttgccac accagccaag    3540
aaagcagctg tcactccagg caaaaaggca gcagcaacac ctgccaagaa gacagttaca    3600
ccagccaaag cagttaccac acctggcaag aaggagccca caccaggcaa agcattggta    3660
gcaactcctg gtaagaaggg tgctgccatc ccagccaagg gggcaaagaa tggcaagaat    3720
gccaagaagg aagacagtga tgaagaggag gatgatgaca gtgaggagga tgaggaggat    3780
gacgaggacg aggatgagga tgaagatgaa attgaaccag cagcgatgaa agcagcagct    3840 gctgccctg cctcagagga tgaggacgat gaggatgacg aagatgatga ggatgacgat    3900
gacgatgagg aagatggtaa ggagttgtct tggtagttac tgggcttctg attacaaggt    3960
atcttgagat tctgggatca catattcctt catcgtacaa cctggagatg agattagaat    4020
```

-continued

```
cttgtgggaa ttctcttggg ttgttgtggt gtgctagact taattaccca tgaatgattt      4080
tgtcctcttg agaaaatttc aatagcacat ctattagtgt tttttataat gtaggatttt      4140
cgtttctaag tgattttttt ttttttttaa attttttga gatggagctt ttgctgtttc        4200
ccaggcggga gtgcaatggc gcgctatctc ggcgcactgc agcctccatc tcctgggttc      4260
aagcagttct gcctcagcct cccgagtagc gggattacag gtgcccacca ccacaccta       4320 ctaattttgt attttagtag agacgacatt tcaccatgtt ggccaggctg gctctgaact      4380
ttgacctcag gtgatccacc caccttaggc tctcccaaag tgctaggatt acaggtgaga      4440
tatgctgcgc ccggcccaa gtgatctatt cttgccatga ctgttaacta acatggtga       4500 caggattcga ttttctttac attagatttg aaaaccgatg ttggttttgg gagattgctg      4560 caattttag gtgacttctc tttcagactc tgaagaagaa gctatggaga ctacaccagc       4620
caaaggaaag aaagctgcaa aagttgttcc tgtgaaagcc aagaacgtgg ctgaggatga      4680
agatgaagaa gaggatgatg aggacgagga tgacgacgac gacgaagatg atgaagatga     4740
tgatgatgaa gatgatgagg aggaggaaga agaggaggag gaaggtactt aaattagatt     4800
ctgacatacg acatgagtta tgtttaaagg aggcacttaa gtgtttgtgg ctactgatgt      4860
gtgatacatt gtttgacatc ttgtccagag cctgtcaaag aagcacctgg aaaacgaaag    4920
aaggaaatgg ccaaacagaa agcagctcct gaagccaaga aacagaaagt ggaaggtaac    4980
ttgcagaatt aggggatatg ggggagataa acagcacaaa tgatgaataa caagggact     5040 taatactgaa accagatgtt acattgtagt gtgctgatgt gctgtgtata gaaattttgc     5100
tttgaaaact aacttttac cacactacaa gtagactgag ttgagctttt tttgtgcagg     5160
cacagaaccg actacggctt tcaatctctt tgttggaaac ctaaactta acaaatctgc     5220 tcctgaatta aaaactggta tcagcgatgt ttttgctaaa aatgatcttg ctgttgtgga    5280
tgtcagaatt ggtatgacta ggtagctgct tcactgcacg ttacataccg tgggtctgtt     5340 aattttcct tcccctgtta gcacagttac tttagcctgc cactgttaaa catgaatact      5400
gtaaacactt caaggttagc attagtgaac taagttagaa ttaaactgta gatcccctaa    5460
gttgcaattt ccataatcag tcgtaacttg gtatagcaca gaataatttt tagtaatttt     5520
tttgttgttt ttgttatgta ttgagacgga cgctggcttt tgttcaggct ggagtacagt    5580
ggcgcaatct tggctcactg caacctctgc ctcccgggtt caagcgattc tcctgcctaa    5640
cctcccaagt gactgggata cgggtgccac tcaccatgca tggctaattt ttgttttgta    5700
tttagtatcg atttcaccat gttggtcggc tggttttgaa ctcctgacct caagtgatcc    5760
acccacctcg gcctctcgaa gtgctggtac agcgtcacca ccctgccagt aagttttaat   5820
aatttggtgt taggtgggag aatgcttgaa cctgggaggc agaggttgca gtgagccaag    5880
ttcgcgccac tgtactccag cctgggcaac agattgagac accgtctcaa tttaaaataa    5940
tgtttatttt cttggaagta ccttgaaact attagacctg tctagtcatc atagtgaata    6000
cttttatcca gacaggattc tcctgtatta gtgcttatag gtgttctttt gtcagctgct     6060
actgtgaatt cttataagca atttagctcc atgatgaaga cctcaaacgt gaatgtgcat    6120
gtcatatctt catgctgagc cgtgttctgt agctgcagtt tgcagagcct tgactttgtt     6180
ttgctatact aggggtgctt tttaaaatgt gatctttgtt tgcaccatca catttgtcta    6240
gatacagatt gtgattttga tttgtgtttt cacctgttgt aattttgccc tcctctccac    6300
ctgaaggaaa tttggttatg tggattttga atctgctgaa gacctggaga aagcgttgga   6360
actcactggt ttgaaagtct ttggcaatga aattaaacta gagaaaccaa aaggaaaaga    6420
```

```
cagtaagaaa ggtatgtaag gctttatgag ttatgcaatg aactcaggag ctagactgct   6480
agggaaaatg ctttgtaacc catttccctt tggtttcctc ttatttttt taaatcattt    6540 ttttcctttg gtttcctctt aatgtgggaa ttaaatgagc tacagtgttt acaaggtact   6600
tggcactgct tgtcagtgta taggtaaatt cctgagttag gcaagcaaga gcactcttat   6660
acagaacaag aaccattaca tgcacctaaa ttaagctaag gatctttctt cactgaaact   6720
agttaggtcc ctaattactc cctatataca gtgtaatgtt ttgaattggt acattcactt   6780
tttttgttat gcgcgtctac tctaggttga actccagtgt acctaacaga gagtttgaca   6840
tcaaggctgt gacaacatgg agggaccact tgtgtgttga cactgctata tctccatatt   6900
tagcaccgag ccttgtacat ataggatctc aaattatttg ttgatagagc tatgtgtgtt   6960
tttcccctct ttttgttgtt gccccccacc tttggttttt caggccacag agctcatttt   7020
tgttttttta atctagagcg agatgcgaga acacttttgg ctaaaaatct cccttacaaa   7080
gtcactcagg atgaattgaa agaagtgttt gaagatgctg cggagatcag attagtcagc   7140
aaggatggga aaagtaaagg gtatgttctt ctattgaaat gtaagggttt tattaacatt   7200
aatgcacttc ctgctttata aaagaaatat tggtttgatt tccttaggcg tgtaacttgg   7260
acagtttaac ctgtaagttt gtgcctcagt aacccatctg taccatgggg ataatgtact   7320
catagggtga ttttaaaaga caaagctaat acttacaaag aagcaagttt aatgcctatc   7380
ttacataaat actttgtaag tagtagcagt tctttcagtg aggtgaggtt acatgaaaaa   7440
attccaagta tttgtaaaac tagtgggaag taagagggaa gctcgagttt tgattgaaaa   7500
gtggactaaa caagggcatt ttatgtactc agatctgaag caagttctgt gttgctgagg   7560
taaaagcatt tgtgttaata tggttttaaa aaccatgagt tcttctccct ccattgcagg   7620
attgcttata ttgaatttaa gacagaagct gatgcagaga aaacctttga agaaaagcag   7680
ggaacagaga tcgatgggcg atctatttcc ctgtactata ctggagagaa aggtcaaaat   7740
caagactata gaggtggaaa gaatagcact tggagtggta agaaattagg cttgttccaa   7800
ggttttcaga attggttgag ggaactcttc tagtctttgt atttcataag tttataaata   7860 cttttaatc aaagttactc aaatgtaggt gaagatcaag acatgatac cccaagtcat     7920 actcttattt ggaatagtaa tttccaatct tgaaatgaga gctctaaatc attttgcatt   7980
ggaatacagt aggcaaatca agcttccttt gtaggcatgt tttatacttt aaatgacttg   8040
accatgtgcg ttttgaactc agatgattct aggaaaacag accagtcatc agcctatgta   8100
agaacaacca gcaggacatt gcaacacgta ctaggtactt aatatgttga gtaacagaaa   8160
tggatttagc ttacgtcatg agtatttgta tataactcaa gcactgaaat tcttagggaa   8220
tagatattac tgttgtgacc gaagctggga cactgtttca gagtcttagg aatgtggctc   8280
tctatttcga ggtgaatcaa aaactctggt tttaagcaac ctctcctaca gtgcaacaga   8340
agaaactctt caggaagtat ttgagaaagc aactttatc aaagtacccc agaaccaaaa    8400
tggcaaatct aaagggtaag ataataccct tgtatcatca gttataggcc tatatatgtc   8460
ttagaggtct aaggacgtaa ggtcatgtgt cctgtagaaa aaagctaaat aattttagcc   8520
tagtaaatga gtgtaaaata agtatattta ggtccaacct tgagagaagg gccttggcca   8580
gatcatgtga ccagtggtat agagagcatg tgcctggtaa attactctaa gcattaactg   8640
ttcatcctca ggtatgcatt tatagagttt gcttcattcg aagacgctaa agaagcttta   8700
aattcctgta ataaaaggga aattgagggc agagcaatca ggctggagtt gcaaggaccc   8760
```

```
agggatcac ctaatgccag aagccgtaag ttcacctggt tagggtgctg tggttggggg    8820
tagcactctc ggtgctttgt ttattttgc acaaattctg tgtttcctgt tcgctactga    8880
gtgaacaata actggatatc gatgactgat tacctgagaa ataattgatg aaatctcaag    8940
aaaattcctc tagatagtca agttctgatc cagctgtcgt caactcagag tagcaagttt    9000
gcccatgatt tcctgcccca tccactgggc cccacctgct tgggttgctt tcccactttc    9060
catagaagac tggggcagga tatcaactat gcaatggcaa ttaaaaaatg taaacccaga    9120
atagccttta ctttaattaa ggactagttg gcttagttgc ttttaactgc tttttcacta    9180
taacaagtat cttggctagt agtcatacta ggcattgtgc aaattcagtg tacgaactgt    9240
gaattcacat aaatcgcaaa ttttttttc cttcccagag ccatccaaaa ctctgtttgt    9300
caaaggcctg tctgaggata ccactgaaga gacattaaag gagtcatttg acggctccgt    9360
tcgggcaagg atagttactg accgggaaac tgggtcctcc aaagggtaag ggaaggaagc    9420
gtgagtgctg cttccacttg aagggttttt tgttctgtgc agaccttgag tctaatgtgt    9480
cttctcattg agctccttct gtctatcagt ggcagtttat ggattcgcac gagaagaaga    9540
gagaattcac agaactagca ttattttacc ttctgtcttt acagaggtat atttagctgt    9600
attgtgagac attctggggt tcaagctgtc acaccagtta gttttccata gagagctact    9660
ctgctgcact ggtatctttt tcccaaataa acaaggctac ttctgtggga tggctcccca    9720
gcatgtacag ttaacttggg acatgtgtag taggtgcttt ttataatggg caatttcatt    9780
tggtgttcta ggtttggttt tgtagacttc aacagtgagg aggatgccaa ggaggccatg    9840
gaagacggtg aaattgatgg aaataaagtt accttggact gggccaaacc taagggtgaa    9900
ggtggcttcg ggggtcgtgg tggaggcaga ggcggctttg gaggacgagg tggtggtaga    9960
ggaggccgag gaggatttgg tggcagaggc cggggaggct ttggaggtaa ggcacgcaga   10020
gataatgaca ccacatagca tgtgctcttc agaccctgtg ccctgtcacg gttcctaatc   10080
actggggagg aggagctttg tacccattct tttaacagtg tcttgccttc ctcctgtagg   10140
gcgaggaggc ttccgaggag gcagaggagg aggaggtgac cacaagccac aaggaaagaa   10200
gacgaagttt gaatagcttc tgtccctctg ctttcccttt tccatttgaa agaaaggact   10260
ctgggggtttt tactgttacc tgatcaatga cagagccttc tgaggacatt ccaagacagt   10320
atacagtcct gtggtctcct tggaaatccg tctagttaac atttcaaggg caataccgtg   10380
ttggttttga ctggatattc atataaactt tttaaagagt tgagtgatag agctaaccct   10440
tatctgtaag ttttgaattt atattgtttc atcccatgta caaaaccatt ttttcctaca   10500
aatagtttgg gttttgttgt tgttactttt tttttttgttt ttgttttttt tttttttgcg   10560
ttcgtggggt tgtaaaagaa aagaaagcag aatgttttat catggttttt gcttcaccgc   10620
tttaggacaa attaaaagtc aactctggtg ccagacgtgt tacttcctaa agagtgtttc   10680
ccctggaatc tcactggaga gcatggcaaa gccagctctg ccacttgctt cacccatccc   10740
aatggaaatg gcttagtgcg tgtttccagt atcccagccc taactaactt ggttgaaatg   10800
ctggtgaggg gacctgctcc tgcagccctg gtgctgactt gaaggctgct gcagcttctc   10860
ctacttttag caggtctcga ggattatgtc tgaagaccac tctggaaaga ggtcgaggaa   10920
cagattagtc aggtttccta gg                                            10942
```

<210> SEQ ID NO 3
<211> LENGTH: 1561
<212> TYPE: DNA
<213> ORGANISM: Homo sapiens

<400> SEQUENCE: 3

```
gggcttatcc cgcctgtccc gccattctcg ctagttcgat cggtagcggg agcggagagc    60
ggaccccaga gagccctgag cagccccacc gccgccgccg gcctagttac catcacaccc   120
cgggaggagc cgcagctgcc gcagccggcc ccagtcacca tcaccgcaac catgagcagc   180
gaggccgaga cccagcagcc gcccgccgcc ccccccgccg ccccccgccct cagcgccgcc   240
gacaccaagc ccggcactac gggcagcggc gagggagcg gtggcccggg cggcctcaca   300
tcggcggcgc ctgccggcgg ggacaagaag gtcatcgcaa cgaaggtttt gggaacagta   360
aaatggttca atgtaaggaa cggatatggt ttcatcaaca ggaatgacac caaggaagat   420
gtatttgtac accagactgc cataaagaag aataacccca ggaagtacct tcgcagtgta   480
ggagatggag agactgtgga gtttgatgtt gttgaaggag aaaagggtgc ggaggcagca   540
aatgttacag gtcctggtgg tgttccagtt caaggcagta aatatgcagc agaccgtaac   600
cattatagac gctatccacg tcgtaggggt cctccacgca attaccagca aaattaccag   660
aatagtgaga gtggggaaaa gaacgaggga tcggagagtg ctcccgaagg ccaggcccaa   720
caacgccggc cctaccgcag gcgaaggttc ccaccttact acatgcggag accctatggg   780
cgtcgaccac agtattccaa ccctcctgtg cagggagaag tgatggaggg tgctgacaac   840
cagggtgcag gagaacaagg tagaccagtg aggcagaata tgtatcgggg atatagacca   900
cgattccgca ggggccctcc tcgccaaaga cagcctagag aggacggcaa tgaagaagat   960
aaagaaaatc aaggagatga gacccaaggt cagcagccac tcaacgtcg gtaccgccgc  1020
aacttcaatt accgacgcag acgcccagaa accctaaac cacaagatgg caaagagaca  1080
aaagcagccg atccaccagc tgagaattcg tccgctcccg aggctgagca gggcggggct  1140
gagtaaatgc cggcttacca tctctaccat catccggttt agtcatccaa caagaagaaa  1200
tatgaaattc cagcaataag aaatgaacaa aagattggag ctgaagacct aaagtgcttg  1260
cttttgccc gttgaccaga taaatagaac tatctgcatt atctatgcag catggggttt  1320
ttattatttt tacctaaaga cgtctcttt tggtaataac aaacgtgttt ttaaaaaag   1380
cctggtttt ctcaatacgc cttaaaggt ttttaaattg tttcatatct ggtcaagttg  1440
agatttttaa gaacttcatt tttaatttgt aataaaagtt tacaacttga ttttttcaaa  1500
aaagtcaaca aactgcaagc acctgttaat aaaggtctta ataataaaa aaaaaaaaa  1560
a                                                                 1561
```

<210> SEQ ID NO 4
<211> LENGTH: 58
<212> TYPE: DNA
<213> ORGANISM: Artificial Sequence
<220> FEATURE:
<223> OTHER INFORMATION: shRNA

<400> SEQUENCE: 4

```
ccgggccaag aatgtgttgt ccaaactcga gtttggacaa cacattcttg gcttttttg    58
```

<210> SEQ ID NO 5
<211> LENGTH: 58
<212> TYPE: DNA
<213> ORGANISM: Artificial Sequence
<220> FEATURE:
<223> OTHER INFORMATION: shRNA

<400> SEQUENCE: 5
ccgggcgcca gtgaagaaat ctatactcga gtatagattt cttcactggc gcttttg        58

<210> SEQ ID NO 6
<211> LENGTH: 58
<212> TYPE: DNA
<213> ORGANISM: Artificial Sequence
<220> FEATURE:
<223> OTHER INFORMATION: shRNA

<400> SEQUENCE: 6
ccgggcaaag gatgagttgc acattctcga gaatgtgcaa ctcatccttt gcttttg        58

<210> SEQ ID NO 7
<211> LENGTH: 59
<212> TYPE: DNA
<213> ORGANISM: Artificial Sequence
<220> FEATURE:
<223> OTHER INFORMATION: shRNA

<400> SEQUENCE: 7
ccggcctagt tctgtagaag acattctcga gaatgtcttc tacaggaact aggttttg      59

<210> SEQ ID NO 8
<211> LENGTH: 58
<212> TYPE: DNA
<213> ORGANISM: Artificial Sequence
<220> FEATURE:
<223> OTHER INFORMATION: shRNA

<400> SEQUENCE: 8
ccggcctagt tctgtagaag acattctcga gaatgtcttc tacagaacta ggttttg       58

<210> SEQ ID NO 9
<211> LENGTH: 58
<212> TYPE: DNA
<213> ORGANISM: Artificial Sequence
<220> FEATURE:
<223> OTHER INFORMATION: shRNA

<400> SEQUENCE: 9
ccggccttgg aaatccgtct agttactcga gtaactagac ggatttccaa ggttttg       58

<210> SEQ ID NO 10
<211> LENGTH: 59
<212> TYPE: DNA
<213> ORGANISM: Artificial Sequence
<220> FEATURE:
<223> OTHER INFORMATION: shRNA

<400> SEQUENCE: 10
ccggccggtg aaattgatgg aaataactcg agttatttcc atcaatttca ccgttttg     59

<210> SEQ ID NO 11
<211> LENGTH: 58
<212> TYPE: DNA
<213> ORGANISM: Artificial Sequence
<220> FEATURE:
<223> OTHER INFORMATION: shRNA

<400> SEQUENCE: 11
ccggcggtga aattgatgga ataactcga gttatttcca tcaatttcac cgttttg        58

<210> SEQ ID NO 12
<211> LENGTH: 58
<212> TYPE: DNA
<213> ORGANISM: Artificial Sequence

```
<220> FEATURE:
<223> OTHER INFORMATION: shRNA

<400> SEQUENCE: 12
ccggagtaaa gggattgctt atattctcga gaatataagc aatccctttta cttttttg      58

<210> SEQ ID NO 13
<211> LENGTH: 59
<212> TYPE: DNA
<213> ORGANISM: Artificial Sequence
<220> FEATURE:
<223> OTHER INFORMATION: shRNA

<400> SEQUENCE: 13
ccggcgttcg gggcaaggat agttacctcg aggtaactat ccttgcccga acgttttttg     59

<210> SEQ ID NO 14
<211> LENGTH: 58
<212> TYPE: DNA
<213> ORGANISM: Artificial Sequence
<220> FEATURE:
<223> OTHER INFORMATION: shRNA

<400> SEQUENCE: 14
ccgggcagtt caaggcagta aatatctcga gatatttact gccttgaact ggttttttg     58

<210> SEQ ID NO 15
<211> LENGTH: 58
<212> TYPE: DNA
<213> ORGANISM: Artificial Sequence
<220> FEATURE:
<223> OTHER INFORMATION: shRNA

<400> SEQUENCE: 15
ccggagcaga ccgtaaccat tatagctcga gctataatgg ttacggtctg ctttttttg     58

<210> SEQ ID NO 16
<211> LENGTH: 57
<212> TYPE: DNA
<213> ORGANISM: Artificial Sequence
<220> FEATURE:
<223> OTHER INFORMATION: shRNA

<400> SEQUENCE: 16
ccgggcttac catctctacc atcatctcga gatgatggta gagatggtaa gctttttt     57

<210> SEQ ID NO 17
<211> LENGTH: 57
<212> TYPE: DNA
<213> ORGANISM: Artificial Sequence
<220> FEATURE:
<223> OTHER INFORMATION: shRNA

<400> SEQUENCE: 17
ccgggacggc aatgaagaag ataaactcga gtttatcttc ttcattgccg tctttttt     57

<210> SEQ ID NO 18
<211> LENGTH: 57
<212> TYPE: DNA
<213> ORGANISM: Artificial Sequence
<220> FEATURE:
<223> OTHER INFORMATION: shRNA

<400> SEQUENCE: 18
ccggccagtt caaggcagta aatatctcga gatatttact gccttgaact ggtttttt     57
```

<210> SEQ ID NO 19
<211> LENGTH: 57
<212> TYPE: DNA
<213> ORGANISM: Artificial Sequence
<220> FEATURE:
<223> OTHER INFORMATION: shRNA

<400> SEQUENCE: 19
ccgggccatc aaacaagttt atgaactcga gttcataaac ttgtttgatg gctttttt       57

<210> SEQ ID NO 20
<211> LENGTH: 57
<212> TYPE: DNA
<213> ORGANISM: Artificial Sequence
<220> FEATURE:
<223> OTHER INFORMATION: shRNA

<400> SEQUENCE: 20
ccgggctgga attgatgaag ctcaactcga gttgagcttc atcaattcca gctttttt       57

<210> SEQ ID NO 21
<211> LENGTH: 57
<212> TYPE: DNA
<213> ORGANISM: Artificial Sequence
<220> FEATURE:
<223> OTHER INFORMATION: shRNA

<400> SEQUENCE: 21
ccggccatga ttaagggaga tacatctcga gatgtatctc ccttaatcat ggtttttt       57

<210> SEQ ID NO 22
<211> LENGTH: 57
<212> TYPE: DNA
<213> ORGANISM: Artificial Sequence
<220> FEATURE:
<223> OTHER INFORMATION: shRNA

<400> SEQUENCE: 22
ccggcgcgag acttctggca atttactcga gtaaattgcc agaagtctcg cgtttttt       57

<210> SEQ ID NO 23
<211> LENGTH: 57
<212> TYPE: DNA
<213> ORGANISM: Artificial Sequence
<220> FEATURE:
<223> OTHER INFORMATION: shRNA

<400> SEQUENCE: 23
ccgggcatcc tgactctgtt gacatctcga gatgtcaaca gagtcaggat gctttttt       57

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24 ggaacccta gtgatggagt t                                                21

<210> SEQ ID NO 25
<211> LENGTH: 16
<212> TYPE: DNA
<213> ORGANISM: Artificial Sequence
<220> FEATURE:
<223> OTHER INFORMATION: primer

<400> SEQUENCE: 25
cggcctcagt gagcga                                                          16

<210> SEQ ID NO 26
<211> LENGTH: 21
<212> TYPE: DNA
<213> ORGANISM: Artificial Sequence
<220> FEATURE:
<223> OTHER INFORMATION: probe

<400> SEQUENCE: 26
cactccctct ctgcgcgctc g                                                    21

<210> SEQ ID NO 27
<211> LENGTH: 294
<212> TYPE: PRT
<213> ORGANISM: Homo sapiens

<400> SEQUENCE: 27

```
Met Glu Asp Ser Met Asp Met Ser Pro Leu Arg Pro Gln Asn
1               5                   10                  15
Tyr Leu Phe Gly Cys Glu Leu Lys Ala Asp Lys Asp Tyr His Phe Lys
            20                  25                  30
Val Asp Asn Asp Glu Asn Glu His Gln Leu Ser Leu Arg Thr Val Ser
        35                  40                  45
Leu Gly Ala Gly Ala Lys Asp Glu Leu His Ile Val Glu Ala Glu Ala
    50                  55                  60
Met Asn Tyr Glu Gly Ser Pro Ile Lys Val Thr Leu Ala Thr Leu Lys
65                  70                  75                  80
Met Ser Val Gln Pro Thr Val Ser Leu Gly Gly Phe Glu Ile Thr Pro
                85                  90                  95
Pro Val Val Leu Arg Leu Lys Cys Gly Ser Gly Pro Val His Ile Ser
            100                 105                 110
Gly Gln His Leu Val Ala Val Glu Glu Asp Ala Glu Ser Glu Asp Glu
        115                 120                 125
Glu Glu Glu Asp Val Lys Leu Leu Ser Ile Ser Gly Lys Arg Ser Ala
    130                 135                 140
Pro Gly Gly Gly Ser Lys Val Pro Gln Lys Lys Val Lys Leu Ala Ala
145                 150                 155                 160
Asp Glu Asp Asp Asp Asp Asp Glu Glu Asp Asp Glu Asp Asp
                165                 170                 175
Asp Gly Asp Asp Phe Asp Glu Glu Ala Glu Glu Lys Ala Pro Val
                180                 185                 190
Lys Lys Ser Ile Arg Asp Thr Pro Ala Lys Asn Ala Gln Lys Ser Asn
            195                 200                 205
Gln Asn Gly Lys Asp Ser Lys Pro Ser Ser Thr Pro Arg Ser Lys Gly
        210                 215                 220
Gln Glu Ser Phe Lys Lys Gln Glu Lys Thr Pro Lys Thr Pro Lys Gly
225                 230                 235                 240
Pro Ser Ser Val Glu Asp Ile Lys Ala Lys Met Gln Ala Ser Ile Glu
                245                 250                 255
Lys Gly Gly Ser Leu Pro Lys Val Glu Ala Lys Phe Ile Asn Cys Val
            260                 265                 270
Lys Asn Cys Phe Arg Met Thr Asp Gln Glu Ala Ile Gln Asp Leu Trp
        275                 280                 285
```

Gln Trp Arg Lys Ser Leu
    290

<210> SEQ ID NO 28
<211> LENGTH: 707
<212> TYPE: PRT
<213> ORGANISM: Homo sapiens

<400> SEQUENCE: 28

Met Val Lys Leu Ala Lys Ala Gly Lys Asn Gln Gly Asp Pro Lys Lys
1               5                   10                  15

Met Ala Pro Pro Lys Glu Val Glu Glu Asp Ser Glu Asp Glu Glu
            20                  25                  30

Met Ser Glu Asp Glu Glu Asp Ser Ser Gly Glu Glu Val Val Ile
            35                  40                  45

Pro Gln Lys Lys Gly Lys Lys Ala Ala Ala Thr Ser Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
            115                 120                 125

Ile Pro Ala Lys Gly Ala Lys Asn Gly Lys Asn Ala Lys Lys Glu Asp
    130                 135                 140

Ser Asp Glu Glu Glu Asp Asp Ser Glu Glu Asp Glu Glu Asp Asp
145                 150                 155                 160

Glu Asp Glu Asp Glu Asp Glu Ile Glu Pro Ala Ala Met Lys
                165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Glu Glu Asp Asp Ser Glu Glu
            195                 200                 205

Glu Ala Met Glu Thr Thr Pro Ala Lys Gly Lys Lys Ala Ala Lys Val
    210                 215                 220

Val Pro Val Lys Ala Lys Asn Val Ala Glu Asp Glu Asp Glu Glu Glu
225                 230                 235                 240

Asp Asp Glu Asp Glu Asp Asp Asp Glu Asp Asp Glu Asp Asp
                245                 250                 255

Asp Asp Glu Asp Glu Glu Glu Glu Glu Glu Glu Glu Glu Pro
            260                 265                 270

Val Lys Glu Ala Pro Gly Lys Arg Lys Lys Glu Met Ala Lys Gln Lys
    275                 280                 285

Ala Ala Pro Glu Ala Lys Lys Gln Lys Val Glu Gly Thr Glu Pro Thr
    290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
            340                 345                 350

Asp Phe Glu Ser Ala Glu Asp Leu Glu Lys Ala Leu Glu Leu Thr Gly
            355                 360                 365

Leu Lys Val Phe Gly Asn Glu Ile Lys Leu Glu Lys Pro Lys Gly Lys
            370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
                420                 425                 430

Tyr Ile Glu Phe Lys Thr Glu Ala Asp Ala Glu Lys Thr Phe Glu Glu
            435                 440                 445

Lys Gln Gly Thr Glu Ile Asp Gly Arg Ser Ile Ser Leu Tyr Tyr Thr
450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
            500                 505                 510

Lys Val Pro Gln Asn Gln Asn Gly Lys Ser Lys Gly Tyr Ala Phe Ile
            515                 520                 525

Glu Phe Ala Ser Phe Glu Asp Ala Lys Glu Ala Leu Asn Ser Cys Asn
530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
            595                 600                 605

Ser Lys Gly Phe Gly Phe Val Asp Phe Asn Ser Glu Glu Asp Ala Lys
610                 615                 620

Glu Ala Met Glu Asp Gly Glu Ile Asp Gly Asn Lys Val Thr Leu Asp
625                 630                 635                 640

Trp Ala Lys Pro Lys Gly Glu Gly Gly Phe Gly Gly Arg Gly Gly Gly
                645                 650                 655

Arg Gly Gly Phe Gly Gly Arg Gly Gly Gly Arg Gly Arg Gly Gly Gly
            660                 665                 670

Phe Gly Gly Arg Gly Arg Gly Gly Phe Gly Gly Arg Gly Gly Phe Arg
            675                 680                 685

Gly Gly Arg Gly Gly Gly Asp His Lys Pro Gln Gly Lys Lys Thr
690                 695                 700

Lys Phe Glu
705

<210> SEQ ID NO 29
<211> LENGTH: 324
<212> TYPE: PRT
<213> ORGANISM: Homo sapiens

<400> SEQUENCE: 29

Met Ser Ser Glu Ala Glu Thr Gln Gln Pro Ala Ala Pro Ala
1               5                   10                  15

Ala Pro Ala Leu Ser Ala Ala Asp Thr Lys Pro Gly Thr Thr Gly Ser 20                  25                  30
Gly Ala Gly Ser Gly Gly Pro Gly Gly Leu Thr Ser Ala Ala Pro Ala
                35                  40                  45
Gly Gly Asp Lys Lys Val Ile Ala Thr Lys Val Leu Gly Thr Val Lys
        50                  55                  60
Trp Phe Asn Val Arg Asn Gly Tyr Gly Phe Ile Asn Arg Asn Asp Thr
 65                  70                  75                  80
Lys Glu Asp Val Phe Val His Gln Thr Ala Ile Lys Lys Asn Asn Pro
                85                  90                  95
Arg Lys Tyr Leu Arg Ser Val Gly Asp Gly Glu Thr Val Glu Phe Asp
            100                 105                 110
Val Val Glu Gly Glu Lys Gly Ala Glu Ala Ala Asn Val Thr Gly Pro
        115                 120                 125
Gly Gly Val Pro Val Gln Gly Ser Lys Tyr Ala Ala Asp Arg Asn His
        130                 135                 140
Tyr Arg Arg Tyr Pro Arg Arg Gly Pro Pro Arg Asn Tyr Gln Gln
145                 150                 155                 160
Asn Tyr Gln Asn Ser Glu Ser Gly Glu Lys Asn Glu Gly Ser Glu Ser
                165                 170                 175
Ala Pro Glu Gly Gln Ala Gln Gln Arg Pro Tyr Arg Arg Arg
            180                 185                 190
Phe Pro Pro Tyr Tyr Met Arg Arg Pro Tyr Gly Arg Arg Pro Gln Tyr
            195                 200                 205
Ser Asn Pro Pro Val Gln Gly Glu Val Met Glu Gly Ala Asp Asn Gln
        210                 215                 220
Gly Ala Gly Glu Gln Gly Arg Pro Val Arg Gln Asn Met Tyr Arg Gly
225                 230                 235                 240
Tyr Arg Pro Arg Phe Arg Arg Gly Pro Pro Arg Gln Arg Gln Pro Arg
                245                 250                 255
Glu Asp Gly Asn Glu Glu Asp Lys Glu Asn Gln Gly Asp Glu Thr Gln
            260                 265                 270
Gly Gln Gln Pro Pro Gln Arg Arg Tyr Arg Arg Asn Phe Asn Tyr Arg
        275                 280                 285
Arg Arg Arg Pro Glu Asn Pro Lys Pro Gln Asp Gly Lys Glu Thr Lys
        290                 295                 300
Ala Ala Asp Pro Pro Ala Glu Asn Ser Ser Ala Pro Glu Ala Glu Gln
305                 310                 315                 320
Gly Gly Ala Glu

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
ttcctacttg gcagtacatc tacg                                          24

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31

```
gtcaatggggg tggagacttg g                                                21

<210> SEQ ID NO 32
<211> LENGTH: 25
<212> TYPE: DNA
<213> ORGANISM: Artificial Sequence
<220> FEATURE:
<223> OTHER INFORMATION: probe

<400> SEQUENCE: 32
tgagtcaaac cgctatccac gccca                                             25

<210> SEQ ID NO 33
<211> LENGTH: 25
<212> TYPE: DNA
<213> ORGANISM: Artificial Sequence
<220> FEATURE:
<223> OTHER INFORMATION: gRNA

<400> SEQUENCE: 33
atcggcggcg cctgccggcg gtttt                                             25

<210> SEQ ID NO 34
<211> LENGTH: 25
<212> TYPE: DNA
<213> ORGANISM: Artificial Sequence
<220> FEATURE:
<223> OTHER INFORMATION: gRNA

<400> SEQUENCE: 34
cgccggcagg cgccgccgat cggtg                                             25

<210> SEQ ID NO 35
<211> LENGTH: 24
<212> TYPE: DNA
<213> ORGANISM: Artificial Sequence
<220> FEATURE:
<223> OTHER INFORMATION: gRNA

<400> SEQUENCE: 35
gtaatggctt ttgtagggtg gttt                                              24

<210> SEQ ID NO 36
<211> LENGTH: 25
<212> TYPE: DNA
<213> ORGANISM: Artificial Sequence
<220> FEATURE:
<223> OTHER INFORMATION: gRNA

<400> SEQUENCE: 36
caccctacaa aagccattac cggtg                                             25

<210> SEQ ID NO 37
<211> LENGTH: 25
<212> TYPE: DNA
<213> ORGANISM: Artificial Sequence
<220> FEATURE:
<223> OTHER INFORMATION: gRNA

<400> SEQUENCE: 37
ggaccatacc tgcggaatcg gtttt                                             25

<210> SEQ ID NO 38
<211> LENGTH: 25
<212> TYPE: DNA
```

```
<213> ORGANISM: Artificial Sequence
<220> FEATURE:
<223> OTHER INFORMATION: gRNA

<400> SEQUENCE: 38
cgattccgca ggtatggtcc cggtg                                          25

<210> SEQ ID NO 39
<211> LENGTH: 24
<212> TYPE: DNA
<213> ORGANISM: Artificial Sequence
<220> FEATURE:
<223> OTHER INFORMATION: gRNA

<400> SEQUENCE: 39
caaagacagc ctagaaggag tttt                                           24

<210> SEQ ID NO 40
<211> LENGTH: 25
<212> TYPE: DNA
<213> ORGANISM: Artificial Sequence
<220> FEATURE:
<223> OTHER INFORMATION: gRNA

<400> SEQUENCE: 40
tcctctctag gctgtctttg cggtg                                          25
```